US011987609B2

(12) United States Patent
Xu et al.

(10) Patent No.: US 11,987,609 B2
(45) Date of Patent: May 21, 2024

(54) PROTEINACEOUS HETERODIMER AND USE THEREOF

(71) Applicant: DINGFU BIOTARGET CO., LTD., Jiangsu (CN)

(72) Inventors: Ting Xu, Jiangsu (CN); Yan Luan, Jiangsu (CN); Jianjian Peng, Jiangsu (CN); Shilong Fu, Jiangsu (CN)

(73) Assignee: DINGFU BIOTARGET CO., LTD., Jiangsu (CN)

( * ) Notice: Subject to any disclaimer, the term of this patent is extended or adjusted under 35 U.S.C. 154(b) by 337 days.

(21) Appl. No.: 16/649,893

(22) PCT Filed: Sep. 21, 2018

(86) PCT No.: PCT/CN2018/107099

§ 371 (c)(1),
(2) Date: Mar. 23, 2020

(87) PCT Pub. No.: WO2019/057180

PCT Pub. Date: Mar. 28, 2019

(65) Prior Publication Data

US 2020/0277350 A1 Sep. 3, 2020

(51) Int. Cl.

| | |
|---|---|
| ***C07K 1/00*** | (2006.01) |
| ***C07K 14/54*** | (2006.01) |
| ***C07K 16/00*** | (2006.01) |
| ***C07K 16/32*** | (2006.01) |
| ***C12P 21/08*** | (2006.01) |
| *A61K 39/00* | (2006.01) |
| *A61K 45/00* | (2006.01) |

(52) U.S. Cl.

CPC .......... *C07K 14/5428* (2013.01); *C07K 16/32* (2013.01); *A61K 2039/505* (2013.01); *C07K 2317/52* (2013.01); *C07K 2317/569* (2013.01); *C07K 2317/622* (2013.01); *C07K 2317/64* (2013.01); *C07K 2317/74* (2013.01); *C07K 2319/30* (2013.01)

(58) Field of Classification Search

None

See application file for complete search history.

(56) References Cited

U.S. PATENT DOCUMENTS

| | | | | |
|---|---|---|---|---|
| 4,500,707 A | | 2/1985 | Catruthers et al. | |
| 4,536,327 A | | 8/1985 | Ramisse et al. | |
| 5,700,637 A | | 12/1997 | Southern | |
| 5,731,168 A | | 3/1998 | Carter et al. | |
| 7,348,004 B2 | * | 3/2008 | Peters | C07K 14/745 530/387.3 |
| 7,951,917 B1 | * | 5/2011 | Arathoon | C07K 16/00 424/134.1 |
| 2007/0122383 A1 | | 5/2007 | Horwitz et al. | |
| 2012/0149876 A1 | * | 6/2012 | Von Kreudenstein | C07K 16/32 530/387.3 |
| 2012/0244578 A1 | * | 9/2012 | Kannan | C07K 16/00 435/254.2 |
| 2017/0020963 A1 | * | 1/2017 | Qu | A61K 38/2086 |
| 2018/0362668 A1 | * | 12/2018 | Xu | C07K 19/00 |

FOREIGN PATENT DOCUMENTS

| | | | |
|---|---|---|---|
| CN | 102558355 | 7/2012 | |
| CN | 103509121 | 1/2014 | |
| CN | 104540848 | 4/2015 | |
| CN | 105189562 A | 12/2015 | |
| CN | 106883297 | 6/2017 | |
| CN | 107001485 | 8/2017 | |
| JP | 2015531591 A | 11/2015 | |
| JP | 2017503498 A | 2/2017 | |
| WO | 2012045334 A1 | 4/2012 | |
| WO | 2014145806 A3 | 9/2014 | |
| WO | 2015/103928 | 7/2015 | |
| WO | 2016100788 A1 | 6/2016 | |
| WO | 2017/101828 | 6/2017 | |
| WO | WO-2017101828 A1 * | 6/2017 | A61K 39/395 |
| WO | 2019/057180 | 3/2019 | |

OTHER PUBLICATIONS

Chen et al. Adv. Drug Deliv Rev. 2013, 15;65(10):1357-1369. (Year: 2013).*

China Patent Application 2018800596533 Search Report dated Jan. 13, 2022.

Davis, Jonathan J., et al., SEEDbodies: fusion proteins based on strand-exchange engineered domain (SEED) CH3 heterodimers in an Fc analogue platform for asymmetric binders or immunofusions and biospecific antibodies; Protein Engineering Design 7 Selection, vol. 23, No. 4, pp. 195-202, Feb. 4, 2010.

Josephson, Kristopher, et al., Design and Analysis of an Engineered human Interleukin-10 Monomer; J of Biological Chemistry, vol. 274, No. 18, pp. 13552-13557, May 5, 2000, The Am Soc for Biochemistry and Molecular Biology, Inc.

Carter, Paul, "Bispecific human lgG by design", Journal of Immunological Methods, Elsevier, vol. 240, 2001, pp. 7-15.

(Continued)

*Primary Examiner* — Chun W Dahle

(74) *Attorney, Agent, or Firm* — Honigman LLP; Thomas A. Wootton, Esq.; Jonathan P. O'Brien

(57) ABSTRACT

Provided are proteinaceous heterodimers, pharmaceutical compositions, medicaments and/or kits comprising the proteinaceous heterodimers, methods for producing the proteinaceous heterodimers, and uses thereof.

2 Claims, 7 Drawing Sheets

Specification includes a Sequence Listing.

(56) References Cited

OTHER PUBLICATIONS

Disis, Mary L. et al., "High-Titer HER-2/neu Protein-Specific Antibody Can Be Detected in Patients With Erly-Stage Breast Cancer", Journal of Clinical Oncology, vol. 15, No. 11, Nov. 1997, pp. 3363-3367.
Ha, Ji-Hee et al., "Immunoglobulin Fc Heterodimer Platform Technology: From Design to Applications in Therapeutic Antibodies and Proteins", Frontiers in Immunology, vol. 7, No. 29, Oct. 6, 2016, pp. 1-16.
International Search Report from PCT/CN2018/107099 dated Dec. 27, 2018.
Levin, Aron M. et al., "Exploiting a natural conformational switch to engineer an Interleukin-2 superkine", Nature, Oct. 26, 2020, pp. 1-12.
Ridgway, John B.B. et al., "'Knobs-into-holes' engineering of antibody CH3 domains for heavy chain heterodimerization", Protein Engineeringm vol. 9, No. 7, 1996, pp. 617-621.
Smith, Sidney R. et al., "Administration of Interleukin-10 at the Time of Priming Protects Corynebacterium parvum-Primed Mice against LPS- and TNF-a-Induced Lethality", Cellular Immunology, vol. 173, No. 0269, 1996, pp. 207-214.
Written Opinion of the International Searching Authority from PCT/CN2018/107099 dated Dec. 27, 2018.

* cited by examiner

Signal: VWD1 A, Wavelength=280 nm

| RT [min] | Type | Width [min] | Area | Height | Area% | Name |
|---|---|---|---|---|---|---|
| 12.157 | BF | 0.4440 | 1232.7279 | 38.8707 | 27.0888 | |
| 16.399 | VB | 0.6609 | 93.6304 | 1.9370 | 2.0575 | |
| 18.868 | BF | 0.5366 | 3187.5945 | 88.8507 | 70.0463 | |
| 20.321 | VV R | 0.7264 | 36.7437 | 0.8430 | 0.8074 | |
| | | Sum | 4550.6966 | | | |

Signal: VWD1 A, Wavelength=280 nm

| RT [min] | Type | Width [min] | Area | Height | Area% | Name |
|---|---|---|---|---|---|---|
| 12.121 | BV R | 0.6512 | 202.2544 | 4.2426 | 3.3066 | |
| 15.847 | BB | 0.4849 | 22.0707 | 0.5515 | 0.3608 | |
| 18.457 | BV | 0.7123 | 3587.3225 | 74.8328 | 58.6487 | |
| 20.674 | VBA | 0.9797 | 2304.9841 | 34.3121 | 37.6839 | |
| | | Sum | 6116.6318 | | | |

Signal: VWD1 A, Wavelength=280 nm

| RT [min] | Type | Width [min] | Area | Height | Area% | Name |
|---|---|---|---|---|---|---|
| 12.163 | BV R | 0.4854 | 456.1467 | 12.9669 | 26.4192 | |
| 17.351 | VF R | 0.5234 | 1232.2134 | 35.3741 | 71.3677 | |
| 18.422 | VB | 0.5815 | 38.2103 | 1.0952 | 2.2131 | |
| | | Sum | 1726.5704 | | | |

| | Erb-$(IL10)_2$ | Reverse-$(IL10)_2$-Fc9 | $(IL10)_2$-Fc6 | $(IL10)_2$-Fc9 |
|---|---|---|---|---|
| EC50 | 222.8 | 9.077 | 143.5 | 137.2 |

SEQUENCE LISTING

<160> NUMBER OF SEQ ID NOS: 59

<210> SEQ ID NO 1
<211> LENGTH: 227
<212> TYPE: PRT
<213> ORGANISM: Artificial Sequence
<220> FEATURE:
<223> OTHER INFORMATION: Y349C+T366W

<400> SEQUENCE: 1

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 2
<211> LENGTH: 227
<212> TYPE: PRT
<213> ORGANISM: Artificial Sequence
<220> FEATURE:
<223> OTHER INFORMATION: D356C+T366S+L368A+Y407V+F405K

<400> SEQUENCE: 2

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

-continued

```
His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Cys Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 3
<211> LENGTH: 227
<212> TYPE: PRT
<213> ORGANISM: Artificial Sequence
<220> FEATURE:
<223> OTHER INFORMATION: Y349C+T366W+F405K

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190
```

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 4
<211> LENGTH: 227
<212> TYPE: PRT
<213> ORGANISM: Artificial Sequence
<220> FEATURE:
<223> OTHER INFORMATION: D356C+T366S+L368A+Y407V

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Cys Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 5
<211> LENGTH: 227
<212> TYPE: PRT
<213> ORGANISM: Artificial Sequence
<220> FEATURE:
<223> OTHER INFORMATION: Y349C+T366W+K409E

<400> SEQUENCE: 5

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
35 40 45

Glu Asn Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Cys Thr Leu Pro Pro Ser Arg Asp Glu Leu Thr Lys Asn Gln Val Ser
130 135 140

Leu Trp Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Glu Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys
225

<210> SEQ ID NO 6
<211> LENGTH: 227
<212> TYPE: PRT
<213> ORGANISM: Artificial Sequence
<220> FEATURE:
<223> OTHER INFORMATION: Y349C+T366W+K409A

<400> SEQUENCE: 6

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asn Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Cys Thr Leu Pro Pro Ser Arg Asp Glu Leu Thr Lys Asn Gln Val Ser
130 135 140

Leu Trp Cys Leu Val Lys Gly Phe Tyr Pro Ser Asp Ile Ala Val Glu
145 150 155 160

-continued

```
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 7
<211> LENGTH: 227
<212> TYPE: PRT
<213> ORGANISM: Artificial Sequence
<220> FEATURE:
<223> OTHER INFORMATION: Y349C+T366W+F405K+K360E+Q347E

<400> SEQUENCE: 7

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Cys Thr Leu Pro Pro Ser Arg Asp Glu Leu Thr Glu Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 8
<211> LENGTH: 227
<212> TYPE: PRT
<213> ORGANISM: Artificial Sequence
<220> FEATURE:
<223> OTHER INFORMATION: D356C+T366S+L368A+Y407V+Q347R
```

<400> SEQUENCE: 8

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Arg Val
115 120 125

Tyr Thr Leu Pro Pro Ser Arg Cys Glu Leu Thr Lys Asn Gln Val Ser
130 135 140

Leu Ser Cys Ala Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Val Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys
225

<210> SEQ ID NO 9
<211> LENGTH: 227
<212> TYPE: PRT
<213> ORGANISM: Artificial Sequence
<220> FEATURE:
<223> OTHER INFORMATION: Y349C+T366W+F405K+Q347R

<400> SEQUENCE: 9

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asn Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Arg Val 115 120 125

Cys Thr Leu Pro Pro Ser Arg Asp Glu Leu Thr Lys Asn Gln Val Ser
130 135 140

Leu Trp Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Lys Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys
225

<210> SEQ ID NO 10
<211> LENGTH: 227
<212> TYPE: PRT
<213> ORGANISM: Artificial Sequence
<220> FEATURE:
<223> OTHER INFORMATION: D356C+T366S+L368A+Y407V+K360E+Q347E

<400> SEQUENCE: 10

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Glu Val
115 120 125

Tyr Thr Leu Pro Pro Ser Arg Cys Glu Leu Thr Glu Asn Gln Val Ser
130 135 140

Leu Ser Cys Ala Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Val Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys
225

<210> SEQ ID NO 11
<211> LENGTH: 227
<212> TYPE: PRT
<213> ORGANISM: Artificial Sequence
<220> FEATURE:
<223> OTHER INFORMATION: Y349C+T366W+K409A+K360E+Q347E

<400> SEQUENCE: 11

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Cys Thr Leu Pro Pro Ser Arg Asp Glu Leu Thr Glu Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 12
<211> LENGTH: 227
<212> TYPE: PRT
<213> ORGANISM: Artificial Sequence
<220> FEATURE:
<223> OTHER INFORMATION: D356C+T366S+L368A+Y407V+F405K+Q347R

<400> SEQUENCE: 12

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

-continued

```
Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Arg Val
        115                 120                 125

Tyr Thr Leu Pro Pro Ser Arg Cys Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 13
<211> LENGTH: 227
<212> TYPE: PRT
<213> ORGANISM: Artificial Sequence
<220> FEATURE:
<223> OTHER INFORMATION: Y349C+T366W+K409A+Q347R

<400> SEQUENCE: 13

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Arg Val
        115                 120                 125

Cys Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205
```

-continued

His Glu Ala Leu His Asn His Tyr Thr Gln Lys Ser Leu Ser Leu Ser
    210                 215                 220

Pro Gly Lys
225

<210> SEQ ID NO 14
<211> LENGTH: 227
<212> TYPE: PRT
<213> ORGANISM: Artificial Sequence
<220> FEATURE:
<223> OTHER INFORMATION: D356C+T366S+L368A+Y407V+F405K+K360E+Q347E

<400> SEQUENCE: 14

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Tyr Thr Leu Pro Pro Ser Arg Cys Glu Leu Thr Glu Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 15
<211> LENGTH: 227
<212> TYPE: PRT
<213> ORGANISM: Artificial Sequence
<220> FEATURE:
<223> OTHER INFORMATION: T366W+K409A+K392D

<400> SEQUENCE: 15

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Ser Arg Asp Glu Leu Thr Lys Asn Gln Val Ser
130 135 140

Leu Trp Cys Leu Val Lys Gly Phe Tyr Pro Ser Asp Ile Ala Val Glu
145 150 155 160

Trp Glu Ser Asn Gly Gln Pro Glu Asn Asn Tyr Asp Thr Thr Pro Pro
165 170 175

Val Leu Asp Ser Asp Gly Ser Phe Phe Leu Tyr Ser Ala Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys
225

<210> SEQ ID NO 16
<211> LENGTH: 227
<212> TYPE: PRT
<213> ORGANISM: Artificial Sequence
<220> FEATURE:
<223> OTHER INFORMATION: T366S+L368A+Y407V+D399S+F405K

<400> SEQUENCE: 16

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Ser Arg Asp Glu Leu Thr Lys Asn Gln Val Ser
130 135 140

Leu Ser Cys Ala Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

```
Val Leu Ser Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 17
<211> LENGTH: 227
<212> TYPE: PRT
<213> ORGANISM: Artificial Sequence
<220> FEATURE:
<223> OTHER INFORMATION: T366W+K409A

<400> SEQUENCE: 17

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 18
<211> LENGTH: 227
<212> TYPE: PRT
<213> ORGANISM: Artificial Sequence
<220> FEATURE:
<223> OTHER INFORMATION: T366S+L368G+Y407A+F405K

<400> SEQUENCE: 18

Asp Lys Thr His Thr Cys Pro Pro Cys Pro Ala Pro Glu Leu Leu Gly
```

```
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Gly Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Ala Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 19
<211> LENGTH: 227
<212> TYPE: PRT
<213> ORGANISM: Artificial Sequence
<220> FEATURE:
<223> OTHER INFORMATION: T366W+K409A+Y349D

<400> SEQUENCE: 19

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Asp Thr Leu Pro Pro Ser Arg Asp Glu Leu Thr Lys Asn Gln Val Ser
```

```
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 20
<211> LENGTH: 227
<212> TYPE: PRT
<213> ORGANISM: Artificial Sequence
<220> FEATURE:
<223> OTHER INFORMATION: T366S+L368A+Y407V+F405K+E357A

<400> SEQUENCE: 20

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Ala Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 21
<211> LENGTH: 227
<212> TYPE: PRT
```

<213> ORGANISM: Artificial Sequence
<220> FEATURE:
<223> OTHER INFORMATION: T366W+K409A+Y349D+S354D

<400> SEQUENCE: 21

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Asp Thr Leu Pro Pro Asp Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 22
<211> LENGTH: 227
<212> TYPE: PRT
<213> ORGANISM: Artificial Sequence
<220> FEATURE:
<223> OTHER INFORMATION: T366W+F405K

<400> SEQUENCE: 22

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 23
<211> LENGTH: 227
<212> TYPE: PRT
<213> ORGANISM: Artificial Sequence
<220> FEATURE:
<223> OTHER INFORMATION: T366S+L368A+Y407V+K409A

<400> SEQUENCE: 23

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220
```

Pro Gly Lys
225

<210> SEQ ID NO 24
<211> LENGTH: 227
<212> TYPE: PRT
<213> ORGANISM: Artificial Sequence
<220> FEATURE:
<223> OTHER INFORMATION: T366W+F405K+D399S

<400> SEQUENCE: 24

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asn Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Ser Arg Asp Glu Leu Thr Lys Asn Gln Val Ser
130 135 140

Leu Trp Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Ser Ser Asp Gly Ser Phe Lys Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys
225

<210> SEQ ID NO 25
<211> LENGTH: 227
<212> TYPE: PRT
<213> ORGANISM: Artificial Sequence
<220> FEATURE:
<223> OTHER INFORMATION: T366S+L368A+Y407V+K409A+K392D

<400> SEQUENCE: 25

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

```
His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Asp Thr Thr Pro Pro
                165                 170                 175

Val Leu Asp Ser Asp Gly Ser Phe Phe Leu Val Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 26
<211> LENGTH: 227
<212> TYPE: PRT
<213> ORGANISM: Artificial Sequence
<220> FEATURE:
<223> OTHER INFORMATION: T366W+F405K

<400> SEQUENCE: 26

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Gly Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Ala Ser Ala Leu Thr Val
            180                 185                 190
```

```
Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 27
<211> LENGTH: 227
<212> TYPE: PRT
<213> ORGANISM: Artificial Sequence
<220> FEATURE:
<223> OTHER INFORMATION: T366S+L368G+Y407A+K409A

<400> SEQUENCE: 27

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Asp Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 28
<211> LENGTH: 227
<212> TYPE: PRT
<213> ORGANISM: Artificial Sequence
<220> FEATURE:
<223> OTHER INFORMATION: T366W +F405K +Y349D

<400> SEQUENCE: 28

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
```

```
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Ala Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 29
<211> LENGTH: 227
<212> TYPE: PRT
<213> ORGANISM: Artificial Sequence
<220> FEATURE:
<223> OTHER INFORMATION: T366S+L368A+Y407V +K409A +E357A

<400> SEQUENCE: 29

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Asp Thr Leu Pro Pro Asp Arg Asp Glu Leu Thr Lys Asn Gln Val Ser
    130                 135                 140

Leu Trp Cys Leu Val Lys Gly Phe Tyr Pro Ser Asp Ile Ala Val Glu
```

-continued

```
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 30
<211> LENGTH: 227
<212> TYPE: PRT
<213> ORGANISM: Artificial Sequence
<220> FEATURE:
<223> OTHER INFORMATION: wildtype human IgG1-Fc region amino acid

<400> SEQUENCE: 30

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 31
<211> LENGTH: 681
<212> TYPE: DNA
<213> ORGANISM: Artificial Sequence
<220> FEATURE:
<223> OTHER INFORMATION: Fc gene fragment
```

<400> SEQUENCE: 31
gacaagaccc acacctgccc cccctgcccc gcccccgagc tgctgggcgg ccccagcgtg 60
ttcctgttcc cccccaagcc caaggacacc ctgatgatca gccgcacccc cgaggtgacc 120
tgcgtggtgg tggacgtgag ccacgagaac cccgaggtga agttcaactg gtacgtggac 180
ggcgtggagg tgcacaacgc caagaccaag ccccgcgagg agcagtacaa cagcacctac 240
cgcgtggtga gcgtgctgac cgtgctgcac caggactggc tgaacggcaa ggagtacaag 300
tgcaaggtga gcaacaaggc cctgcccgcc cccatcgaga agaccatcag caaggccaag 360
ggccagcccc gcgagcccca ggtgtacacc ctgcccccca gccgcgacga gctgaccaag 420
aaccaggtga gcctgacctg cctggtgaag ggcttctacc ccagcgacat cgccgtggag 480
tgggagagca acggccagcc cgagaacaac tacaagacca ccccccccgt gctggacagc 540
gacggcagct tcttcctgta cagcaagctg accgtggaca agagccgctg gcagcagggc 600
aacgtgttca gctgcagcgt gatgcacgag gccctgcaca accactacac ccagaagagc 660
ctgagcctga gccccggcaa g 681

<210> SEQ ID NO 32
<211> LENGTH: 741
<212> TYPE: DNA
<213> ORGANISM: Artificial Sequence
<220> FEATURE:
<223> OTHER INFORMATION: polynucleotide fragment encoding a mouse
kappaIII signal peptide

<400> SEQUENCE: 32
atggagaccg acaccctgct gctgtgggtg ctgctgctgt gggtgcccgg cagcaccggc 60
gacaagaccc acacctgccc cccctgcccc gcccccgagc tgctgggcgg ccccagcgtg 120
ttcctgttcc cccccaagcc caaggacacc ctgatgatca gccgcacccc cgaggtgacc 180
tgcgtggtgg tggacgtgag ccacgagaac cccgaggtga agttcaactg gtacgtggac 240
ggcgtggagg tgcacaacgc caagaccaag ccccgcgagg agcagtacaa cagcacctac 300
cgcgtggtga gcgtgctgac cgtgctgcac caggactggc tgaacggcaa ggagtacaag 360
tgcaaggtga gcaacaaggc cctgcccgcc cccatcgaga agaccatcag caaggccaag 420
ggccagcccc gcgagcccca ggtgtacacc ctgcccccca gccgcgacga gctgaccaag 480
aaccaggtga gcctgacctg cctggtgaag ggcttctacc ccagcgacat cgccgtggag 540
tgggagagca acggccagcc cgagaacaac tacaagacca ccccccccgt gctggacagc 600
gacggcagct tcttcctgta cagcaagctg accgtggaca agagccgctg gcagcagggc 660
aacgtgttca gctgcagcgt gatgcacgag gccctgcaca accactacac ccagaagagc 720
ctgagcctga gccccggcaa g 741

<210> SEQ ID NO 33
<211> LENGTH: 1473
<212> TYPE: DNA
<213> ORGANISM: Artificial Sequence
<220> FEATURE:
<223> OTHER INFORMATION: gene of ScFv-Fc fusion protein

<400> SEQUENCE: 33
atggagaccg acaccctgct gctgtgggtg ctgctgctgt gggtgcccgg cagcaccggc 60
gaggtgcagc tgctggagag cggcggcggc gtggtgcagc ccggccgcag cctgcgcctg 120
agctgcatcg ccagcggctt caccttcagc agctacccca tgacctgggt gcgccaggcc 180

-continued

```
cccggcaagg gcctggagtg ggtggccagc atcagctacg acggcagcta caagtacaag    240

gccgacagca tgaagggccg cctgaccatc agccgcgaca acagcaagaa caccctgtac    300

ctggagatga acagcctgac cgccgaggac accgccgtgt actactgcgc ccgcaccgcc    360

ttcttcaacg cctacgactt ctggggccag ggcaccctgg tgaccgtgag cagcgccagc    420

accaagggcc ccagcgtggg cggcggcggc agcggcggcg gcggcagcga gatcgtgatg    480

acccagagcc ccgccaccct gagcgtgagc cccggcgagc gcgccaccct gagctgccgc    540

gccagccaga gcgtgcgcag caacctggcc tggtaccagc agaagcccgg ccaggccccc    600

cgcctgctga tctacgccgc cagcacccgc gccaccggca tccccgcccg cttcagcggc    660

agcggcagcg gcaccgagtt caccctgacc atcagcagcc tgcagagcga ggacttcgcc    720

gtgtactact gccagcagta caacgagtgg ttccgcacca gcggccaggg caccaaggtg    780

gagatcaagc gcgacaagac ccacacctgc ccccccctgcc ccgcccccga gctgctgggc    840

ggccccagcg tgttcctgtt cccccccaag cccaaggaca ccctgatgat cagccgcacc    900

cccgaggtga cctgcgtggt ggtggacgtg agccacgaga accccgaggt gaagttcaac    960

tggtacgtgg acggcgtgga ggtgcacaac gccaagacca agccccgcga ggagcagtac   1020

aacagcacct accgcgtggt gagcgtgctg accgtgctgc accaggactg gctgaacggc   1080

aaggagtaca agtgcaaggt gagcaacaag gccctgcccg cccccatcga gaagaccatc   1140

agcaaggcca agggccagcc ccgcgagccc caggtgtaca ccctgccccc cagccgcgac   1200

gagctgacca agaaccaggt gagcctgacc tgcctggtga agggcttcta ccccagcgac   1260

atcgccgtgg agtgggagag caacggccag cccgagaaca actacaagac caccccccccc   1320

gtgctggaca gcgacggcag cttcttcctg tacagcaagc tgaccgtgga caagagccgc   1380

tggcagcagg gcaacgtgtt cagctgcagc gtgatgcacg aggccctgca caaccactac   1440

acccagaaga gcctgagcct gagccccggc aag                                1473
```

<210> SEQ ID NO 34
<211> LENGTH: 471
<212> TYPE: PRT
<213> ORGANISM: Artificial Sequence
<220> FEATURE:
<223> OTHER INFORMATION: ScFv-Fc fusion protein

<400> SEQUENCE: 34

```
Glu Val Gln Leu Leu Glu Ser Gly Gly Gly Val Val Gln Pro Gly Arg
1               5                   10                  15

Ser Leu Arg Leu Ser Cys Ile Ala Ser Gly Phe Thr Phe Ser Ser Tyr
            20                  25                  30

Pro Met Thr Trp Val Arg Gln Ala Pro Gly Lys Gly Leu Glu Trp Val
        35                  40                  45

Ala Ser Ile Ser Tyr Asp Gly Ser Tyr Lys Tyr Lys Ala Asp Ser Met
    50                  55                  60

Lys Gly Arg Leu Thr Ile Ser Arg Asp Asn Ser Lys Asn Thr Leu Tyr
65                  70                  75                  80

Leu Glu Met Asn Ser Leu Thr Ala Glu Asp Thr Ala Val Tyr Tyr Cys
                85                  90                  95

Ala Arg Thr Ala Phe Phe Asn Ala Tyr Asp Phe Trp Gly Gln Gly Thr
            100                 105                 110

Leu Val Thr Val Ser Ser Ala Ser Thr Lys Gly Pro Ser Val Gly Gly
        115                 120                 125
```

-continued

```
Gly Gly Ser Gly Gly Gly Gly Ser Glu Ile Val Met Thr Gln Ser Pro
    130                 135                 140

Ala Thr Leu Ser Val Ser Pro Gly Glu Arg Ala Thr Leu Ser Cys Arg
145                 150                 155                 160

Ala Ser Gln Ser Val Arg Ser Asn Leu Ala Trp Tyr Gln Gln Lys Pro
                165                 170                 175

Gly Gln Ala Pro Arg Leu Leu Ile Tyr Ala Ala Ser Thr Arg Ala Thr
            180                 185                 190

Gly Ile Pro Ala Arg Phe Ser Gly Ser Gly Ser Gly Thr Glu Phe Thr
        195                 200                 205

Leu Thr Ile Ser Ser Leu Gln Ser Glu Asp Phe Ala Val Tyr Tyr Cys
    210                 215                 220

Gln Gln Tyr Asn Glu Trp Phe Arg Thr Ser Gly Gln Gly Thr Lys Val
225                 230                 235                 240

Glu Ile Lys Arg Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asn Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470
```

<210> SEQ ID NO 35
<211> LENGTH: 1121
<212> TYPE: DNA
<213> ORGANISM: Artificial Sequence
<220> FEATURE:
<223> OTHER INFORMATION: a fusion gene fragment encoding the fusion protein VhH-Fc

<400> SEQUENCE: 35

```
atggagaccg acaccctgct gctgtgggtg ctgctgctgt gggtgcccgg cagcaccggc     60
```

-continued

```
caggtgcagc tgcaggagtc tgggggaggc tcggtgcagg ctggagggtc tctgagactc    120

tcctgtgcag cctctgaata catctacagt agctactgca tggcctggtt ccgccaggct    180

ccagggaagg agcgcgaggg ggtcgcagtt attgggagtg atggtagcac aagctacgca    240

gactccgtga aaggccgatt caccatctcc aaagacaacg ccaagaacac tctgtatctg    300

caaatgaaca gcctgaaacc tgaggacact gccatgtact actgtgcggc catcggtggt    360

tactgctacc aaccacccta tgagtaccag tactggggcc aggggaccca ggtcaccgtc    420

tcccagaacc gaaaagcagc gacaagaccc acacctgccc cccctgcccc gcccccgagc    480

tgctgggcgg ccccagcgtg ttcctgttcc cccccaagcc caaggacacc ctgatgatca    540

gccgcacccc cgaggtgacc tgcgtggtgg tggacgtgag ccacgagaac cccgaggtga    600

agttcaactg gtacgtggac ggcgtggagg tgcacaacgc caagaccaag ccccgcgagg    660

agcagtacaa cagcacctac cgcgtggtga gcgtgctgac cgtgctgcac caggactggc    720

tgaacggcaa ggagtacaag tgcaaggtga gcaacaaggc cctgcccgcc cccatcgaga    780

agaccatcag caaggccaag ggccagcccc gcgagcccca ggtgtacacc ctgcccccca    840

gccgcgacga gctgaccaag aaccaggtga gcctgacctg cctggtgaag ggcttctacc    900

ccagcgacat cgccgtggag tgggagagca acggccagcc cgagaacaac tacaagacca    960

cccccccgt gctggacagc gacggcagct tcttcctgta cagcaagctg accgtggaca   1020

agagccgctg gcagcagggc aacgtgttca gctgcagcgt gatgcacgag gccctgcaca   1080

accactacac ccagaagagc ctgagcctga gccccggcaa g                       1121
```

<210> SEQ ID NO 36
<211> LENGTH: 354
<212> TYPE: PRT
<213> ORGANISM: Artificial Sequence
<220> FEATURE:
<223> OTHER INFORMATION: fusion protein VhH-Fc

<400> SEQUENCE: 36

```
Gln Val Gln Leu Gln Glu Ser Gly Gly Gly Ser Val Gln Ala Gly Gly
1               5                   10                  15

Ser Leu Arg Leu Ser Cys Ala Ala Ser Glu Tyr Ile Tyr Ser Ser Tyr
            20                  25                  30

Cys Met Ala Trp Phe Arg Gln Ala Pro Gly Lys Glu Arg Glu Gly Val
        35                  40                  45

Ala Val Ile Gly Ser Asp Gly Ser Thr Ser Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Ile Gly Gly Tyr Cys Tyr Gln Pro Pro Tyr Glu Tyr Gln Tyr Trp
            100                 105                 110

Gly Gln Gly Thr Gln Val Thr Val Ser Ser Glu Pro Lys Ser Ser Asp
        115                 120                 125

Lys Thr His Thr Cys Pro Pro Cys Pro Ala Pro Glu Leu Leu Gly Gly
    130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175
```

-continued

```
Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Asp Glu Leu Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys


<210> SEQ ID NO 37
<211> LENGTH: 15
<212> TYPE: PRT
<213> ORGANISM: Artificial Sequence
<220> FEATURE:
<223> OTHER INFORMATION: linker 1

<400> SEQUENCE: 37

Gly Gly Gly Gly Ser Gly Gly Gly Gly Ser Gly Gly Gly Gly Ser
1               5                   10                  15


<210> SEQ ID NO 38
<211> LENGTH: 582
<212> TYPE: PRT
<213> ORGANISM: Artificial Sequence
<220> FEATURE:
<223> OTHER INFORMATION: amino acid sequence of (IL10)2-Fc6

<400> SEQUENCE: 38

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110
```

```
Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Gly Gly Ser Gly Gly Gly Gly Ser Gly Gly Gly Gly Ser Ser
                165                 170                 175

Pro Gly Gln Gly Thr Gln Ser Glu Asn Ser Cys Thr His Phe Pro Gly
            180                 185                 190

Asn Leu Pro Asn Met Leu Arg Asp Leu Arg Asp Ala Phe Ser Arg Val
        195                 200                 205

Lys Thr Phe Phe Gln Met Lys Asp Gln Leu Asp Asn Leu Leu Leu Lys
    210                 215                 220

Glu Ser Leu Leu Glu Asp Phe Lys Gly Tyr Leu Gly Cys Gln Ala Leu
225                 230                 235                 240

Ser Glu Met Ile Gln Phe Tyr Leu Glu Glu Val Met Pro Gln Ala Glu
                245                 250                 255

Asn Gln Asp Pro Asp Ile Lys Ala His Val Asn Ser Leu Gly Glu Asn
            260                 265                 270

Leu Lys Thr Leu Arg Leu Arg Leu Arg Arg Cys His Arg Phe Leu Pro
        275                 280                 285

Cys Glu Asn Lys Ser Lys Ala Val Glu Gln Val Lys Asn Ala Phe Asn
    290                 295                 300

Lys Leu Gln Glu Lys Gly Ile Tyr Lys Ala Met Ser Glu Phe Asp Ile
305                 310                 315                 320

Phe Ile Asn Tyr Ile Glu Ala Tyr Met Thr Met Lys Ile Arg Asn Gly
                325                 330                 335

Gly Gly Gly Ser Gly Gly Gly Gly Ser Gly Gly Gly Gly Ser Glu Pro
            340                 345                 350

Lys Ser Ser Asp Lys Thr His Thr Cys Pro Pro Cys Pro Ala Pro Glu
        355                 360                 365

Leu Leu Gly Gly Pro Ser Val Phe Leu Phe Pro Pro Lys Pro Lys Asp
    370                 375                 380

Thr Leu Met Ile Ser Arg Thr Pro Glu Val Thr Cys Val Val Val Asp
385                 390                 395                 400

Val Ser His Glu Asp Pro Glu Val Lys Phe Asn Trp Tyr Val Asp Gly
                405                 410                 415

Val Glu Val His Asn Ala Lys Thr Lys Pro Arg Glu Glu Gln Tyr Asn
            420                 425                 430

Ser Thr Tyr Arg Val Val Ser Val Leu Thr Val Leu His Gln Asp Trp
        435                 440                 445

Leu Asn Gly Lys Glu Tyr Lys Cys Lys Val Ser Asn Lys Ala Leu Pro
    450                 455                 460

Ala Pro Ile Glu Lys Thr Ile Ser Lys Ala Lys Gly Gln Pro Arg Glu
465                 470                 475                 480

Pro Gln Val Tyr Thr Leu Pro Pro Ser Arg Asp Glu Leu Thr Lys Asn
                485                 490                 495

Gln Val Ser Leu Ser Cys Gly Val Lys Gly Phe Tyr Pro Ser Asp Ile
            500                 505                 510

Ala Val Glu Trp Glu Ser Asn Gly Gln Pro Glu Asn Asn Tyr Lys Thr
        515                 520                 525

Thr Pro Pro Val Leu Asp Ser Asp Gly Ser Phe Lys Leu Ala Ser Lys
```

-continued

```
    530                 535                 540

Leu Thr Val Asp Lys Ser Arg Trp Gln Gln Gly Asn Val Phe Ser Cys
545                 550                 555                 560

Ser Val Met His Glu Ala Leu His Asn His Tyr Thr Gln Lys Ser Leu
                565                 570                 575

Ser Leu Ser Pro Gly Lys
            580
```

<210> SEQ ID NO 39
<211> LENGTH: 1746
<212> TYPE: DNA
<213> ORGANISM: Artificial Sequence
<220> FEATURE:
<223> OTHER INFORMATION: gene of (IL10)2-Fc6

<400> SEQUENCE: 39

```
agccccggcc agggcacaca gtccgagaac agctgcaccc actttcccgg caacctgcct      60
aacatgctga gggacctgag ggacgccttc agcagggtga agaccttctt ccagatgaag     120
gaccagctgg ataacctgct gctgaaggag agcctgctgg aggacttcaa gggctacctg     180
ggctgccagg ccctgagcga gatgatccag ttctacctgg aggaggtgat gccccaggcc     240
gagaaccagg accccgacat caaggcccac gtgaacagcc tgggcgagaa cctgaagacc     300
ctgaggctga ggctgaggag gtgccacagg ttcctgccct gtgagaacaa atccaaggcc     360
gtggagcagg tgaagaacgc cttcaacaag ctgcaggaaa agggcatcta caaggccatg     420
agcgagttcg acatctttat caactatatc gaggcctaca tgacaatgaa gatcaggaac     480
ggcggcggcg gcagcggggg cggcggcagc ggaggaggcg gcagcagccc cggccagggc     540
acacagtccg agaacagctg cacccacttt cccggcaacc tgcctaacat gctgagggac     600
ctgagggacg ccttcagcag ggtgaagacc ttcttccaga tgaaggacca gctggataac     660
ctgctgctga aggagagcct gctggaggac ttcaagggct acctgggctg ccaggccctg     720
agcgagatga tccagttcta cctggaggag gtgatgcccc aggccgagaa ccaggacccc     780
gacatcaagg cccacgtgaa cagcctgggc gagaacctga agaccctgag gctgaggctg     840
aggaggtgcc acaggttcct gccctgtgag aacaaatcca aggccgtgga gcaggtgaag     900
aacgccttca acaagctgca ggaaaagggc atctacaagg ccatgagcga gttcgacatc     960
tttatcaact atatcgaggc ctacatgaca atgaagatca ggaacggcgg cggcggcagc    1020
gggggcggcg gcagcggagg aggcggcagc gagcctaagt ccagcgacaa gacccacacc    1080
tgcccccctt gccccgctcc ggaactcctg ggcggaccgt cagtcttcct cttcccccca    1140
aaacccaagg acaccctcat gatctcccgg acccctgagg tcacatgcgt ggtggtggac    1200
gtgagccacg aagaccctga ggtcaagttc aactggtacg tggacggcgt ggaggtgcat    1260
aatgccaaga caaagccgcg ggaggagcag tacaacagca cgtaccgtgt ggtcagcgtc    1320
ctcaccgtcc tgcaccagga ctggctgaat ggcaaggagt acaagtgcaa ggtctccaac    1380
aaagccctcc cagcccccat cgagaaaacc atctccaaag ccaaagggca gccccgagaa    1440
ccacaggtgt acaccctgcc cccatcccgg gatgagctga ccaagaacca ggtcagcctg    1500
agttgcgggg tcaaaggctt ctatcccagc gacatcgccg tggagtggga gagcaatggg    1560
cagccggaga acaactacaa gaccacgcct cccgtgttgg actccgacgg ctccttcaag    1620
ctcgccagca agctcaccgt ggacaagagc aggtggcagc aggggaacgt cttctcatgc    1680
tccgtgatgc atgaggctct gcacaaccac tacacgcaga agagcctctc cctgtctccg    1740
```

-continued ggtaaa 1746

<210> SEQ ID NO 40
<211> LENGTH: 407
<212> TYPE: PRT
<213> ORGANISM: Artificial Sequence
<220> FEATURE:
<223> OTHER INFORMATION: amino acid sequence of IL10-Fc

<400> SEQUENCE: 40

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Gly Gly Ser Gly Gly Gly Gly Ser Gly Gly Gly Gly Ser Glu
                165                 170                 175

Pro Lys Ser Ser Asp Lys Thr His Thr Cys Pro Pro Cys Pro Ala Pro
            180                 185                 190

Glu Leu Leu Gly Gly Pro Ser Val Phe Leu Phe Pro Pro Lys Pro Lys
        195                 200                 205

Asp Thr Leu Met Ile Ser Arg Thr Pro Glu Val Thr Cys Val Val Val
    210                 215                 220

Asp Val Ser His Glu Asp Pro Glu Val Lys Phe Asn Trp Tyr Val Asp
225                 230                 235                 240

Gly Val Glu Val His Asn Ala Lys Thr Lys Pro Arg Glu Glu Gln Tyr
                245                 250                 255

Asn Ser Thr Tyr Arg Val Val Ser Val Leu Thr Val Leu His Gln Asp
            260                 265                 270

Trp Leu Asn Gly Lys Glu Tyr Lys Cys Lys Val Ser Asn Lys Ala Leu
        275                 280                 285

Pro Ala Pro Ile Glu Lys Thr Ile Ser Lys Ala Lys Gly Gln Pro Arg
    290                 295                 300

Glu Pro Gln Val Tyr Thr Leu Pro Pro Ser Arg Asp Glu Leu Thr Lys
305                 310                 315                 320

Asn Gln Val Ser Leu Thr Cys Leu Val Lys Gly Phe Tyr Pro Ser Asp
                325                 330                 335

Ile Ala Val Glu Trp Glu Ser Asn Gly Gln Pro Glu Asn Asn Tyr Lys
            340                 345                 350

Thr Thr Pro Pro Val Leu Asp Ser Asp Gly Ser Phe Phe Leu Tyr Ser
```

```
        355                 360                 365

Lys Leu Thr Val Asp Lys Ser Arg Trp Gln Gln Gly Asn Val Phe Ser
    370                 375                 380

Cys Ser Val Met His Glu Ala Leu His Asn His Tyr Thr Gln Lys Ser
385                 390                 395                 400

Leu Ser Leu Ser Pro Gly Lys
                405
```

<210> SEQ ID NO 41
<211> LENGTH: 1221
<212> TYPE: DNA
<213> ORGANISM: Artificial Sequence
<220> FEATURE:
<223> OTHER INFORMATION: gene of IL10-Fc

<400> SEQUENCE: 41

```
agccccggcc agggcacaca gtccgagaac agctgcaccc actttcccgg caacctgcct     60

aacatgctga gggacctgag ggacgccttc agcagggtga agaccttctt ccagatgaag    120

gaccagctgg ataacctgct gctgaaggag agcctgctgg aggacttcaa gggctacctg    180

ggctgccagg ccctgagcga gatgatccag ttctacctgg aggaggtgat gccccaggcc    240

gagaaccagg accccgacat caaggcccac gtgaacagcc tgggcgagaa cctgaagacc    300

ctgaggctga ggctgaggag gtgccacagg ttcctgccct gtgagaacaa atccaaggcc    360

gtggagcagg tgaagaacgc cttcaacaag ctgcaggaaa agggcatcta caaggccatg    420

agcgagttcg acatctttat caactatatc gaggcctaca tgacaatgaa gatcaggaac    480

ggcggcggcg gcagcggggg cggcggcagc ggaggaggcg gcagcgagcc taagtccagc    540

gacaagaccc acacctgccc cccttgcccc gctccggaac tcctgggcgg accgtcagtc    600

ttcctcttcc ccccaaaacc caaggacacc ctcatgatct cccggacccc tgaggtcaca    660

tgcgtggtgg tggacgtgag ccacgaagac cctgaggtca agttcaactg gtacgtggac    720

ggcgtggagg tgcataatgc caagacaaag ccgcgggagg agcagtacaa cagcacgtac    780

cgtgtggtca gcgtcctcac cgtcctgcac caggactggc tgaatggcaa ggagtacaag    840

tgcaaggtct ccaacaaagc cctcccagcc cccatcgaga aaaccatctc caaagccaaa    900

gggcagcccc gagaaccaca ggtgtacacc ctgcccccat cccgggatga gctgaccaag    960

aaccaggtca gcctgacctg cctggtcaaa ggcttctatc ccagcgacat cgccgtggag   1020

tgggagagca atgggcagcc ggagaacaac tacaagacca cgcctcccgt gttggactcc   1080

gacggctcct tcttcctcta cagcaagctc accgtggaca agagcaggtg gcagcagggg   1140

aacgtcttct catgctccgt gatgcatgag gctctgcaca accactacac gcagaagagc   1200

ctctccctgt ctccgggtaa a                                             1221
```

<210> SEQ ID NO 42
<211> LENGTH: 681
<212> TYPE: DNA
<213> ORGANISM: Artificial Sequence
<220> FEATURE:
<223> OTHER INFORMATION: gene of Fc9

<400> SEQUENCE: 42

```
gacaaaactc acacatgccc accgtgccca gctccggaac tcctgggcgg accgtcagtc     60

ttcctcttcc ccccaaaacc caaggacacc ctcatgatct cccggacccc tgaggtcaca    120

tgcgtggtgg tggacgtgag ccacgaagac cctgaggtca agttcaactg gtacgtggac    180
```

-continued

```
ggcgtggagg tgcataatgc caagacaaag ccgcgggagg agcagtacaa cagcacgtac    240

cgtgtggtca gcgtcctcac cgtcctgcac caggactggc tgaatggcaa ggagtacaag    300

tgcaaggtct ccaacaaagc cctcccagcc cccatcgaga aaaccatctc caaagccaaa    360

gggcagcccc gagaaccaca ggtgtacacc ctgcccccaa gtcgggatga gctgaccaag    420

aaccaggtca gcctgtggtg cctggtcaaa ggcttctatc ccagcgacat cgccgtggag    480

tgggagagca atgggcagcc ggagaacaac tacaagacca cgcctcccgt gttggactcc    540

gacggctcct tcttcctcta cagcgcgctc accgtggaca agagcaggtg gcagcagggg    600

aacgtcttct catgctccgt gatgcatgag gctctgcaca accactacac gcagaagagc    660

ctctccctgt ctccgggtaa a                                              681
```

<210> SEQ ID NO 43
<211> LENGTH: 214
<212> TYPE: PRT
<213> ORGANISM: Artificial Sequence
<220> FEATURE:
<223> OTHER INFORMATION: amino acid sequence of Erb-LC

<400> SEQUENCE: 43

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 44
<211> LENGTH: 642
<212> TYPE: DNA
<213> ORGANISM: Artificial Sequence
<220> FEATURE:
<223> OTHER INFORMATION: gene of Erb-LC

<400> SEQUENCE: 44

```
gacatcctgc tgacccagag ccccgtgatc ctgagcgtga gccccggcga gcgcgtgagc      60

ttcagctgcc gcgccagcca gagcatcggc accaacatcc actggtacca gcagcgcacc     120

aacggcagcc cccgcctgct gatcaagtac gccagcgaga gcatcagcgg catccccagc     180

cgcttcagcg gcagcggcag cggcaccgac ttcaccctga gcatcaacag cgtggagagc     240

gaggacatcg ccgactacta ctgccagcag aacaacaact ggcccaccac cttcggcgcc     300

ggcaccaagc tggagctgaa gcgcaccgtg gccgccccca gcgtgttcat cttccccccc     360

agcgacgagc agctgaagag cggcaccgcc agcgtggtgt gcctgctgaa caacttctac     420

cccgcgagg ccaaggtgca gtggaaggtg gacaacgccc tgcagagcgg caacagccag      480

gagagcgtga ccgagcagga cagcaaggac agcacctaca gcctgagcag caccctgacc     540

ctgagcaagg ccgactacga gaagcacaag gtgtacgcct gcgaggtgac ccaccagggc     600

ctgagcagcc ccgtgaccaa gagcttcaac cgcggcgagt gc                        642
```

<210> SEQ ID NO 45
<211> LENGTH: 449
<212> TYPE: PRT
<213> ORGANISM: Artificial Sequence
<220> FEATURE:
<223> OTHER INFORMATION: amino acid sequences of Erb-Fc9

<400> SEQUENCE: 45

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

-continued

```
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Ala Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 46
<211> LENGTH: 1347
<212> TYPE: DNA
<213> ORGANISM: Artificial Sequence
<220> FEATURE:
<223> OTHER INFORMATION: gene of Erb-Fc9

<400> SEQUENCE: 46

```
caggtgcagc tgaagcagag cggccccggc ctggtgcagc ccagccagag cctgagcatc     60

acctgcaccg tgagcggctt cagcctgacc aactacggcg tgcactgggt gcgccagagc    120

cccggcaagg gcctggagtg gctgggcgtg atctggagcg gcggcaacac cgactacaac    180

accccttca ccagccgcct gagcatcaac aaggacaaca gcaagagcca ggtgttcttc    240

aagatgaaca gcctgcagag caacgacacc gccatctact actgcgcccg cgccctgacc    300

tactacgact acgagttcgc ctactggggc cagggcaccc tggtgaccgt gagcgccgcc    360

agcactaagg ggccctctgt gtttccactc gccccttcta gcaaaagcac ttccggagga    420

actgccgctc tgggctgtct ggtgaaagat tacttccccg aaccagtcac tgtgtcatgg    480

aactctggag cactgacatc tggagttcac acctttcctg ctgtgctgca gagttctgga    540

ctgtactccc tgtcatctgt ggtcaccgtg ccatcttcat ctctggggac ccagacctac    600

atctgtaacg tgaaccacaa accctccaac acaaaagtgg acaaacgagt cgaaccaaaa    660

tcttgtgaca aaacccacac atgcccaccg tgcccagctc cggaactcct gggcggaccg    720

tcagtcttcc tcttcccccc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900
```

-continued acgtaccgtg tggtcagcgt cctcaccgtc ctgcaccagg actggctgaa tggcaaggag 960
tacaagtgca aggtctccaa caaagccctc ccagccccca tcgagaaaac catctccaaa 1020
gccaaagggc agccccgaga accacaggtg tacaccctgc ccccaagtcg ggatgagctg 1080
accaagaacc aggtcagcct gtggtgcctg gtcaaaggct tctatcccag cgacatcgcc 1140
gtggagtggg agagcaatgg gcagccggag aacaactaca agaccacgcc tcccgtgttg 1200
gactccgacg gctccttctt cctctacagc gcgctcaccg tggacaagag caggtggcag 1260
caggggaacg tcttctcatg ctccgtgatg catgaggctc tgcacaacca ctacacgcag 1320
aagagcctct ccctgtctcc gggtaaa 1347

<210> SEQ ID NO 47
<211> LENGTH: 582
<212> TYPE: PRT
<213> ORGANISM: Artificial Sequence
<220> FEATURE:
<223> OTHER INFORMATION: amino acid sequence of (IL10)2-Fc

<400> SEQUENCE: 47

Ser Pro Gly Gln Gly Thr Gln Ser Glu Asn Ser Cys Thr His Phe Pro
1 5 10 15

Gly Asn Leu Pro Asn Met Leu Arg Asp Leu Arg Asp Ala Phe Ser Arg
20 25 30

Val Lys Thr Phe Phe Gln Met Lys Asp Gln Leu Asp Asn Leu Leu Leu
35 40 45

Lys Glu Ser Leu Leu Glu Asp Phe Lys Gly Tyr Leu Gly Cys Gln Ala
50 55 60

Leu Ser Glu Met Ile Gln Phe Tyr Leu Glu Glu Val Met Pro Gln Ala
65 70 75 80

Glu Asn Gln Asp Pro Asp Ile Lys Ala His Val Asn Ser Leu Gly Glu
85 90 95

Asn Leu Lys Thr Leu Arg Leu Arg Leu Arg Arg Cys His Arg Phe Leu
100 105 110

Pro Cys Glu Asn Lys Ser Lys Ala Val Glu Gln Val Lys Asn Ala Phe
115 120 125

Asn Lys Leu Gln Glu Lys Gly Ile Tyr Lys Ala Met Ser Glu Phe Asp
130 135 140

Ile Phe Ile Asn Tyr Ile Glu Ala Tyr Met Thr Met Lys Ile Arg Asn
145 150 155 160

Gly Gly Gly Gly Ser Gly Gly Gly Gly Ser Gly Gly Gly Gly Ser Ser
165 170 175

Pro Gly Gln Gly Thr Gln Ser Glu Asn Ser Cys Thr His Phe Pro Gly
180 185 190

Asn Leu Pro Asn Met Leu Arg Asp Leu Arg Asp Ala Phe Ser Arg Val
195 200 205

Lys Thr Phe Phe Gln Met Lys Asp Gln Leu Asp Asn Leu Leu Leu Lys
210 215 220

Glu Ser Leu Leu Glu Asp Phe Lys Gly Tyr Leu Gly Cys Gln Ala Leu
225 230 235 240

Ser Glu Met Ile Gln Phe Tyr Leu Glu Glu Val Met Pro Gln Ala Glu
245 250 255

Asn Gln Asp Pro Asp Ile Lys Ala His Val Asn Ser Leu Gly Glu Asn
260 265 270

Leu Lys Thr Leu Arg Leu Arg Leu Arg Arg Cys His Arg Phe Leu Pro

-continued

```
        275                 280                 285

Cys Glu Asn Lys Ser Lys Ala Val Glu Gln Val Lys Asn Ala Phe Asn
    290                 295                 300

Lys Leu Gln Glu Lys Gly Ile Tyr Lys Ala Met Ser Glu Phe Asp Ile
305                 310                 315                 320

Phe Ile Asn Tyr Ile Glu Ala Tyr Met Thr Met Lys Ile Arg Asn Gly
                325                 330                 335

Gly Gly Gly Ser Gly Gly Gly Gly Ser Gly Gly Gly Gly Ser Glu Pro
            340                 345                 350

Lys Ser Ser Asp Lys Thr His Thr Cys Pro Pro Cys Pro Ala Pro Glu
        355                 360                 365

Leu Leu Gly Gly Pro Ser Val Phe Leu Phe Pro Pro Lys Pro Lys Asp
    370                 375                 380

Thr Leu Met Ile Ser Arg Thr Pro Glu Val Thr Cys Val Val Val Asp
385                 390                 395                 400

Val Ser His Glu Asp Pro Glu Val Lys Phe Asn Trp Tyr Val Asp Gly
                405                 410                 415

Val Glu Val His Asn Ala Lys Thr Lys Pro Arg Glu Glu Gln Tyr Asn
            420                 425                 430

Ser Thr Tyr Arg Val Val Ser Val Leu Thr Val Leu His Gln Asp Trp
        435                 440                 445

Leu Asn Gly Lys Glu Tyr Lys Cys Lys Val Ser Asn Lys Ala Leu Pro
    450                 455                 460

Ala Pro Ile Glu Lys Thr Ile Ser Lys Ala Lys Gly Gln Pro Arg Glu
465                 470                 475                 480

Pro Gln Val Tyr Thr Leu Pro Pro Ser Arg Asp Glu Leu Thr Lys Asn
                485                 490                 495

Gln Val Ser Leu Thr Cys Leu Val Lys Gly Phe Tyr Pro Ser Asp Ile
            500                 505                 510

Ala Val Glu Trp Glu Ser Asn Gly Gln Pro Glu Asn Asn Tyr Lys Thr
        515                 520                 525

Thr Pro Pro Val Leu Asp Ser Asp Gly Ser Phe Phe Leu Tyr Ser Lys
    530                 535                 540

Leu Thr Val Asp Lys Ser Arg Trp Gln Gln Gly Asn Val Phe Ser Cys
545                 550                 555                 560

Ser Val Met His Glu Ala Leu His Asn His Tyr Thr Gln Lys Ser Leu
                565                 570                 575

Ser Leu Ser Pro Gly Lys
            580


<210> SEQ ID NO 48
<211> LENGTH: 1746
<212> TYPE: DNA
<213> ORGANISM: Artificial Sequence
<220> FEATURE:
<223> OTHER INFORMATION: gene of (IL10)2-Fc

<400> SEQUENCE: 48

agccccggcc agggcacaca gtccgagaac agctgcaccc actttcccgg caacctgcct      60

aacatgctga gggacctgag ggacgccttc agcagggtga agaccttctt ccagatgaag     120

gaccagctgg ataacctgct gctgaaggag agcctgctgg aggacttcaa gggctacctg     180

ggctgccagg ccctgagcga gatgatccag ttctacctgg aggaggtgat gccccaggcc     240

gagaaccagg accccgacat caaggcccac gtgaacagcc tgggcgagaa cctgaagacc     300
```

```
ctgaggctga ggctgaggag gtgccacagg ttcctgccct gtgagaacaa atccaaggcc    360

gtggagcagg tgaagaacgc cttcaacaag ctgcaggaaa agggcatcta caaggccatg    420

agcgagttcg acatctttat caactatatc gaggcctaca tgacaatgaa gatcaggaac    480

ggcggcggcg gcagcggggg cggcggcagc ggaggaggcg gcagcagccc cggccagggc    540

acacagtccg agaacagctg cacccacttt cccggcaacc tgcctaacat gctgagggac    600

ctgagggacg ccttcagcag ggtgaagacc ttcttccaga tgaaggacca gctggataac    660

ctgctgctga aggagagcct gctggaggac ttcaagggct acctgggctg ccaggccctg    720

agcgagatga tccagttcta cctggaggag gtgatgcccc aggccgagaa ccaggacccc    780

gacatcaagg cccacgtgaa cagcctgggc gagaacctga agaccctgag gctgaggctg    840

aggaggtgcc acaggttcct gccctgtgag aacaaatcca aggccgtgga gcaggtgaag    900

aacgccttca acaagctgca ggaaaagggc atctacaagg ccatgagcga gttcgacatc    960

tttatcaact atatcgaggc ctacatgaca atgaagatca ggaacggcgg cggcggcagc   1020

gggggcggcg gcagcggagg aggcggcagc gagcctaagt ccagcgacaa gacccacacc   1080

tgcccccctt gccccgctcc ggaactcctg ggcggaccgt cagtcttcct cttcccccca   1140

aaacccaagg acaccctcat gatctcccgg acccctgagg tcacatgcgt ggtggtggac   1200

gtgagccacg aagaccctga ggtcaagttc aactggtacg tggacggcgt ggaggtgcat   1260

aatgccaaga caaagccgcg ggaggagcag tacaacagca cgtaccgtgt ggtcagcgtc   1320

ctcaccgtcc tgcaccagga ctggctgaat ggcaaggagt acaagtgcaa ggtctccaac   1380

aaagccctcc cagcccccat cgagaaaacc atctccaaag ccaaagggca gccccgagaa   1440

ccacaggtgt acaccctgcc cccatcccgg gatgagctga ccaagaacca ggtcagcctg   1500

acctgcctgg tcaaaggctt ctatcccagc gacatcgccg tggagtggga gagcaatggg   1560

cagccggaga acaactacaa gaccacgcct cccgtgttgg actccgacgg ctccttcttc   1620

ctctacagca agctcaccgt ggacaagagc aggtggcagc aggggaacgt cttctcatgc   1680

tccgtgatgc atgaggctct gcacaaccac tacacgcaga agagcctctc cctgtctccg   1740

ggtaaa                                                              1746
```

<210> SEQ ID NO 49
<211> LENGTH: 160
<212> TYPE: PRT
<213> ORGANISM: Artificial Sequence
<220> FEATURE:
<223> OTHER INFORMATION: amino acid sequence of IL10

<400> SEQUENCE: 49

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
```

```
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160


<210> SEQ ID NO 50
<211> LENGTH: 480
<212> TYPE: DNA
<213> ORGANISM: Artificial Sequence
<220> FEATURE:
<223> OTHER INFORMATION: gene of IL10

<400> SEQUENCE: 50

agccccggcc agggcacaca gtccgagaac agctgcaccc actttcccgg caacctgcct      60

aacatgctga gggacctgag ggacgccttc agcagggtga agaccttctt ccagatgaag     120

gaccagctgg ataacctgct gctgaaggag agcctgctgg aggacttcaa gggctacctg     180

ggctgccagg ccctgagcga gatgatccag ttctacctgg aggaggtgat gccccaggcc     240

gagaaccagg accccgacat caaggcccac gtgaacagcc tgggcgagaa cctgaagacc     300

ctgaggctga ggctgaggag gtgccacagg ttcctgccct gtgagaacaa atccaaggcc     360

gtggagcagg tgaagaacgc cttcaacaag ctgcaggaaa agggcatcta caaggccatg     420

agcgagttcg acatctttat caactatatc gaggcctaca tgacaatgaa gatcaggaac     480


<210> SEQ ID NO 51
<211> LENGTH: 335
<212> TYPE: PRT
<213> ORGANISM: Artificial Sequence
<220> FEATURE:
<223> OTHER INFORMATION: amino acid sequences of (IL10)2

<400> SEQUENCE: 51

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Gly Gly Ser Gly Gly Gly Gly Ser Gly Gly Gly Gly Ser Ser
                165                 170                 175
```

```
Pro Gly Gln Gly Thr Gln Ser Glu Asn Ser Cys Thr His Phe Pro Gly
            180                 185                 190

Asn Leu Pro Asn Met Leu Arg Asp Leu Arg Asp Ala Phe Ser Arg Val
        195                 200                 205

Lys Thr Phe Phe Gln Met Lys Asp Gln Leu Asp Asn Leu Leu Leu Lys
    210                 215                 220

Glu Ser Leu Leu Glu Asp Phe Lys Gly Tyr Leu Gly Cys Gln Ala Leu
225                 230                 235                 240

Ser Glu Met Ile Gln Phe Tyr Leu Glu Glu Val Met Pro Gln Ala Glu
                245                 250                 255

Asn Gln Asp Pro Asp Ile Lys Ala His Val Asn Ser Leu Gly Glu Asn
            260                 265                 270

Leu Lys Thr Leu Arg Leu Arg Leu Arg Arg Cys His Arg Phe Leu Pro
        275                 280                 285

Cys Glu Asn Lys Ser Lys Ala Val Glu Gln Val Lys Asn Ala Phe Asn
    290                 295                 300

Lys Leu Gln Glu Lys Gly Ile Tyr Lys Ala Met Ser Glu Phe Asp Ile
305                 310                 315                 320

Phe Ile Asn Tyr Ile Glu Ala Tyr Met Thr Met Lys Ile Arg Asn
                325                 330                 335
```

<210> SEQ ID NO 52
<211> LENGTH: 1005
<212> TYPE: DNA
<213> ORGANISM: Artificial Sequence
<220> FEATURE:
<223> OTHER INFORMATION: gene of (IL10)2

<400> SEQUENCE: 52

```
agccccggcc agggcacaca gtccgagaac agctgcaccc actttcccgg caacctgcct     60

aacatgctga gggacctgag ggacgccttc agcagggtga agaccttctt ccagatgaag    120

gaccagctgg ataacctgct gctgaaggag agcctgctgg aggacttcaa gggctacctg    180

ggctgccagg ccctgagcga gatgatccag ttctacctgg aggaggtgat gccccaggcc    240

gagaaccagg accccgacat caaggcccac gtgaacagcc tgggcgagaa cctgaagacc    300

ctgaggctga ggctgaggag gtgccacagg ttcctgccct gtgagaacaa atccaaggcc    360

gtggagcagg tgaagaacgc cttcaacaag ctgcaggaaa agggcatcta caaggccatg    420

agcgagttcg acatctttat caactatatc gaggcctaca tgacaatgaa gatcaggaac    480

ggcggcggcg gcagcggggg cggcggcagc ggaggaggcg gcagcagccc cggccagggc    540

acacagtccg agaacagctg cacccacttt cccggcaacc tgcctaacat gctgagggac    600

ctgagggacg ccttcagcag ggtgaagacc ttcttccaga tgaaggacca gctggataac    660

ctgctgctga aggagagcct gctggaggac ttcaagggct acctgggctg ccaggccctg    720

agcgagatga tccagttcta cctggaggag gtgatgcccc aggccgagaa ccaggacccc    780

gacatcaagg cccacgtgaa cagcctgggc gagaacctga agaccctgag gctgaggctg    840

aggaggtgcc acaggttcct gccctgtgag aacaaatcca aggccgtgga gcaggtgaag    900

aacgccttca acaagctgca ggaaaagggc atctacaagg ccatgagcga gttcgacatc    960

tttatcaact atatcgaggc ctacatgaca atgaagatca ggaac                   1005
```

<210> SEQ ID NO 53
<211> LENGTH: 407
<212> TYPE: PRT

<213> ORGANISM: Artificial Sequence
<220> FEATURE:
<223> OTHER INFORMATION: amino acid sequence of IL10-Fc6

<400> SEQUENCE: 53

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Gly Gly Ser Gly Gly Gly Gly Ser Gly Gly Gly Gly Ser Glu
                165                 170                 175

Pro Lys Ser Ser Asp Lys Thr His Thr Cys Pro Pro Cys Pro Ala Pro
            180                 185                 190

Glu Leu Leu Gly Gly Pro Ser Val Phe Leu Phe Pro Pro Lys Pro Lys
        195                 200                 205

Asp Thr Leu Met Ile Ser Arg Thr Pro Glu Val Thr Cys Val Val Val
    210                 215                 220

Asp Val Ser His Glu Asp Pro Glu Val Lys Phe Asn Trp Tyr Val Asp
225                 230                 235                 240

Gly Val Glu Val His Asn Ala Lys Thr Lys Pro Arg Glu Glu Gln Tyr
                245                 250                 255

Asn Ser Thr Tyr Arg Val Val Ser Val Leu Thr Val Leu His Gln Asp
            260                 265                 270

Trp Leu Asn Gly Lys Glu Tyr Lys Cys Lys Val Ser Asn Lys Ala Leu
        275                 280                 285

Pro Ala Pro Ile Glu Lys Thr Ile Ser Lys Ala Lys Gly Gln Pro Arg
    290                 295                 300

Glu Pro Gln Val Tyr Thr Leu Pro Pro Ser Arg Asp Glu Leu Thr Lys
305                 310                 315                 320

Asn Gln Val Ser Leu Ser Cys Gly Val Lys Gly Phe Tyr Pro Ser Asp
                325                 330                 335

Ile Ala Val Glu Trp Glu Ser Asn Gly Gln Pro Glu Asn Asn Tyr Lys
            340                 345                 350

Thr Thr Pro Pro Val Leu Asp Ser Asp Gly Ser Phe Lys Leu Ala Ser
        355                 360                 365

Lys Leu Thr Val Asp Lys Ser Arg Trp Gln Gln Gly Asn Val Phe Ser
    370                 375                 380

Cys Ser Val Met His Glu Ala Leu His Asn His Tyr Thr Gln Lys Ser
```

385 390 395 400

Leu Ser Leu Ser Pro Gly Lys
405

<210> SEQ ID NO 54
<211> LENGTH: 1221
<212> TYPE: DNA
<213> ORGANISM: Artificial Sequence
<220> FEATURE:
<223> OTHER INFORMATION: gene of IL10-Fc6

<400> SEQUENCE: 54
agccccggcc agggcacaca gtccgagaac agctgcaccc actttcccgg caacctgcct 60
aacatgctga gggacctgag ggacgccttc agcagggtga agaccttctt ccagatgaag 120
gaccagctgg ataacctgct gctgaaggag agcctgctgg aggacttcaa gggctacctg 180
ggctgccagg ccctgagcga gatgatccag ttctacctgg aggaggtgat gccccaggcc 240
gagaaccagg accccgacat caaggcccac gtgaacagcc tgggcgagaa cctgaagacc 300
ctgaggctga ggctgaggag gtgccacagg ttcctgccct gtgagaacaa atccaaggcc 360
gtggagcagg tgaagaacgc cttcaacaag ctgcaggaaa agggcatcta caaggccatg 420
agcgagttcg acatctttat caactatatc gaggcctaca tgacaatgaa gatcaggaac 480
ggcggcggcg gcagcggggg cggcggcagc ggaggaggcg gcagcgagcc taagtccagc 540
gacaagaccc acacctgccc cccttgcccc gctccggaac tcctgggcgg accgtcagtc 600
ttcctcttcc ccccaaaacc caaggacacc ctcatgatct cccggacccc tgaggtcaca 660
tgcgtggtgg tggacgtgag ccacgaagac cctgaggtca agttcaactg gtacgtggac 720
ggcgtggagg tgcataatgc caagacaaag ccgcgggagg agcagtacaa cagcacgtac 780
cgtgtggtca gcgtcctcac cgtcctgcac caggactggc tgaatggcaa ggagtacaag 840
tgcaaggtct ccaacaaagc cctcccagcc cccatcgaga aaaccatctc caaagccaaa 900
gggcagcccc gagaaccaca ggtgtatacc ctgcccccat cccgggatga gctgaccaag 960
aaccaggtca gcctgagttg cggggtcaaa ggcttctatc ccagcgacat cgccgtggag 1020
tgggagagca atgggcagcc ggagaacaac tacaagacca cgcctcccgt gttggactcc 1080
gacggctcct tcaagctcgc cagcaagctc accgtggaca agagcaggtg gcagcagggg 1140
aacgtcttct catgctccgt gatgcatgag gctctgcaca accactacac gcagaagagc 1200
ctctccctgt ctccgggtaa a 1221

<210> SEQ ID NO 55
<211> LENGTH: 582
<212> TYPE: PRT
<213> ORGANISM: Artificial Sequence
<220> FEATURE:
<223> OTHER INFORMATION: amino acid sequence of Fc6-(IL10)2

<400> SEQUENCE: 55

Glu Pro Lys Ser Ser Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

-continued

```
Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Ser Cys Gly Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Lys Leu Ala
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Gly Gly Gly Ser Gly Gly Gly
225                 230                 235                 240

Gly Ser Gly Gly Gly Gly Ser Ser Pro Gly Gln Gly Thr Gln Ser Glu
                245                 250                 255

Asn Ser Cys Thr His Phe Pro Gly Asn Leu Pro Asn Met Leu Arg Asp
            260                 265                 270

Leu Arg Asp Ala Phe Ser Arg Val Lys Thr Phe Phe Gln Met Lys Asp
        275                 280                 285

Gln Leu Asp Asn Leu Leu Leu Lys Glu Ser Leu Leu Glu Asp Phe Lys
    290                 295                 300

Gly Tyr Leu Gly Cys Gln Ala Leu Ser Glu Met Ile Gln Phe Tyr Leu
305                 310                 315                 320

Glu Glu Val Met Pro Gln Ala Glu Asn Gln Asp Pro Asp Ile Lys Ala
                325                 330                 335

His Val Asn Ser Leu Gly Glu Asn Leu Lys Thr Leu Arg Leu Arg Leu
            340                 345                 350

Arg Arg Cys His Arg Phe Leu Pro Cys Glu Asn Lys Ser Lys Ala Val
        355                 360                 365

Glu Gln Val Lys Asn Ala Phe Asn Lys Leu Gln Glu Lys Gly Ile Tyr
    370                 375                 380

Lys Ala Met Ser Glu Phe Asp Ile Phe Ile Asn Tyr Ile Glu Ala Tyr
385                 390                 395                 400

Met Thr Met Lys Ile Arg Asn Gly Gly Gly Gly Ser Gly Gly Gly Gly
                405                 410                 415

Ser Gly Gly Gly Gly Ser Ser Pro Gly Gln Gly Thr Gln Ser Glu Asn
            420                 425                 430

Ser Cys Thr His Phe Pro Gly Asn Leu Pro Asn Met Leu Arg Asp Leu
        435                 440                 445

Arg Asp Ala Phe Ser Arg Val Lys Thr Phe Phe Gln Met Lys Asp Gln
    450                 455                 460

Leu Asp Asn Leu Leu Leu Lys Glu Ser Leu Leu Glu Asp Phe Lys Gly
465                 470                 475                 480

Tyr Leu Gly Cys Gln Ala Leu Ser Glu Met Ile Gln Phe Tyr Leu Glu
```

-continued

```
                485                 490                 495

Glu Val Met Pro Gln Ala Glu Asn Gln Asp Pro Asp Ile Lys Ala His
            500                 505                 510

Val Asn Ser Leu Gly Glu Asn Leu Lys Thr Leu Arg Leu Arg Leu Arg
        515                 520                 525

Arg Cys His Arg Phe Leu Pro Cys Glu Asn Lys Ser Lys Ala Val Glu
    530                 535                 540

Gln Val Lys Asn Ala Phe Asn Lys Leu Gln Glu Lys Gly Ile Tyr Lys
545                 550                 555                 560

Ala Met Ser Glu Phe Asp Ile Phe Ile Asn Tyr Ile Glu Ala Tyr Met
                565                 570                 575

Thr Met Lys Ile Arg Asn
            580


<210> SEQ ID NO 56
<211> LENGTH: 1746
<212> TYPE: DNA
<213> ORGANISM: Artificial Sequence
<220> FEATURE:
<223> OTHER INFORMATION: gene of Fc6-(IL10)2

<400> SEQUENCE: 56

gagcctaagt ccagcgacaa gacccacacc tgcccccctt gccccgctcc ggaactcctg      60

ggcggaccgt cagtcttcct cttcccccca aaacccaagg acaccctcat gatctcccgg     120

acccctgagg tcacatgcgt ggtggtggac gtgagccacg aagaccctga ggtcaagttc     180

aactggtacg tggacggcgt ggaggtgcat aatgccaaga caaagccgcg ggaggagcag     240

tacaacagca cgtaccgtgt ggtcagcgtc ctcaccgtcc tgcaccagga ctggctgaat     300

ggcaaggagt acaagtgcaa ggtctccaac aaagccctcc cagcccccat cgagaaaacc     360

atctccaaag ccaaagggca gccccgagaa ccacaggtgt ataccctgcc cccatcccgg     420

gatgagctga ccaagaacca ggtcagcctg agttgcgggg tcaaaggctt ctatcccagc     480

gacatcgccg tggagtggga gagcaatggg cagccggaga acaactacaa gaccacgcct     540

cccgtgttgg actccgacgg ctccttcaag ctcgccagca agctcaccgt ggacaagagc     600

aggtggcagc aggggaacgt cttctcatgc tccgtgatgc atgaggctct gcacaaccac     660

tacacgcaga agagcctctc cctgtctccg ggtaaaggcg gcggcggcag cgggggcggc     720

ggcagcggag gaggcggcag cagccccggc cagggcacac agtccgagaa cagctgcacc     780

cactttcccg gcaacctgcc taacatgctg agggacctga gggacgcctt cagcagggtg     840

aagaccttct tccagatgaa ggaccagctg gataacctgc tgctgaagga gagcctgctg     900

gaggacttca agggctacct gggctgccag gccctgagcg agatgatcca gttctacctg     960

gaggaggtga tgccccaggc cgagaaccag gaccccgaca tcaaggccca cgtgaacagc    1020

ctgggcgaga acctgaagac cctgaggctg aggctgagga ggtgccacag gttcctgccc    1080

tgtgagaaca aatccaaggc cgtggagcag gtgaagaacg ccttcaacaa gctgcaggaa    1140

aagggcatct acaaggccat gagcgagttc gacatcttta tcaactatat cgaggcctac    1200

atgacaatga agatcaggaa cggcggcggc ggcagcgggg gcggcggcag cggaggaggc    1260

ggcagcagcc ccggccaggg cacacagtcc gagaacagct gcacccactt tcccggcaac    1320

ctgcctaaca tgctgaggga cctgagggac gccttcagca gggtgaagac cttcttccag    1380

atgaaggacc agctggataa cctgctgctg aaggagagcc tgctggagga cttcaagggc    1440

tacctgggct gccaggccct gagcgagatg atccagttct acctggagga ggtgatgccc    1500
```

caggccgaga accaggaccc cgacatcaag gcccacgtga acagcctggg cgagaacctg 1560
aagaccctga ggctgaggct gaggaggtgc cacaggttcc tgccctgtga gaacaaatcc 1620
aaggccgtgg agcaggtgaa gaacgccttc aacaagctgc aggaaaaggg catctacaag 1680
gccatgagcg agttcgacat ctttatcaac tatatcgagg cctacatgac aatgaagatc 1740
aggaac 1746

<210> SEQ ID NO 57
<211> LENGTH: 577
<212> TYPE: PRT
<213> ORGANISM: Artificial Sequence
<220> FEATURE:
<223> OTHER INFORMATION: amino acid sequence of (IL10)2-Fc9

<400> SEQUENCE: 57

Ser Pro Gly Gln Gly Thr Gln Ser Glu Asn Ser Cys Thr His Phe Pro
1 5 10 15

Gly Asn Leu Pro Asn Met Leu Arg Asp Leu Arg Asp Ala Phe Ser Arg
20 25 30

Val Lys Thr Phe Phe Gln Met Lys Asp Gln Leu Asp Asn Leu Leu Leu
35 40 45

Lys Glu Ser Leu Leu Glu Asp Phe Lys Gly Tyr Leu Gly Cys Gln Ala
50 55 60

Leu Ser Glu Met Ile Gln Phe Tyr Leu Glu Glu Val Met Pro Gln Ala
65 70 75 80

Glu Asn Gln Asp Pro Asp Ile Lys Ala His Val Asn Ser Leu Gly Glu
85 90 95

Asn Leu Lys Thr Leu Arg Leu Arg Leu Arg Arg Cys His Arg Phe Leu
100 105 110

Pro Cys Glu Asn Lys Ser Lys Ala Val Glu Gln Val Lys Asn Ala Phe
115 120 125

Asn Lys Leu Gln Glu Lys Gly Ile Tyr Lys Ala Met Ser Glu Phe Asp
130 135 140

Ile Phe Ile Asn Tyr Ile Glu Ala Tyr Met Thr Met Lys Ile Arg Asn
145 150 155 160

Gly Gly Gly Gly Ser Gly Gly Gly Gly Ser Gly Gly Gly Gly Ser Ser
165 170 175

Pro Gly Gln Gly Thr Gln Ser Glu Asn Ser Cys Thr His Phe Pro Gly
180 185 190

Asn Leu Pro Asn Met Leu Arg Asp Leu Arg Asp Ala Phe Ser Arg Val
195 200 205

Lys Thr Phe Phe Gln Met Lys Asp Gln Leu Asp Asn Leu Leu Leu Lys
210 215 220

Glu Ser Leu Leu Glu Asp Phe Lys Gly Tyr Leu Gly Cys Gln Ala Leu
225 230 235 240

Ser Glu Met Ile Gln Phe Tyr Leu Glu Glu Val Met Pro Gln Ala Glu
245 250 255

Asn Gln Asp Pro Asp Ile Lys Ala His Val Asn Ser Leu Gly Glu Asn
260 265 270

Leu Lys Thr Leu Arg Leu Arg Leu Arg Arg Cys His Arg Phe Leu Pro
275 280 285

Cys Glu Asn Lys Ser Lys Ala Val Glu Gln Val Lys Asn Ala Phe Asn
290 295 300

Lys Leu Gln Glu Lys Gly Ile Tyr Lys Ala Met Ser Glu Phe Asp Ile

```
305                 310                 315                 320

Phe Ile Asn Tyr Ile Glu Ala Tyr Met Thr Met Lys Ile Arg Asn Gly
                325                 330                 335

Gly Gly Gly Ser Gly Gly Gly Gly Ser Gly Gly Gly Gly Ser Asp Lys
            340                 345                 350

Thr His Thr Cys Pro Pro Cys Pro Ala Pro Glu Leu Leu Gly Gly Pro
        355                 360                 365

Ser Val Phe Leu Phe Pro Pro Lys Pro Lys Asp Thr Leu Met Ile Ser
    370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
        435                 440                 445

Tyr Lys Cys Lys Val Ser Asn Lys Ala Leu Pro Ala Pro Ile Glu Lys
    450                 455                 460

Thr Ile Ser Lys Ala Lys Gly Gln Pro Arg Glu Pro Gln Val Tyr Thr
465                 470                 475                 480

Leu Pro Pro Ser Arg Asp Glu Leu Thr Lys Asn Gln Val Ser Leu Trp
                485                 490                 495

Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
        515                 520                 525

Asp Ser Asp Gly Ser Phe Phe Leu Tyr Ser Ala Leu Thr Val Asp Lys
    530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

Lys
```

<210> SEQ ID NO 58
<211> LENGTH: 1731
<212> TYPE: DNA
<213> ORGANISM: Artificial Sequence
<220> FEATURE:
<223> OTHER INFORMATION: gene of (IL10)2-Fc9

<400> SEQUENCE: 58

```
agccccggcc agggcacaca gtccgagaac agctgcaccc actttcccgg caacctgcct      60

aacatgctga gggacctgag ggacgccttc agcagggtga agaccttctt ccagatgaag     120

gaccagctgg ataacctgct gctgaaggag agcctgctgg aggacttcaa gggctacctg     180

ggctgccagg ccctgagcga gatgatccag ttctacctgg aggaggtgat gccccaggcc     240

gagaaccagg accccgacat caaggcccac gtgaacagcc tgggcgagaa cctgaagacc     300

ctgaggctga ggctgaggag gtgccacagg ttcctgccct gtgagaacaa atccaaggcc     360

gtggagcagg tgaagaacgc cttcaacaag ctgcaggaaa agggcatcta caaggccatg     420

agcgagttcg acatctttat caactatatc gaggcctaca tgacaatgaa gatcaggaac     480

ggcggcggcg gcagcggggg cggcggcagc ggaggaggcg gcagcagccc cggccagggc     540
```

-continued

```
acacagtccg agaacagctg cacccacttt cccggcaacc tgcctaacat gctgagggac    600
ctgagggacg ccttcagcag ggtgaagacc ttcttccaga tgaaggacca gctggataac    660
ctgctgctga aggagagcct gctggaggac ttcaagggct acctgggctg ccaggccctg    720
agcgagatga tccagttcta cctggaggag gtgatgcccc aggccgagaa ccaggacccc    780
gacatcaagg cccacgtgaa cagcctgggc gagaacctga agaccctgag gctgaggctg    840
aggaggtgcc acaggttcct gccctgtgag aacaaatcca aggccgtgga gcaggtgaag    900
aacgccttca acaagctgca ggaaaagggc atctacaagg ccatgagcga gttcgacatc    960
tttatcaact atatcgaggc ctacatgaca atgaagatca ggaacggcgg cggcggcagc   1020
gggggcggcg gcagcggagg aggcggcagc gacaaaactc acacatgccc accgtgccca   1080
gctccggaac tcctgggcgg accgtcagtc ttcctcttcc ccccaaaacc caaggacacc   1140
ctcatgatct cccggacccc tgaggtcaca tgcgtggtgg tggacgtgag ccacgaagac   1200
cctgaggtca agttcaactg gtacgtggac ggcgtggagg tgcataatgc caagacaaag   1260
ccgcgggagg agcagtacaa cagcacgtac cgtgtggtca gcgtcctcac cgtcctgcac   1320
caggactggc tgaatggcaa ggagtacaag tgcaaggtct ccaacaaagc cctcccagcc   1380
cccatcgaga aaaccatctc caaagccaaa gggcagcccc gagaaccaca ggtgtacacc   1440
ctgcccccaa gtcgggatga gctgaccaag aaccaggtca gcctgtggtg cctggtcaaa   1500
ggcttctatc ccagcgacat cgccgtggag tgggagagca atgggcagcc ggagaacaac   1560
tacaagacca cgcctcccgt gttggactcc gacggctcct tcttcctcta cagcgcgctc   1620
accgtggaca agagcaggtg gcagcagggg aacgtcttct catgctccgt gatgcatgag   1680
gctctgcaca accactacac gcagaagagc ctctccctgt ctccgggtaa a            1731
```

<210> SEQ ID NO 59
<211> LENGTH: 681
<212> TYPE: DNA
<213> ORGANISM: Artificial Sequence
<220> FEATURE:
<223> OTHER INFORMATION: gene of Fc6

<400> SEQUENCE: 59

```
gacaagaccc acacctgccc cccttgcccc gctccggaac tcctgggcgg accgtcagtc     60
ttcctcttcc ccccaaaacc caaggacacc ctcatgatct cccggacccc tgaggtcaca    120
tgcgtggtgg tggacgtgag ccacgaagac cctgaggtca agttcaactg gtacgtggac    180
ggcgtggagg tgcataatgc caagacaaag ccgcgggagg agcagtacaa cagcacgtac    240
cgtgtggtca gcgtcctcac cgtcctgcac caggactggc tgaatggcaa ggagtacaag    300
tgcaaggtct ccaacaaagc cctcccagcc cccatcgaga aaaccatctc caaagccaaa    360
gggcagcccc gagaaccaca ggtgtatacc ctgcccccat cccgggatga gctgaccaag    420
aaccaggtca gcctgagttg cggggtcaaa ggcttctatc ccagcgacat cgccgtggag    480
tgggagagca atgggcagcc ggagaacaac tacaagacca cgcctcccgt gttggactcc    540
gacggctcct tcaagctcgc cagcaagctc accgtggaca agagcaggtg gcagcagggg    600
aacgtcttct catgctccgt gatgcatgag gctctgcaca accactacac gcagaagagc    660
ctctccctgt ctccgggtaa a                                              681
```

PROTEINACEOUS HETERODIMER AND USE THEREOF

CROSS-REFERENCE TO RELATED APPLICATIONS

This application is a National Stage Application and claims priority under 35 U.S.C. 371 to Patent Cooperation Treaty application PCT/CN2018/107099, filed Sep. 21, 2018, which claims the benefit of Patent Cooperation Treaty application PCT/CN2017/103199, filed Sep. 25, 2017, priority is claimed to these applications and the disclosures of these prior applications are considered part of the disclosure of this application and to the extent allowed the entire contents of the aforementioned applications are incorporated herein.

SEQUENCE LISTING

This application incorporates by reference in its entirety the Sequence Listing entitled "2020 03 17 262790 465171 Sequence Listing ST25.txt", is 133,582 bytes in size and was created on Mar. 17, 2020, and filed electronically herewith.

BACKGROUND

Although immune responses against tumor antigens can be detected (Disis et al. (1997) J. Clin. Oncol. 15: 3363-3367), malignant cells causing diseases often fail to elicit an immune response that leads to rejection. Studies have demonstrated that it is possible to enhance the immunogenicity of tumor cells by introducing immunoregulatory molecules such as cytokines and costimulatory molecules into them. However, the expression and stability of the immunoregulatory molecules introduced are often far from satisfactory. Immunoregulators, such as cytokines, produced by cells of the immune system can, directly or indirectly, activate the cells of the adaptive immune response and can play an important role in eliciting protective antitumor immunity. The innate immune system can be triggered by bacterial products or "danger" signals that lead to the release of proinflammatory cytokines, such as IFN-α, TNF-α, and interleukins.

Multiple studies have shown that immunoregulators (such as interleukins) may be useful in exerting antitumor effects in both animal models and cancer patients. However, interleukins have a relatively short serum half-life in the body. For example, the half-life of IL10 in mice as measured by in vitro bioassay or by efficacy in the septic shock model system (see Smith et al., Cellular Immunology 173: 207-214 (1996)) is about 2 to 6 hours. A loss of interleukin activity may be due to several factors, including renal clearance, proteolytic degradation and monomerization in the blood stream.

As such, there is a considerable need for long-acting immunoregulators, which could be produced with relatively high yield at industrial-scale and would have a relatively long half-life in vivo to be useful in treating disorders or diseases related with hyper proliferation of cells and/or tissues, e.g., various neoplasms, different types of cancer, and/or tumors. In addition, the yield of such a product shall be sufficiently high to avoid complicated purification process and/or to reduce the risks associated with undesired impurities.

SUMMARY

The present disclosure addresses such a need and provides related advantages as well. The present disclosure encompasses proteinaceous heterodimers useful in inhibiting tumor growth, and compositions, medicaments and/or kits comprising the proteinaceous heterodimers. In addition, the present disclosure provides protein mixtures comprising said proteinaceous heterodimers and with little (if any) undesired impurities (such as undesired protein homodimers or protein aggregates). The disclosure also provides methods to produce the proteinaceous heterodimers or protein mixtures, as well as pharmaceutical uses of the proteinaceous heterodimers and/or protein mixtures in inhibiting tumor growth, including but not limited to treatment of cancers.

In one aspect, the present disclosure provides a proteinaceous heterodimer comprising a first monomeric member and a second monomeric member different from said first monomeric member, wherein the first monomeric member comprises a first Fc subunit, the second monomeric member comprises a second Fc subunit, and the first monomeric member associates with the second monomeric member to form the heterodimer through complexation of the first Fc subunit with the second Fc subunit; wherein the proteinaceous heterodimer further comprises one or more interleukins fused to the first Fc subunit and/or the second Fc subunit; and wherein the proteinaceous heterodimer does not comprise any antibody heavy chain variable region or any antibody light chain variable region exhibiting binding specificity to a tumor antigen.

In some embodiments, the proteinaceous heterodimer according to the present disclosure, wherein the one or more interleukins is fused to an amino-terminal amino acid and/or a carboxy-terminal amino acid of the first Fc subunit and/or the second Fc subunit.

In some embodiments, the proteinaceous heterodimer according to the present disclosure, which comprises two or more interleukins, and wherein the two or more interleukins form one or more interleukin dimers, with each interleukin dimer comprising two interleukins fused to each other.

In some embodiments, the proteinaceous heterodimer according to any one of the present disclosure, wherein at least one of the one or more interleukins is IL10.

In some embodiments, the proteinaceous heterodimer according to any one of the present disclosure, wherein the one or more interleukin dimers comprise at least one IL10 dimer, and the IL10 dimer comprises two IL10.

In some embodiments, the proteinaceous heterodimer according to any one of the present disclosure, wherein the first Fc subunit and/or said second Fc subunit is from an IgG molecule. In some embodiments, the proteinaceous heterodimer according to the present disclosure, wherein the IgG is a human IgG1.

In some embodiments, the proteinaceous heterodimer according to any one of the present disclosure, wherein the first Fc subunit is different from the second Fc subunit, and the first and/or second Fc subunit comprises a modification promoting heterodimerization between the first Fc subunit and the second Fc subunit.

In some embodiments, the proteinaceous heterodimer according to the present disclosure, wherein the first Fc subunit comprises a first modification, the second Fc subunit comprises a second modification, and the first modification and the second modification comprise an amino acid substitution at group of positions selected from any following groups: 1) the first modification: Y349 and T366; and the second modification: D356, T366, L368, Y407 and F405; 2) the first modification: Y349, T366 and F405; and the second modification: D356, T366, L368 and Y407; 3) the first modification: Y349, T366 and K409; and the second modification: D356, T366, L368, Y407 and F405; 4) the first modification: Y349, T366, F405, K360 and Q347; and the second modification: D356, T366, L368, Y407 and Q347; 5) the first modification: Y349, T366, F405 and Q347; and the second modification: D356, T366, L368, Y407, K360 and Q347; 6) the first modification: Y349, T366, K409, K360 and Q347; and the second modification: D356, T366, L368, Y407, F405 and Q347; 7) the first modification: Y349, T366, K409 and Q347; and the second modification: D356, T366, L368, Y407, F405, K360 and Q347; 8) the first modification: T366, K409 and K392; and the second modification: T366, L368, Y407, D399 and F405; 9) the first modification: T366 and K409; and the second modification: T366, L368, Y407 and F405; 10) the first modification: T366, K409 and Y349; and the second modification: T366, L368, Y407, F405 and E357; 11) the first modification: T366, K409, Y349 and 5354; and the second modification: T366, L368, Y407, F405 and E357; 12) the first modification: T366 and F405; and the second modification: T366, L368, Y407 and K409; 13) the first modification: T366, F405 and D399; and the second modification: T366, L368, Y407, K409 and K392; 14) the first modification: T366, F405 and Y349; and the second modification: T366, L368, Y407, K409 and E357; 15) the first modification: T366, F405, Y349 and S354; and the second modification: T366, L368, Y407, K409 and E357; wherein the position of the amino acid is determined according to the EU index of the KABAT number.

In some embodiments, the proteinaceous heterodimer according to any one of the present disclosure, wherein at least one of the one or more interleukins is fused to an amino-terminal amino acid of the second Fc subunit.

In some embodiments, the proteinaceous heterodimer according to the present disclosure, wherein in the second monomeric member, at least two of the one or more interleukins are fused to each other to form an interleukin dimer, and the interleukin dimer is further fused to the amino-terminal amino acid of the second Fc subunit.

In some embodiments, the proteinaceous heterodimer according to any one of the present disclosure, wherein in the second monomeric member, at least two of the one or more interleukins are fused to each other to form an interleukin dimer, and the interleukin dimer is further fused to the carboxyl-terminal amino acid of the second Fc subunit.

In some embodiments, the proteinaceous heterodimer according to any one of the present disclosure, wherein the first monomeric member does not comprise any interleukin.

In some embodiments, the proteinaceous heterodimer according to any one of the present disclosure, wherein the first monomeric member consists of the first Fc subunit.

In some embodiments, the proteinaceous heterodimer according to any one of the present disclosure, wherein at least one of the one or more interleukins is fused to an amino-terminal amino acid of the first Fc subunit.

In some embodiments, the proteinaceous heterodimer according to the present disclosure, wherein in the first monomeric member, at least two of the one or more interleukins are fused to each other to form an interleukin dimer, and the interleukin dimer is further fused to the amino-terminal amino acid of the first Fc subunit.

In some embodiments, the proteinaceous heterodimer according to any one of the present disclosure, wherein the second monomeric member does not comprise any interleukin.

In some embodiments, the proteinaceous heterodimer according to any one of the present disclosure, wherein the second monomeric member consists of the second Fc subunit.

In another aspect, the present disclosure provides an isolated nucleic acid or isolated nucleic acids encoding the proteinaceous heterodimer according to any one of the present disclosure.

In another aspect, the present disclosure provides a vector or vectors comprising the isolated nucleic acid or isolated nucleic acids according to the present disclosure.

In another aspect, the present disclosure provides an isolated host cell comprising the isolated nucleic acid or isolated nucleic acids according to the present disclosure or the vector or vectors according to the present disclosure.

In another aspect, the present disclosure provides a protein mixture, comprising: 1) the proteinaceous heterodimer according to any one of the present disclosure; 2) a first homodimer formed by two identical copies of the first monomeric member according to any one of the present disclosure; and 3) a second homodimer formed by two identical copies of the second monomeric member according to any one of the present disclosure; wherein a percentage of said proteinaceous heterodimer in the protein mixture is at least 50%.

In another aspect, the present disclosure provides a pharmaceutical composition comprising the proteinaceous heterodimer according to any one of the present disclosure, or the protein mixture according to the present disclosure and optionally a pharmaceutically acceptable excipient.

In another aspect, the present disclosure provides a use of the proteinaceous heterodimer according to any one of the present disclosure, or the protein mixture according to the present disclosure in the manufacture of a medicament and/or a kit for inhibiting growth of a tumor or a tumor cell and/or for treating cancer in a subject in need thereof.

In another aspect, the present disclosure provides a method for producing a proteinaceous heterodimer according to any one of the present disclosure, comprising (i) culturing the host cell of the present disclosure under conditions to effect expression of the proteinaceous heterodimer, and (ii) harvesting the expressed proteinaceous heterodimer or a protein mixture comprising said proteinaceous heterodimer.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1:
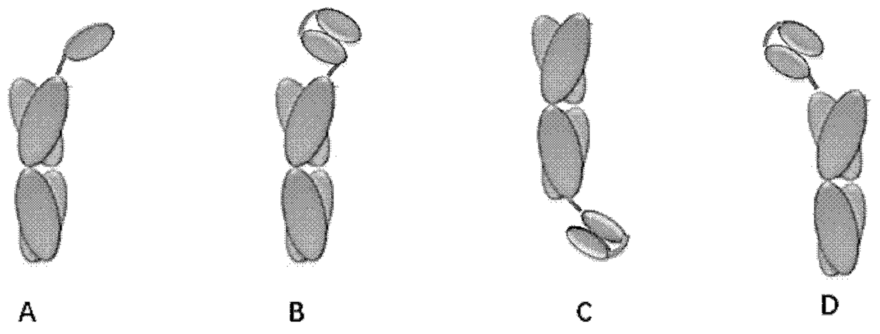
FIGS. 1A-1D illustrate examples of the proteinaceous heterodimers according to the present application.

Before the embodiments of the disclosure are described, it is to be understood that such embodiments are provided by way of example only, and that various alternatives to the embodiments of the disclosure described herein may be employed in practicing the disclosure. Numerous variations, changes, and substitutions will now occur to those skilled in the art without departing from the disclosure.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. In case of conflict, the patent specification, including definitions, will control. In addition, the materials, methods, and examples are illustrative only and not intended to be limiting. Numerous variations, changes, and substitutions will now occur to those skilled in the art without departing from the disclosure.

The singular form “a,” “an” and “the,” as used herein, generally include plural references unless the context clearly dictates otherwise.

The term “proteinaceous,” as used herein, generally refers to a material or molecule that is of, relating to, resembling, or being a polypeptide or a protein. For example, a proteinaceous heterodimer of the present disclosure may be a heterodimer protein, or a heterodimer comprising two or more polypeptides.

The term “heterodimer,” as used herein, generally refers to a molecule (e.g. a proteinaceous molecule) composed of two different members. The two members of a heterodimer may differ in structure, function, activity and/or composition. For example, the two different members may comprise polypeptides differing in the order, number, or kind of amino acid residues forming these polypeptides. Each of the two different members of a heterodimer may independently comprise one, two or more units, polypeptide chains, or moieties.

The term “targeting moiety,” as used herein, generally refers to a molecule, complex or aggregate, that binds specifically, selectively or preferentially to a target molecule, cell, particle, tissue or aggregate. For example, a targeting moiety may be an antibody, antigen-binding antibody fragment, bispecific antibody or other antibody-based molecule or compound. Other examples of targeting moieties may include, but are not limited to, aptamers, avimers, receptor-binding ligands, nucleic acids, biotin-avidin binding pairs, binding peptides or proteins, etc. The terms “targeting moiety” and “binding moiety” are used interchangeably herein.

The term “tumor antigen,” as used herein, generally refers to an antigenic substance produced in or by tumor cells, which may have an ability to trigger an immune response in a host. For example, a tumor antigen may be a protein, a polypeptide, a peptide, or a fragment thereof, which constitutes part of a tumor cell and is capable of inducing tumor-specific cytotoxic T lymphocytes. A tumor antigen peptide may be a peptide that is generated as a result of degradation of the tumor antigen in a tumor cell and can induce or activate tumor-specific cytotoxic T lymphocytes upon being expressed on cell surface by binding to an HLA molecule. In some embodiments, the term “tumor antigen” may also refer to biomolecules (e.g., proteins, carbohydrates, glycoproteins, etc.) that are exclusively or preferentially or differentially expressed on a cancer cell and/or are found in association with a cancer cell and thereby provide targets preferential or specific to the cancer. For example, the preferential expression can be preferential expression as compared to any other cell in the organism, or preferential expression within a particular area of the organism (e.g. within a particular organ or tissue).

The terms “tumor antigen epitope” and “tumor antigen determinant” are used interchangeably herein and generally refer to the site of an amino acid sequence present in a tumor antigen that induces tumor-specific cytotoxic T lymphocytes.

The term “expression yield” as used in the context of proteinaceous heterodimers herein, generally refers to an amount of a proteinaceous heterodimer being produced in functional form upon expression, e.g., when expressed by a host cell.

The term “dimerization sequence” as used herein, generally refers to an amino acid sequence capable of forming a dimer, or undergoing dimerization. In some embodiments, a dimer is a heterodimer formed by two different members. In some cases, the two different members of a heterodimer may comprise different dimerization sequences.

The term “heterodimerization” as used herein, generally refers to the process of forming a heterodimer between two different members (e.g., two different polypeptides), such as through complexation, association, or aggregation, with or without formation of covalent bonds between the two different members.

The term “covalent bond” as used herein, generally refers to a chemical bond formed between atoms by the sharing of electrons. For example, a covalent bond may be polar or non-polar. In some embodiments, a covalent bond is a disulfide bond.

The term “non-covalent pairwise affinity” as used herein, generally refers to that dimerization sequences or heterodimerization sequences capable of binding each other via non-covalent interaction, e.g., via ion pairs, hydrogen bonds, dipole-dipole interactions, charge transfer interactions, n-n interactions, cation-n-electron interactions, van der Waals interactions and disperse interactions, hydrophobic (lipophilic) interactions, complex formation (e.g., complex formation of transition metal cations), or a combination of these interactions.

The term “linker,” as used herein, generally refers to a synthetic amino acid sequence that connects or links two polypeptide sequences, e.g., that link two polypeptide domains. A linker may connect two amino acid sequences via peptide bonds. In some embodiments, a linker of the present disclosure connects a biologically active moiety to a second moiety in a linear sequence.

The terms “polypeptide” “peptide” and “protein” are used interchangeably herein to refer to polymers of amino acids of any length. The polymer may be linear or branched, it may comprise modified amino acids, and it may be interrupted by non-amino acids. The terms also encompass an amino acid polymer that has been modified, for example, by disulfide bond formation, glycosylation, lipidation, acetylation, phosphorylation, or any other manipulation, such as conjugation with a labeling component. The terms may apply to amino acid polymers in which one or more amino acid residue is an artificial chemical analogue of a corresponding naturally occurring amino acid, as well as to naturally occurring amino acid polymers. The terms may also include variants on the traditional peptide linkage joining the amino acids making up the polypeptide. For example, the “peptides”, “polypeptides” and “proteins” may be chains of amino acids whose alpha carbons are linked through peptide bonds. The terminal amino acid at one end of the chain (amino terminal) therefore may have a free amino group, while the terminal amino acid at the other end of the chain (carboxy terminal) may have a free carboxyl group. As used herein, the term “amino terminus” (abbreviated N-terminus) generally refers to the free a-amino group on an amino acid at the amino terminal of a peptide or to the a-amino group (amino group when participating in a peptide bond) of an amino acid at any other location within the peptide. Similarly, the term “carboxy terminus” generally refers to the free carboxyl group on the carboxy terminus of a peptide or the carboxyl group of an amino acid at any other location within the peptide. Peptides may also include essentially any poly-amino acid including, but not limited to peptide mimetics such as amino acids joined by a ether as opposed to an amide bond.

The term “amino acid” as used herein, generally refers to either natural and/or unnatural or synthetic amino acids, including but not limited to, the D or L optical isomers or both, amino acid analogs and peptidomimetics. Standard single or three letter codes are used to designate amino acids.

The term “natural L-amino acid” as used herein, generally refers to the L optical isomer forms of glycine (G), proline (P), alanine (A), valine (V), leucine (L), isoleucine (I), methionine (M), cysteine (C), phenylalanine (F), tyrosine (Y), tryptophan (W), histidine (H), lysine (K), arginine (R), glutamine (Q), asparagine (N), glutamic acid (E), aspartic acid (D), serine (S), and threonine (T).

The term “non-naturally occurring” as used herein, generally refers to polypeptide or polynucleotide sequences that do not have a counterpart to, are not complementary to, or do not have a high degree of homology with a wild-type or naturally-occurring sequence (e.g., those found in a subject). For example, a non-naturally occurring polypeptide or fragment may share less than 99%, 98%, 95%, 90%, 80%, 70%, 60%, 50% or even less amino acid sequence identity as compared to a natural sequence when suitably aligned. Alternatively, a non-naturally occurring polypeptide or fragment may share more than 99%, 98%, 95%, 90%, 80%, 70%, 60%, 50% or even more amino acid sequence identity as compared to a natural sequence when suitably aligned.

The terms “hydrophilic” and “hydrophobic,” as used herein, generally refer to the degree of affinity that a substance has with water. A hydrophilic substance has a strong affinity for water, tending to dissolve in, mix with, or be wetted by water, while a hydrophobic substance substantially lacks affinity for water, tending to repel and not absorb water and tending not to dissolve in or mix with or be wetted by water. Amino acids can be characterized based on their hydrophobicity. A number of scales have been developed. An example is a scale developed by Levitt, M, et al., J Mol Biol (1976) 104: 59, which is listed in Hopp, T P, et al., Proc Natl Acad Sci U S A (1981) 78: 3824. Examples of “hydrophilic amino acids” are arginine, lysine, threonine, alanine, asparagine, and glutamine. Of particular interest are the hydrophilic amino acids aspartate, glutamate, and serine, and glycine. Examples of “hydrophobic amino acids” are tryptophan, tyrosine, phenylalanine, methionine, leucine, isoleucine, and valine.

The term “fragment” when used in the context of a proteinaceous molecule (e.g., a polypeptide or a protein), generally refers to a truncated form of a native biologically active protein that may or may not retain a portion of the therapeutic and/or biological activity.

The term “variant” when used in the context of a proteinaceous molecule (e.g., a polypeptide or a protein), generally refers to a proteinaceous molecule with sequence homology to the native biologically active protein that retains at least a portion of the therapeutic and/or biological activity of the biologically active protein. For example, a variant protein may share at least 60%, 65%, 70%, 75%, 80%, 85%, 90%, 95%, 96%, 97%, 98% or 99% amino acid sequence identity compared with the reference biologically active protein. In some embodiments, the “variant” may include proteins modified deliberately, as for example, by site directed mutagenesis, synthesis of the encoding gene, insertions, or accidentally through mutations.

The terms “conjugated”, “linked”, “fused”, and “fusion” are used interchangeably herein, and generally refer to the joining together of two or more chemical elements, sequences or components, e.g., by means including chemical conjugation or recombinant means. For example, a promoter or enhancer is operably linked to a coding sequence if it effects the transcription of the sequence. Generally, “operably linked” means that the DNA sequences being linked are contiguous, and in reading phase or in-frame. An “in-frame fusion” refers to the joining of two or more open reading frames (ORFs) to form a continuous longer ORF, in a manner that maintains the correct reading frame of the original ORFs. Thus, the resulting “fusion polypeptide” is a single protein containing two or more fragments that correspond to polypeptides encoded by the original ORFs (which segments are not normally so joined in nature). The “fusion site” refers to the sequence where the two or more fragments are joined together. In some cases, the fusion site can be a sequence that is identical to sequences in the two or more fragments being joined. In some cases, the fusion site can further comprise a gap segment that is not identical to either of the sequences of the two or more fragments being joined.

In the context of polypeptides, a “linear sequence” or a “sequence” is an order of amino acids in a polypeptide in an amino to carboxyl terminus direction in which residues next to each other in the sequence are contiguous in the primary structure of the polypeptide. A “partial sequence” is a linear sequence forming part of a polypeptide that is known to comprise additional residues in one or both directions.

The terms “polynucleotides”, “nucleic acids”, “nucleotides” and “oligonucleotides” are used interchangeably herein, and they generally refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The terms "gene" and "gene fragment" are used interchangeably herein and generally refer to a polynucleotide containing at least one open reading frame that is capable of encoding a particular protein after being transcribed and translated. A gene or gene fragment may be genomic or cDNA, as long as the polynucleotide contains at least one open reading frame, which may cover the entire coding region or a segment thereof A "fusion gene" is a gene composed of at least two heterologous polynucleotides that are linked together.

The term "antibody" as used herein, generally refers to a protein comprising one or more polypeptides substantially encoded by immunoglobulin genes or fragments of immunoglobulin genes. The immunoglobulin genes may include the kappa, lambda, alpha, gamma, delta, epsilon and mu constant region genes, as well as myriad immunoglobulin variable region genes. As used herein, light chains may be classified as either kappa or lambda. Heavy chains may be classified as gamma, mu, alpha, delta, or epsilon, which in turn define the immunoglobulin classes, IgG, IgM, IgA, IgD and IgE, respectively. An antibody as used in the present disclosure may have a structural unit comprising a tetramer. Each tetramer may be composed of two identical pairs of polypeptide chains, each pair having one "light" (about 25 KD) and one "heavy" chain (about 50-70 KD). The N-terminus of each chain may define a variable region of about 100 to 110 or more amino acids primarily responsible for antigen recognition. The terms "light chain variable region" (VL) and "heavy chain variable region" (VH), as used herein, generally refer to these regions of the light and heavy chains respectively. Antibodies may exist as intact immunoglobulins or as a number of well characterized fragments produced by digestion with various peptidases or expressed de novo. Thus, for example, pepsin may digest an antibody below the disulfide linkages in the hinge region to produce F(ab)'2 (a dimer of Fab which itself is a light chain joined to VH-CH1 by a disulfide bond). The F(ab)'2 may be reduced under mild conditions to break the disulfide linkage in the hinge region thereby converting the (Fab')2 dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of ordinary skill in the art will appreciate that such Fab' fragments may be synthesized de novo either chemically or by utilizing recombinant DNA methodology. Thus, the term antibody, as used herein, may also include antibody fragments either produced by the modification of whole antibodies or synthesized de novo using recombinant DNA methodologies, including, but are not limited to, Fab'2, IgG, IgM, IgA, IgE, scFv, dAb, nanobodies, unibodies, and diabodies. In some embodiments, the antibodies include, but are not limited to Fab'2, IgG, IgM, IgA, IgE, and single chain antibodies, for example, single chain Fv (scFv) antibodies in which a variable heavy and a variable light chain are joined together (directly or through a peptide linker) to form a continuous polypeptide.

The term "antigen-binding site" or "binding portion," as used herein, generally refers to a part of an antibody that participates in antigen binding. An antigen binding site may be formed by amino acid residues of the N-terminal variable ("V") regions of a heavy ("H") chain and/or a light ("L") chain. Three highly divergent stretches within the V regions of the heavy and light chains are referred to as "hypervariable regions" which are interposed between more conserved flanking stretches known as "framework regions" or "FRs". Thus, the term "FR," as used herein, generally refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three-dimensional space to form an antigen binding "surface". This surface may mediate recognition and binding of the target antigen. The three hypervariable regions of each of the heavy and light chains are referred to as "complementarity determining regions" or "CDRs" and are characterized, for example by Kabat et al. *Sequences of proteins of immunological interest*, $4^{th}$ ed. U.S. Dept. Health and Human Services, Public Health Services, Bethesda, Md. (1987).

The term "host cell" as used herein, generally includes an individual cell, a cell line or cell culture which can be or has been a recipient for the subject plasmids or vectors, comprise the polynucleotide of the present disclosure, or express the proteinaceous heterodimer (e.g. heterodimer protein) of the present disclosure. Host cells may include progeny of a single host cell. The progeny may not necessarily be completely identical (in morphology or in genomic of total DNA complement) to the original parent cell due to natural, accidental, or deliberate mutation. A host cell may include cells transfected in vitro with a vector of the present disclosure. A host cell may be a bacterial cell (e.g., *E. coli*), a yeast cell or other eukaryotic cells, e.g., a COS cell, a Chinese hamster ovary (CHO) cell, a HeLa cell, a HEK293 cell, a COS-1 cell, an NSO cell, or a myeloma cell. In some embodiments, a host cell is a mammalian cell. In some embodiments, the mammalian cell is a HEK293 cell.

The term "vector" as used herein, generally refers to a nucleic acid molecule capable of self-replicating in an appropriate host, which transfers an inserted nucleic acid molecule into and/or between host cells. The term may include vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions. An "expression vector" is a polynucleotide which, when introduced into an appropriate host cell, can be transcribed and translated into a polypeptide(s). An "expression system" usually connotes a suitable host cell comprising an expression vector that can function to yield a desired expression product.

The term "effective amount" or "therapeutically effective amount" refers to an amount of a composition (e.g., a proteinaceous heterodimer described herein) that is sufficient to effect the intended application, including but not limited to disease treatment. The therapeutically effective amount may vary depending upon the intended application (e.g., in vitro or in vivo), or the subject and disease condition being treated, e.g., the weight and age of the subject, the severity of the disease condition, the manner of administration and the like, which can readily be determined by one of ordinary skill in the art. The term may also apply to a dose that will induce a particular response in target cells, e.g. target gene induction, proliferation, and/or apoptosis. The specific dose will vary depending on the particular compounds chosen, the dosing regimen to be followed, whether it is administered in combination with other compounds, timing of administration, the tissue to which it is administered, and the physical delivery system in which it is carried.

The terms "treatment" or "treating" or "palliating" or "ameliorating" is used interchangeably herein, and refer to an approach for obtaining beneficial or desired results including but not limited to a therapeutic benefit and/or a prophylactic benefit. As used herein, therapeutic benefit generally refers to eradication or reduced severity of the underlying disorder being treated. Also, a therapeutic benefit is achieved with the eradication, reduced severity or reduced incidence of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

The term "therapeutic effect" as used herein, generally encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "agent" or "biologically active agent" as used herein, generally refers to a biological, pharmaceutical, or chemical compound or other moieties. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

The term "cell proliferation" as used herein, generally refers to a phenomenon by which the cell number has changed as a result of division. For example, cell proliferation may result in an increase in number of cells. This term also encompasses cell growth by which the cell morphology has changed (e.g., increased in size) consistent with a proliferative signal.

The term "in vivo" as used herein, generally refers to an event that takes place in a subject's body.

The term "in vitro" as used herein, generally refers to an event that takes places outside of a subject's body. For example, an in vitro assay encompasses any assay conducted outside of a subject. In vitro assays encompass cell-based assays in which dead or living cells are employed. In vitro assays also encompass a cell-free assay in which no intact cells are employed.

The term "interleukin" as used herein, generally refers to a secreted protein or a signaling molecule capable of promoting the development and differentiation of T and/or B lymphocytes and/or hematopoietic cells. An interleukin may be synthesized by helper CD4 T lymphocytes, as well as through monocytes, macrophages, and endothelial cells. As used herein, an interleukin (IL) may include IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and/or IL-36. As used herein, the term "interleukin" may include full length interleukins, or a fragment (e.g., a truncated form) or variant thereof substantially maintaining the biological activities of a corresponding wild-type interleukin (e.g., having a biological activity that is at least 80%, at least 90%, at least 95%, at least 98%, at least 99%, or even at least 100% of the biological activity of a corresponding wild-type interleukin). An interleukin, as used herein, may be from any mammalian species. In some embodiments, the interleukin is from a species selected from the group consisting of human, horse, cattle, murine, pig, rabbit, cat, dog, rat, goat, sheep, and non-human primate. In some embodiments, the interleukin can be in a mutated form, for example, with increased or decreased affinity to its receptors. In specific embodiments, the interleukin can be a super IL-2 (also known as sIL2, see *Nature* 484, 529-533, 26 Apr. 2012), which may be obtained by modifying IL-2 to increase its binding affinity for IL-2R13. Mutations in sIL-2 are principally in the core of the cytokine, and molecular dynamics simulations indicated that the evolved mutations stabilized IL-2, reducing the flexibility of a helix in the IL-2R13 binding site, into an optimized receptor-binding conformation resembling that when bound to CD25. Compared to IL-2, sIL-2 induced superior expansion of cytotoxic T cells, leading to improved anti-tumor responses in vivo, and elicited proportionally less expansion of T regulatory cells and reduced pulmonary edema.

The term "subject" as used herein, generally refers to a human or non-human animal, including, but not limited to, a cat, dog, horse, pig, cow, sheep, goat, rabbit, mouse, rat, or monkey.

The term "inhibition of growth and/or proliferation," when used with cancer cells, generally refers to decrease in the growth rate and/or proliferation rate of a cancer cell. For example, this may include death of a cancer cell (e.g. via apoptosis). In some embodiments, this term may also refer to inhibiting the growth and/or proliferation of a solid tumor and/or inducing tumor size reduction or elimination of the tumor.

The term "a cancer cell surface marker" or "a cancer cell associated marker," as used herein, generally refers to biomolecules such as proteins, carbohydrates, glycoproteins, and the like that are exclusively or preferentially or differentially expressed on a cancer cell and/or are found to be associated with a cancer cell and thereby provide targets preferential or specific to the cancer. In some embodiments, the preferential expression can be preferential expression as compared to any other cell in the organism, or preferential expression within a particular area of the organism (e.g. within a particular organ or tissue).

The term "monomeric member" as used herein, generally refers to a polypeptide, subunit, or moiety, which is present as a monomer, and is a component/subunit of the proteinaceous heterodimer.

The term "Fc subunit" as used herein, generally refers to the carboxyl terminal portion of an immunoglobulin heavy chain constant region, or an analog or portion thereof capable of binding an Fc receptor. As is known, each immunoglobulin heavy chain constant region comprises four or five domains. The domains are named sequentially as follows: CH1-hinge-CH2-CH3(-CH4). CH4 is present in IgM, which has no hinge region. The immunoglobulin heavy chain constant region useful in the present disclosure may comprise an immunoglobulin hinge region, and may also include a CH3 domain. For example, the immunoglobulin heavy chain constant region may comprise an immunoglobulin hinge region, a CH2 domain and a CH3 domain. In some embodiments, the Fc subunit according to the present disclosure consists of the hinge-CH2-CH3 domain.

The term "complexed with" or "complexation" as used herein, generally refers to the association (e.g., binding) of one member/subunit with another member/subunit of a molecule (e.g., a proteinaceous heterodimer). For example, a first Fc subunit may be complexed with a second subunit to form a dimer.

The term "binding specificity" as used herein, generally refers to the ability to specifically bind (e.g., immunoreact with) a given target (while not binding or substantially not binding a non-target). A targeting moiety of the present disclosure may be monospecific and contain one or more binding sites which specifically bind a target or may be multi specific (e.g., bispecific or trispecific) and contain two or more binding sites which specifically bind the same or different targets.

The term "associates with" or "associated with" as used herein, generally refers to that one entity is in physical association or contact with another. For example, a first monomeric member of the proteinaceous heterodimer may "associate with" a second monomeric member covalently or non-covalently. In some embodiments, a first monomeric member of the proteinaceous heterodimer associates with a second monomeric member via an interface, and the interface is formed by amino acid residues (i.e., interface residues) from the first monomeric member and the second monomeric member, respectively.

The term "modification" as used herein, generally refers to any manipulation of the peptide backbone (e.g. amino acid sequence) or any post-translational modifications (e.g. glycosylation) of a polypeptide. For example, a modification is in comparison to the sequence of a corresponding wild-type polypeptide. A modification may be a substitution, an addition, and/or a deletion of one or more amino acids (e.g., 1, 2, 3, 4, 5, 6, 7, 8, 9, 10, or more).

The term "knob-and-hole modification" as used herein, generally refers to introducing a modification at the interface of a polypeptide to form a bulge (knob modification) and introducing a modification at a corresponding position of another polypeptide to form a cavity (hole-modification), and the size of the bulge is the same or similar to that of the cavity. For example, the knob-and-hole modification enables the formation of a heterodimer, while inhibiting the formation of homodimers. See the reference of U.S. Pat. Nos. 5,731,168; 7,695,936; Ridgway et al., Prot Eng 9, 617-621 (1996) and Carter, J Immunol Meth 248, 7-15 (2001). Accordingly, the term "knob modification" as used herein, generally refers to a modification at the interface of a polypeptide to replace an amino acid having a smaller side chain (e.g., alanine or threonine) with an amino acid having a larger side chain (e.g., tyrosine or tryptophan) to form a bulge. The term "hole modification" as used herein, generally refers to a modification at a corresponding position of another polypeptide to replace an amino acid having a larger side chain (e.g., tyrosine or tryptophan) with an amino acid having a smaller side chain (e.g., alanine or threonine) to form a cavity. The knob modification and the hole modification can be made by altering the nucleic acid encoding the polypeptides, e.g. by site-specific mutagenesis, or by peptide synthesis. In a specific embodiment, a knob modification comprises the amino acid substitutions Y349C and T366W in one of the two subunits of the Fc region, and the hole modification comprises the amino acid substitutions D356C, T366S, L368A and Y407V in the other one of the two subunits of the Fc region.

The term "HEK293 cell" as used herein, generally refers to clonal isolates derived from transformed human embryonal kidney (HEK) cells. The HEK293 strain is a variant of the 293 cell line that demonstrates better adherence in monolayer culture and ease of use for plaque assays and other anchorage dependent applications. They have been adapted to suspension culture in serum-free media, e.g., 293 SFM II.

The term "CHO cell" as used herein, generally refers to Chinese hamster ovary cells, which are non-secretory, immortal fibroblasts. The CHO cells rarely secrete CHO endogenous protein, so is favorable to the separation and purification for a target protein.

The term "COS-1 cell" as used herein, generally refers to fibroblast-like cell lines derived from monkey kidney tissue. COS cells are obtained by immortalizing CV-1 cells with a version of the SV40 virus that can produce large T antigen but has a defect in genomic replication. One form of COS cell lines commonly used is COS-1.

The term "NSO cell" as used herein, generally refers to a model cell line derived from the non-secreting murine myeloma. The cell line is a cholesterol-dependent cell line that was generated from a subline of NSI/1.

The term "fusion protein" as used herein, generally refers to a polypeptide that comprises, or alternatively consists of, an amino acid sequence of a polypeptide fused directly or indirectly (e.g., via a linker) to an amino acid sequence of a heterologous polypeptide (i.e., a polypeptide unrelated to the former polypeptide or the domain thereof).

The term "C-terminus" as used herein, generally refers to the carboxy terminus of a polypeptide.

The term "N-terminus" as used herein, generally refers to the amino terminus of a polypeptide.

The term "immunoglobulin" as used herein, generally refers to a protein consisting of one or more polypeptides substantially encoded by immunoglobulin genes. The recognized immunoglobulin genes include the κ, λ, α, γ (IgG1, IgG2, IgG3, IgG4), δ, ε and μ constant region genes, as well as the myriad immunoglobulin variable region genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to antibodies, immunoglobulins may exist in a variety of other forms including, for example, Fv, Fab, Fab' and (Fab')2.

The term "fused in frame" or "in frame fused" as used herein, generally refers to the joining of two or more open reading frames (ORFs) to form a continuous longer ORF, in a manner that maintains the correct reading frame of the original ORFs.

The term "linker" as used herein, generally refers to a synthetic amino acid sequence that connects or links two polypeptide sequences, e.g., that links two polypeptide domains. A linker may connect two amino acid sequences via peptide bonds. In some embodiments, a linker of the present disclosure connects an immunoregulator to the second Fc region in a linear sequence.

The term "located N-terminal to" as used herein, generally refers to locating at a position N-terminal to another molecule (e.g., another polypeptide). For example, according to the present disclosure, two or more immunoregulators may be located N-terminal to the second Fc region.

The term "amino acid substitution" as used herein, generally refers to that one amino acid at a specific position of a polypeptide is replaced by another amino acid.

The term "EU index of the KABAT number" as used herein, generally refers to the index of the EU number corresponding to the amino acid sequence according to Kabat et al. (1971) Ann. NY Acad, Sci. 190: 382-391 and Kabat, E. A., et al. (1991) Sequences of Proteins of Immunological Interest, Fifth Edition, U.S. Department of Health and Human Services, NIH Publication No. 91-3242.

The term "isolated polynucleotide" as used herein, generally refers to a polymeric form of nucleotides of any length, either deoxyribonucleotides or ribonucleotides, or analogs thereof, isolated from its native environment, or that is artificially synthesized.

The term "protein mixture" as used herein, generally refers to a mixture of two or more types of proteins.

The term "homodimer" as used herein, generally refers to a molecule formed by two identical monomers (e.g., two identical members or subunits). The two monomers may aggregate, complex or associate with each other via covalent and/or non-covalent interactions. For example, the two monomers of a proteinaceous homodimer may associate with each other via interactions between interface amino acid residues from each of said two monomers.

The term "substantially comprises no" as used herein, generally refers that a composition (e.g., a mixture) comprises little or almost none of a substance. For example, said substance is present with a percentage of e.g., less than 10%, less than 9%, less than 8%, less than 7%, less than 6%, less than 5%, less than 4%, less than 3%, less than 2%, less than 1%, less than 0.5%, less than 0.1%, or less than 0.01%.

The term "pharmaceutically acceptable excipient" as used herein, generally refers to any and all solvents, dispersion media, coatings, isotonic and absorption delaying agents, etc., that are compatible with pharmaceutical administration.

The term "enrichment" as used herein, generally refers to an increase of the number and/or concentration of a target component in a mixture or a population.

Proteinaceous Heterodimers, Protein Mixtures, Isolated Polynucleotides, Vectors and Host Cells In one aspect, the present disclosure provides a proteinaceous heterodimer. The proteinaceous heterodimer may comprise a first monomeric member and a second monomeric member different from the first monomeric member. The first monomeric member may comprise a first Fc subunit. The second monomeric member may comprise a second Fc subunit. The first monomeric member may associate with the second monomeric member to form the heterodimer through complexation of the first Fc subunit with the second Fc subunit.

In some embodiments, the amino acid sequence of the first monomeric member is different from the amino acid sequence of the second monomeric member.

The proteinaceous heterodimer may further comprise one or more interleukins. The one or more interleukins may be fused (e.g., in frame fused) to the first Fc subunit and/or the second Fc subunit. For example, the one or more interleukins may independently be fused (e.g., in frame fused) to the first Fc subunit and/or the second Fc subunit in frame. In some embodiments, one or more interleukins are fused (e.g., in frame fused) only to the first Fc subunit. In some embodiments, one or more interleukins are fused (e.g., in frame fused) only to the second Fc subunit. In some embodiments, one or more interleukins are fused (e.g., in frame fused) to both the first and the second Fc subunit.

The one or more interleukins may be fused (e.g., in frame fused) to an amino-terminal amino acid and/or a carboxy-terminal amino acid of the first Fc subunit and/or the second Fc subunit. In some embodiments, one or more of the interleukins are fused (e.g., in frame) to an amino-terminal amino acid of the first Fc subunit. In some embodiments, one or more of the interleukins are fused (e.g., in frame) to an amino-terminal amino acid of the second Fc subunit. In some embodiments, one or more of the interleukins are fused (e.g., in frame) to both an amino-terminal amino acid of the first Fc subunit and an amino-terminal amino acid of the second Fc subunit.

In the proteinaceous heterodimer, at least one of the one or more interleukins may be interleukin 10.

The one or more interleukins may be fused (e.g., in frame) to the first Fc subunit and/or the second Fc subunit directly or indirectly. For example, the one or more interleukins may be fused (e.g., in frame) to the first Fc subunit and/or the second Fc subunit via a linker, such as a peptide linker. The linker may be a synthetic amino acid sequence that connects or links two polypeptide sequences, e.g., via peptide bonds. In some embodiments, a linker is a peptide comprising e.g., 1, 2, 3, 4, 5, 6, 7, 8, 9, 10, 11, 12, 13, 14, 15, 16, 17, 18, 19, 20, 21, 22, 23, 24, 25 or more amino acids. For example, the linker may comprise 1-10 amino acids (e.g., 1, 2, 3, 4, 5, 6, 7, 8, 9, 10 or more amino acids), 1-15 amino acids (e.g., 1-11, 12, 13, 14, 15 amino acids), 1-20 amino acids, 1-30 amino acids or more. In some embodiments, the linker comprises an amino acid sequence as set forth in SEQ ID NO: 37.

In some embodiments, the proteinaceous heterodimer comprises two or more interleukins. The two or more interleukins may be the same or may be different. In some embodiments, the two or more interleukins are the same. In some embodiments, the two or more interleukins are interleukin 10.

The two or more interleukins may form one or more interleukin dimers, with each interleukin dimer comprising two interleukins fused (e.g., in frame) to each other. Each interleukin dimer may comprise two identical or two different interleukins. The interleukins may be fused (e.g., in frame) together directly or indirectly. In some embodiments, the one or more interleukin dimers comprises at least one interleukin 10 dimer, with the interleukin 10 dimer comprising two interleukin 10.

Two or more interleukins (e.g., two interleukins of each interleukin dimer) may be fused (e.g., in frame) together through a linker (such as a peptide linker). The linker may be a synthetic amino acid sequence that connects or links two polypeptide sequences, e.g., via peptide bonds. In some embodiments, a linker is a peptide comprising 1, 2, 3, 4, 5, 6, 7, 8, 9, 10, 11, 12, 13, 14, 15, 16, 17, 18, 19, 20, 21, 22, 23, 24, 25 or more amino acids. For example, the linker may comprise 1-10 amino acids (e.g., 1, 2, 3, 4, 5, 6, 7, 8, 9, 10 or more amino acids), 1-15 amino acids (e.g., 1-11, 12, 13, 14, 15 amino acids), 1-20 amino acids, 1-30 amino acids or more. In some embodiments, the linker comprises an amino acid sequence as set forth in SEQ ID NO: 37. In some embodiments, the linker is resistant to proteolysis or substantially resistant to proteolysis.

In some cases, more than two interleukins may be comprised by the proteinaceous heterodimer. The more than two interleukins may form two or more interleukin dimers. For example, the two or more interleukin dimers may comprise at least one interleukin 10 dimer, and the interleukin 10 dimer comprises two interleukin 10. In some embodiments, the proteinaceous heterodimer comprises two or more interleukin 10 dimers.

The fused two or more interleukins (e.g., interleukin dimer) may further be fused (e.g., in frame) to an amino-terminal amino acid and/or a carboxy-terminal amino acid of the first Fc subunit and/or the second Fc subunit. In some embodiments, the fused two or more interleukins (e.g., interleukin dimer) are further fused to an amino-terminal amino acid of the first Fc subunit and/or the second Fc subunit. In some embodiments, the fused two or more interleukins (e.g., interleukin dimer) are further fused to an amino-terminal amino acid of only the first Fc subunit. In some embodiments, the fused two or more interleukins (e.g., interleukin dimer) are further fused to an amino-terminal amino acid of only the second Fc subunit. In some embodiments, the fused two or more interleukins (e.g., interleukin dimer) are further fused to both an amino-terminal amino acid of the first Fc subunit and an amino-terminal amino acid of the second Fc subunit.

When there are two or more interleukin dimers, each interleukin dimer may independently be fused to an amino-terminal amino acid and/or a carboxy-terminal amino acid of the first Fc subunit and/or the second Fc subunit. For example, two or more fused interleukins (e.g., interleukin 10) may be further fused (e.g., in frame) to the first Fc subunit (e.g., to an amino-terminal amino acid thereof) and two or more fused interleukins (e.g., interleukin 10) may be further fused (e.g., in frame) to the second Fc subunit (e.g., to an amino-terminal amino acid thereof).

The fused two or more interleukins (e.g., interleukin dimer) may be fused to the first Fc subunit and/or the second Fc subunit directly or indirectly. For example, the fused two or more interleukins (e.g., interleukin dimer) may be fused to the first Fc subunit and/or the second Fc subunit via a linker (such as a peptide linker). The linker may be a synthetic amino acid sequence that connects or links two polypeptide sequences, e.g., via peptide bonds. In some embodiments, a linker is a peptide comprising 1, 2, 3, 4, 5, 6, 7, 8, 9, 10, 11, 12, 13, 14, 15, 16, 17, 18, 19, 20, 21, 22, 23, 24, 25 or more amino acids. For example, the linker may comprise 1-10 amino acids (e.g., 1, 2, 3, 4, 5, 6, 7, 8, 9, 10 or more amino acids), 1-15 amino acids (e.g., 1-11, 12, 13, 14, 15 amino acids), 1-20 amino acids, 1-30 amino acids or more. In some embodiments, the linker comprises an amino acid sequence as set forth in SEQ ID NO: 37. In some embodiments, the linker is resistant to proteolysis or substantially resistant to proteolysis.

In some embodiments, at least one of the one or more interleukins is fused (e.g., in frame) to the second Fc subunit. For example, the at least one of the one or more interleukins may be fused to an amino-terminal amino acid of the second Fc subunit.

In some embodiments, in the second monomeric member, at least two of the one or more interleukins are fused (e.g., in frame) to each other to form an interleukin dimer, and the interleukin dimer is further fused (in frame) to the amino-terminal amino acid of the second Fc subunit.

In some embodiments, the first monomeric member does not comprise any interleukin.

In some embodiments, the first monomeric member consists of the first Fc subunit.

In some embodiments, at least one of the one or more interleukins is fused (e.g., in frame) to the first Fc subunit.

In some embodiments, at least one of the one or more interleukins is fused (e.g., in frame) to an amino-terminal amino acid of the first Fc subunit.

In some embodiments, in the first monomeric member, at least two of the one or more interleukins are fused (e.g., in frame) to each other to form an interleukin dimer, and the interleukin dimer is further fused (e.g., in frame) to the amino-terminal amino acid of the first Fc subunit.

In some embodiments, the second monomeric member does not comprise any interleukin.

In some embodiments, the second monomeric member consists of the second Fc subunit.

In some embodiments, the first monomeric member does not comprise any interleukin, or the first monomeric member consists of the first Fc subunit, and at least one of the one or more interleukins is fused (e.g., in frame) to the second Fc subunit. In some cases, in the second monomeric member, at least two of the one or more interleukins are fused (e.g., in frame) to each other to form an interleukin dimer, and the interleukin dimer is further fused (in frame) to the amino-terminal amino acid of the second Fc subunit.

In some embodiments, the second monomeric member does not comprise any interleukin, or the second monomeric member consists of the second Fe subunit, and at least one of the one or more interleukins is fused (e.g., in frame) to the first Fc subunit. In some cases, in the first monomeric member, at least two of the one or more interleukins are fused (e.g., in frame) to each other to form an interleukin dimer, and the interleukin dimer is further fused (in frame) to the amino-terminal amino acid of the first Fc subunit.

In some embodiments, the first monomeric member comprises one or more interleukins fused to the first Fc subunit, and the second monomeric member comprises one or more interleukins fused to the second Fc subunit.

In some embodiments, the first monomeric member comprises one or more interleukin dimers fused to the first Fc subunit, and the second monomeric member comprises one or more interleukin dimers fused to the second Fc subunit. Each interleukin dimer may comprise two identical interleukins fused (e.g. in frame) to each other directly or indirectly (e.g., via a linker, such as a peptide linker).

The proteinaceous heterodimer of the present application does not comprise any antibody heavy chain variable region or any antibody light chain variable region exhibiting binding specificity to a tumor antigen. In some embodiments, the proteinaceous heterodimer of the present application does not comprise any antibody or any part (e.g., an antigen-binding fragment) thereof exhibiting binding specificity to a tumor antigen.

In some embodiments, the proteinaceous heterodimer of the present application does not comprise any antibody heavy chain variable region or any antibody light chain variable region.

In some embodiments, the proteinaceous heterodimer of the present application does not comprise any antibody or antigen-binding fragments thereof.

In some embodiments, the proteinaceous heterodimer of the present application does not comprise any targeting moiety exhibiting binding specificity to any tumor antigen. For example, in some cases, the proteinaceous heterodimer of the present application does not comprise any antibody or antigen-binding fragments thereof capable of specifically binding to a tumor antigen.

In some embodiments, the first Fc subunit and/or the second Fc subunit is independently from an IgG molecule.

The IgG may be selected from the group consisting of IgG1, IgG2, IgG3 and IgG4. For example, the IgG may be a human IgG1.

In some embodiments, the first Fc subunit is different from the second Fc subunit, and the first and/or second Fc subunit comprises a modification promoting heterodimerization between the first Fc subunit and the second Fc subunit.

The first Fc subunit may comprise a first modification, and the second Fc subunit may comprise a second modification.

In some embodiments, the first modification comprises an amino acid substitution at position T366, and an amino acid substitution at one or more positions selected from the group consisting of: Y349, F405, K409, D399, K360, Q347, K392 and 5354, wherein the position of the amino acid is determined according to the EU index of the KABAT number. For example, the amino acid substitution comprised by the first modification may be selected from the group consisting of: Y349C, Y349D, D399S, F405K, K360E, K409A, K409E, Q347E, Q347R, S354D, K392D and T366W.

In some embodiments, the first modification comprises 2-5 amino acid substitutions.

In some embodiments, the first modification comprises an amino acid substitution at a group of positions selected from any of the following groups: 1) Y349 and T366; 2) Y349, T366 and F405; 3) Y349, T366 and K409; 4) Y349, T366, F405, K360 and Q347; 5) Y349, T366, F405 and Q347; 6) Y349, T366, K409, K360 and Q347; 7) Y349, T366, K409 and Q347; 8) T366, K409 and K392; 9) T366 and K409; 10) T366, K409, Y349 and S354; 11) T366 and F405; 12) T366, F405 and D399; and 13) T366, F405, Y349 and S354; wherein the position of the amino acid is determined according to the EU index of the KABAT number.

In some embodiments, the first modification comprises a group of amino acid substitutions selected from any of the following groups: 1) Y349C and T366W; 2) Y349C, T366W and F405K; 3) Y349C, T366W and K409E; 4) Y349C, T366W and K409A; 5) Y349C, T366W, F405K, K360E and Q347E; 6) Y349C, T366W, F405K and Q347R; 7) Y349C, T366W, K409A, K360E and Q347E; 8) Y349C, T366W, K409A and Q347R; 9) T366W, K409A and K392D; 10) T366W and K409A; 11) T366W, K409A and Y349D; 12) T366W, K409A, Y349D and S354D; 13) T366W and F405K; 14) T366W, F405K and D399S; 15) T366W, F405K and Y349D; and 16) T366W, F405K, Y349D and S354D; wherein the position of the amino acid is determined according to the EU index of the KABAT number.

In some embodiments, the second modification comprises amino acid substitutions at positions T366, L368 and Y407, as well as an amino acid substitution at one or more positions selected from the group consisting of D356, D399, E357, F405, K360, K392, K409 and Q347, wherein the position of the amino acid is determined according to the EU index of the KABAT number.

In some embodiments, the amino acid substitution comprised by the second modification is selected from the group consisting of D356C, D399S, E357A, F405K, K360E, K392D, K409A, L368A, L368G, Q347E, Q347R, T366S, Y407A and Y407V.

In some embodiments, the second modification comprises an amino acid substitution at 4-6 positions.

In some embodiments, the second modification comprises an amino acid substitution at a group of positions selected from any of the following groups: 1) D356, T366, L368, Y407 and F405; 2) D356, T366, L368 and Y407; 3) D356, T366, L368, Y407 and Q347; 4) D356, T366, L368, Y407, K360 and Q347; 5) D356, T366, L368, Y407, F405 and Q347; 6) D356, T366, L368, Y407, F405, K360 and Q347; 7) T366, L368, Y407, D399 and F405; 8) T366, L368, Y407 and F405; 9) T366, L368, Y407, F405 and E357; 10) T366, L368, Y407 and K409; 11) T366, L368, Y407, K409 and K392; and 12) T366, L368, Y407, K409 and E357; wherein the position of the amino acid is determined according to the EU index of the KABAT number.

In some embodiments, the second modification comprises a group of amino acid substitutions selected from any of the following groups: 1) D356C, T366S, L368A, Y407V and F405K; 2) D356C, T366S, L368A and Y407V; 3) D356C, T366S, L368A, Y407V and Q347R; 4) D356C, T366S, L368A, Y407V, K360E and Q347E; 5) D356C, T366S, L368A, Y407V, F405K and Q347R; 6) D356C, T366S, L368A, Y407V, F405K, K360E and Q347E; 7) T366S, L368A, Y407V, D399S and F405K; 8) T366S, L368G, Y407A and F405K; 9) T366S, L368A, Y407V, F405K and E357A; 10) T366S, L368A, Y407V and K409A; 11) T366S, L368A, Y407V, K409A and K392D; 12) T366S, L368G, Y407A and K409A; 13) T366S, L368A, Y407V, K409A and E357A; wherein the position of the amino acid is determined according to the EU index of the KABAT number.

In some embodiments, the first Fc subunit comprises the first modification, the second Fc subunit comprises the second modification, and the first modification and the second modification comprise an amino acid substitution at a group of positions selected from any of the following groups: 1) the first modification: Y349 and T366; and the second modification: D356, T366, L368, Y407 and F405; 2) the first modification: Y349, T366 and F405; and the second modification: D356, T366, L368 and Y407; 3) the first modification: Y349, T366 and K409; and the second modification: D356, T366, L368, Y407 and F405; 4) the first modification: Y349, T366, F405, K360 and Q347; and the second modification: D356, T366, L368, Y407 and Q347; 5) the first modification: Y349, T366, F405 and Q347; and the second modification: D356, T366, L368, Y407, K360 and Q347; 6) the first modification: Y349, T366, K409, K360 and Q347; and the second modification: D356, T366, L368, Y407, F405 and Q347; 7) the first modification: Y349, T366, K409 and Q347; and the second modification: D356, T366, L368, Y407, F405, K360 and Q347; 8) the first modification: T366, K409 and K392; and the second modification: T366, L368, Y407, D399 and F405; 9) the first modification: T366 and K409; and the second modification: T366, L368, Y407 and F405; 10) the first modification: T366, K409 and Y349; and the second modification: T366, L368, Y407, F405 and E357; 11) the first modification: T366, K409, Y349 and 5354; and the second modification: T366, L368, Y407, F405 and E357; 12) the first modification: T366 and F405; and the second modification: T366, L368, Y407 and K409; 13) the first modification: T366, F405 and D399; and the second modification: T366, L368, Y407, K409 and K392; 14) the first modification: T366, F405 and Y349; and the second modification: T366, L368, Y407, K409 and E357; 15) the first modification: T366, F405, Y349 and S354; and the second modification: T366, L368, Y407, K409 and E357; wherein the position of the amino acid is determined according to the EU index of the KABAT number.

In some embodiments, the first Fc subunit comprises the first modification, the second Fc subunit comprises the second modification, wherein the first modification and the second modification comprise a group of amino acid substitutions selected from any of the following groups: 1) the first modification: Y349C and T366W; and the second modification: D356C, T366S, L368A, Y407V and F405K; 2) the first modification: Y349C, T366W and F405K; and the second modification: D356C, T366S, L368A and Y407V; 3) the first modification: Y349C, T366W and K409E; and the second modification: D356C, T366S, L368A, Y407V and F405K; 4) the first modification: Y349C, T366W and K409A; and the second modification: D356C, T366S, L368A, Y407V and F405K; 5) the first modification: Y349C, T366W, F405K, K360E and Q347E; and the second modification: D356C, T366S, L368A, Y407V and Q347R; 6) the first modification: Y349C, T366W, F405K and Q347R; and the second modification: D356C, T366S, L368A, Y407V, K360E and Q347E; 7) the first modification: Y349C, T366W, K409A, K360E and Q347E; and the second modification: D356C, T366S, L368A, Y407V, F405K and Q347R; 8) the first modification: Y349C, T366W, K409A and Q347R; and the second modification: D356C, T366S, L368A, Y407V, F405K, K360E and Q347E; 9) the first modification: T366W, K409A and K392D; and the second modification: T366S, L368A, Y407V, D399S and F405K; 10) the first modification: T366W and K409A; and the second modification: T366S, L368G, Y407A and F405K; 11) the first modification: T366W, K409A and Y349D; and the second modification: T366S, L368A, Y407V, F405K and E357A; 12) the first modification: T366W, K409A, Y349D and S354D; and the second modification: T366S, L368A, Y407V, F405K and E357A; 13) the first modification: T366W and F405K; and the second modification: T366S, L368A, Y407V and K409A; 14) the first modification: T366W, F405K and D399S; and the second modification: T366S, L368A, Y407V, K409A and K392D; 15) the first modification: T366W and F405K; and the second modification: T366S, L368G, Y407A and K409A; 16) the first modification: T366W, F405K and Y349D; and the second modification: T366S, L368A, Y407V, K409A and E357A; 17) the first modification: T366W, F405K, Y349D and S354D; and the second modification: T366S, L368A, Y407V, K409A and E357A; wherein the position of the amino acid is determined according to the EU index of the KABAT number.

In some embodiments, the first Fc subunit comprises the first modification, the second Fc subunit comprises the second modification, the first modification comprises the amino acid substitutions T366W and K409A, and the second modification comprises the amino acid substitutions T366S, L368G, Y407A and F405K, wherein the position of the amino acid is determined according to the EU index of the KABAT number.

In some embodiments, the first and second Fc subunit comprises modifications promoting heterodimerization between the first Fc subunit and the second Fc subunit, such as a knob-and-hole modification. For example, the first Fc subunit may comprise a knob modification and the second Fc subunit may comprise a hole modification. In some cases, the first Fc subunit may comprise a hole modification and the second Fc subunit may comprise a knob modification.

The knob modification may comprise the amino acid substitutions Y349C and T366W, and the hole modification may comprise the amino acid substitutions D356C, T366S, L368A and Y407V, wherein the position of the amino acid is determined according to the EU index of the KABAT number.

In some embodiments, the amino acid sequence of the first Fc subunit is selected from the group consisting of: SEQ ID NO:1, 3, 5 ,6, 7, 9, 11, 13, 15, 17, 19, 21, 22, 24, 27, 29 and 30.

In some embodiments, the amino acid sequence of the interleukins comprised by the proteinaceous heterodimer is selected from the group consisting of: SEQ ID NO: 49 and 51.

In some embodiments, the amino acid sequence of the second Fc subunit is selected from the group consisting of: SEQ ID NO:2, 4, 8, 10, 12, 14, 16, 18, 20, 23, 25, 26, 28 and 30.

In one aspect, the present disclosure provides an isolated nucleic acid or isolated nucleic acids encoding the proteinaceous heterodimer according to the present disclosure. In some embodiments, an isolated nucleic acid encodes a monomeric member (e.g., the first monomeric member or the second monomeric member) or a fragment of the proteinaceous heterodimer according to the present disclosure.

The nucleic acid may be synthesized using recombinant techniques well known in the art. For example, the nucleic acid may be synthesized using an automated DNA synthesizer.

Standard recombinant DNA and molecular cloning techniques include those described by Sambrook, J., Fritsch, E. F. and Maniatis, T *Molecular Cloning: A Laboratory Manual; Cold Spring Harbor Laboratory Press*: Cold Spring Harbor, (1989) (Maniatis) and by T. J. Silhavy, M L. Bennan, and L. W Enquist, *Experiments with Gene Fusions, Cold Spring Harbor Laboratory*, Cold Spring Harbor, N.Y. (1984) and by Ausubel, F. M et al., *Current Protocols in Molecular Biology*, pub. by Greene Publishing Assoc. and Wiley-Interscience (1987). Briefly, the subject nucleic acids can be prepared from genomic DNA fragments, cDNAs, and RNAs, all of which can be extracted directly from a cell or recombinantly produced by various amplification processes including but not limited to PCR and RT-PCR.

Direct chemical synthesis of nucleic acids typically involves sequential addition of 3'-blocked and 5'-blocked nucleotide monomers to the terminal 5'-hydroxyl group of a growing nucleotide polymer chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. See for example, Matteuci et al., *Tet. Lett.* 521: 719 (1980); U.S. Pat. No. 4,500,707 to Caruthers et al.; and U.S. Pat. Nos. 5,436,327 and 5,700,637 to Southern et al.

In one respect, the present disclosure provides a vector or vectors comprising the isolated nucleic acid or isolated nucleic acids according to the present disclosure.

The vector may be any linear nucleic acids, plasmids, phagemids, cosmids, RNA vectors, viral vectors and the like. Non-limiting examples of a viral vector may include a retrovirus, an adenovirus and an adeno-associated virus. In some embodiments, the vector is an expression vector, e.g. a phage display vector.

An expression vector may be suitable for use in particular types of host cells and not others. For example, the expression vector can be introduced into the host organism, which is then monitored for viability and expression of any genes/polynucleotides contained in the vector.

The expression vector may also contain one or more selectable marker genes that, upon expression, confer one or more phenotypic traits useful for selecting or otherwise identifying host cells that carry the expression vector. Non-limiting examples of suitable selectable markers for eukaryotic cells include dihydrofolate reductase and neomycin resistance.

The subject vectors can be introduced into a host cell stably or transiently by a variety of established techniques.

For example, one method involves a calcium chloride treatment wherein the expression vector is introduced via a calcium precipitate. Other salts, for example calcium phosphate, may also be used following a similar procedure. In addition, electroporation (that is, the application of current to increase the permeability of cells to nucleic acids) may be used. Other examples of transformation methods include microinjection, DEAE dextran mediated transformation, and heat shock in the presence of lithium acetate. Lipid complexes, liposomes, and dendrimers may also be employed to transfect the host cells.

Upon introduction of the heterologous sequence into a host cell, a variety of methods can be practiced to identify the host cells into which the subject vectors have been introduced. One exemplary selection method involves subculturing individual cells to form individual colonies, followed by testing for expression of the desired protein product. Another method entails selecting host cells containing the heterologous sequence based upon phenotypic traits conferred through the expression of selectable marker genes contained within the expression vector.

For example, the introduction of various heterologous sequences of the disclosure into a host cell can be confirmed by methods such as PCR, Southern blot or Northern blot hybridization. For example, nucleic acids can be prepared from the resultant host cells, and the specific sequences of interest can be amplified by PCR using primers specific for the sequences of interest. The amplified product is subjected to agarose gel electrophoresis, polyacrylamide gel electrophoresis or capillary electrophoresis, followed by staining with ethidium bromide, SYBR Green solution or the like, or detection of DNA with a UV detection. Alternatively, nucleic acid probes specific for the sequences of interest can be employed in a hybridization reaction. The expression of a specific gene sequence can be ascertained by detecting the corresponding mRNA via reverse-transcription coupled with PCR, Northern blot hybridization, or by immunoassays using antibodies reactive with the encoded gene product. Exemplary immunoassays include but are not limited to ELISA, radioimmunoassays, and sandwich immunoassays.

Furthermore, the introduction of various heterologous sequences of the disclosure into a host cell can be confirmed by the enzymatic activity of an enzyme (e.g., an enzymatic marker) that the heterologous sequence encodes. The enzyme can be assayed by a variety of methods known in the art. In general, the enzymatic activity can be ascertained by the formation of the product or conversion of a substrate of an enzymatic reaction that is under investigation. The reaction can take place in vitro or in vivo.

In one respect, the present disclosure provides an isolated host cell comprising the isolated nucleic acid or isolated nucleic acids or the vector or vectors according to the present disclosure.

The host cell may be a eukaryotic cell or a prokaryotic cell. An appropriate host cell may be transformed or transfected with the polynucleotide or vector of the present disclosure, and utilized for the expression and/or secretion of the heterodimer protein and/or protein mixtures. For example, the cell may be *E. coli* cells, other bacterial host cells, yeast cells, or various higher eukaryotic cells (e.g., immortal hybridoma cells, NSO myeloma cells, HEK293 cells, Chinese hamster ovary cells, HeLa cells, COS cells, etc.). In some embodiments, nucleic acids encoding the proteinaceous heterodimer (e.g., a heterodimer protein) are operably connected to an expression control sequence suitable for expression in specific host cells.

In one respect, the present disclosure provides a protein mixture. The protein mixture may comprise: 1) the proteinaceous heterodimer according to the present disclosure; 2) a first homodimer formed by two identical copies of the first monomeric member of the proteinaceous heterodimer according to the present disclosure; and 3) a second homodimer formed by two identical copies of the second monomeric member of the proteinaceous heterodimer according to the present disclosure. A percentage of the proteinaceous heterodimer in the protein mixture may be at least about 50%, at least about 55%, at least about 60%, at least about 65%, at least about 70%, at least about 75%, at least about 80%, at least about 85%, at least about 90%, at least about 95% or at least about 99%.

In the protein mixture, the percentage of the second homodimer may be less than the percentage of the first homodimer. For example, the percentage of the second homodimer may be at most about 10%, at most about 9%, at most about 8%, at most about 7%, at most about 6%, at most about 5%, at most about 4%, at most about 3%, at most about 2%, at most about 1% or at most about 0.5%. For example, the protein mixture may substantially comprise none of the second homodimer.

The protein mixture may be produced directly by a host cell of the present disclosure, e.g., without enrichment/purification of the proteinaceous heterodimer and/or removing of the first or the second homodimer.

Pharmaceutical Compositions

In one respect, the present disclosure provides a pharmaceutical composition comprising the proteinaceous heterodimer according to the present disclosure; or the protein mixture according to the present disclosure, and optionally a pharmaceutically acceptable excipient.

Examples of pharmaceutically acceptable excipients include, but are not limited to inert solid diluents and fillers, diluents, sterile aqueous solution and various organic solvents, permeation enhancers, solubilizers and adjuvants.

In some embodiments, the proteinaceous heterodimer is formulated for oral administration, intravenous administration, intramuscular administration, in-situ administration at the site of a tumor, inhalation, rectal administration, vaginal administration, transdermal administration, or administration via subcutaneous repository.

The pharmaceutical composition may be used for inhibiting tumor growth. For example, the pharmaceutical compositions may inhibit or delay the development or progress of a disease, may reduce tumor size (and even substantially eliminate tumors), and may alleviate and/or stabilize a disease condition.

Described below are non-limiting exemplary pharmaceutical compositions and methods for preparing the same.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition can further comprise a proteinaceous heterodimer (e.g., a heterodimer protein) or a protein mixture according to the present disclosure as an active ingredient and may include a conventional pharmaceutical carrier or excipient. Further, it may include other medicinal or pharmaceutical agents, carriers, adjuvants, etc.

Exemplary parenteral administration forms include, but not limited to, solutions or suspensions of an active proteinaceous heterodimer (e.g., a heterodimer protein) in sterile aqueous solutions, for example, aqueous propylene glycol or dextrose solutions. Such dosage forms can be suitably buffered with salts such as histidine and/or phosphate, if desired.

In some embodiments, the present disclosure provides a pharmaceutical composition for injection containing a proteinaceous heterodimer (e.g., a heterodimer protein) or a protein mixture of the present disclosure and a pharmaceutical excipient suitable for injection.

The forms in which the pharmaceutical compositions of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

In some embodiments, the present disclosure provides a pharmaceutical composition for oral administration containing a proteinaceous heterodimer (e.g., a heterodimer protein) or a protein mixture of the present disclosure, and a pharmaceutical excipient suitable for oral administration.

In some embodiments, the present disclosure provides a solid pharmaceutical composition for oral administration containing: (i) an amount of a proteinaceous heterodimer (e.g., a heterodimer protein) or a protein mixture of the disclosure; optionally (ii) an amount of a second agent; and (iii) a pharmaceutical excipient suitable for oral administration. In some embodiments, the composition further contains: (iv) an amount of a third agent. In some embodiments, amounts of the proteinaceous heterodimer or the protein mixture, second agent, and optional third agent are amounts that, alone or in combination, are effective in treating a condition of a subject.

In some embodiments, the pharmaceutical composition may be a liquid pharmaceutical composition suitable for oral consumption. Pharmaceutical compositions of the disclosure suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods typically include the step of bringing the active ingredient into association with the carrier, which constitutes one or more other ingredients. In general, the compositions are prepared by uniformly and intimately admixing the active ingredient with liquid carriers or finely divided solid carriers or both, and then, if necessary, shaping the product into the desired presentation.

The present disclosure further encompasses anhydrous pharmaceutical compositions and dosage forms comprising an active ingredient (e.g., a proteinaceous heterodimer or a heterodimer protein of the present disclosure), since water can facilitate the degradation of some polypeptides. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the disclosure can be prepared using anhydrous or low moisture containing ingredients and low moisture or low humidity conditions.

A proteinaceous heterodimer (e.g., a heterodimer protein) or a protein mixture of the present disclosure can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. If desired, tablets can be coated by standard aqueous or nonaqueous techniques.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The pharmaceutical compositions of the present disclosure may comprise a therapeutically effective amount of the active agent (e.g., the proteinaceous heterodimer or the protein mixture of the present disclosure). A therapeutically effective amount is an amount of the subject pharmaceutical composition capable of preventing and/or curing (at least partially) a condition or disorder (e.g., cancer) and/or any complications thereof in a subject suffering from or having a risk of developing said condition or disorder. The specific amount/concentration of the active agent comprised may vary according to the method of administration and the need of a patient, and can be determined based on e.g., volume, viscosity, and/or body weight of a patient etc. For example, an appropriate dosage may be about 0.1 mg or 1 mg/kg/day to about 50 mg/kg/day; sometimes, the dosage can be even higher. It shall be understood that these specific doses may be conveniently adjusted by a skilled person in the art (e.g., a doctor or a pharmacist) based on conditions of a specific patient, formulation, and/or disease.

Medical Use and Methods of Treatment

In one respect, the present disclosure provides a use of the proteinaceous heterodimer according to the present disclosure, or the protein mixture according to the present disclosure in the manufacture of a medicament and/or a kit for inhibiting growth of a tumor or a tumor cell. In some embodiments, the medicament and/or kit is used for specifically and/or preferentially inhibiting growth or differentiation of target cells (e.g., cancer cells) or killing target cells (e.g., cancer cells).

In one respect, the present disclosure provides a use of the proteinaceous heterodimer according to the present disclosure, or the protein mixture according to the present disclosure in the manufacture of a medicament for treating cancer in a subject in need thereof.

In one respect, the present disclosure provides a method for treating cancer in a subject in need thereof. The method may comprise administering to the subject an effective amount of the proteinaceous heterodimer according to the present disclosure, or the protein mixture according to the present disclosure.

In one respect, the present disclosure provides a method for inhibiting growth of a tumor or a tumor cell, comprising contacting the tumor or tumor cell with an effective amount of the proteinaceous heterodimer according to the present disclosure, or the protein mixture according to the present disclosure. The contacting may occur in vitro or in vivo.

In some embodiments, said contacting includes systemically or locally administering the proteinaceous heterodimer (e.g., a heterodimer protein), the protein mixture, the pharmaceutical composition or the medicament of the present disclosure to a subject (e.g., a mammal). In some embodiments, said contacting includes administering the proteinaceous heterodimer (e.g., a heterodimer protein), the protein mixture, the pharmaceutical composition, or the medicament of the present disclosure directly at the site of a tumor. In some embodiments, the administering is conducted by oral administration, intravenous administration, intramuscular administration, in-situ administration at the site of a tumor, inhalation, rectal administration, vaginal administration, transdermal administration or administration via subcutaneous repository.

In some embodiments, the tumor (e.g., cancer) or tumor cell (e.g., a cancer cell) is or is from a solid tumor. For example, the cancer may be selected from the group consisting of a B cell lymphoma, a lung cancer, a bronchus cancer, a colorectal cancer, a prostate cancer, a breast cancer, a pancreas cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, a biliary tract cancer, a small bowel or appendix cancer, a salivary gland cancer, a thyroid gland cancer, a adrenal gland cancer, an osteosarcoma, a chondrosarcoma, a liposarcoma, a testes cancer, and a malignant fibrous histiocytoma.

In some embodiments, the cancer or cancer cell is within the body of a subject, e.g., a cancer or cancer cell within a human or in a non-human animal (e.g., a mammal).

In some embodiments, the mammal is a human. In some embodiments, the mammal is a mouse, a rat, a cat, a dog, a rabbit, a pig, a sheep, a horse, a bovine, a goat, a gerbil, a hamster, a guinea pig, a monkey or any other mammal. Many such mammals may be subjects that are known to the art as preclinical models for certain diseases or disorders, including solid tumors and/or other cancers (e.g., Talmadge et al., 2007 Am. J. Pathol. 170: 793; Kerbel, 2003 Canc. Biol. Therap. 2(4 Suppl 1): S134; Man et al., 2007 Canc. Met. Rev. 26: 737; Cespedes et al., 2006 Clin. TransL Oncol. 8: 318).

Method for Preparing Proteinaceous Heterodimers or Protein Mixtures

In one respect, the present disclosure provides a method for producing a proteinaceous heterodimer according to the present disclosure or a protein mixture according to the present disclosure. The method may comprise (i) culturing the host cell of the present disclosure under conditions to effect expression of the proteinaceous heterodimer, and (ii) harvesting the expressed proteinaceous heterodimer or a protein mixture comprising the proteinaceous heterodimer.

In some embodiments, the method does not comprise enriching the proteinaceous heterodimer in the products expressed by the host cells according to the present disclosure.

In some embodiments, the method does not comprise removing the first or the second homodimer from the protein mixture produced by the host cells according to the present disclosure.

In some embodiments, the method further comprises the steps of isolating and/or purifying the proteinaceous heterodimer or the protein mixture.

In some embodiments, the method further comprises transfecting/transforming host cells with polynucleotides/vectors encoding/expressing the heterodimer of the present disclosure, one or more members thereof, or fragments thereof.

In some embodiments, the proteinaceous heterodimer or the protein mixture of the present disclosure is produced by expressing a vector in a cell under conditions suitable for protein expression. In some embodiments, the proteinaceous heterodimer or the protein mixture of the present disclosure is produced by a single cell clone.

Factors that may vary among suitable conditions for protein expression include factors such as incubation time, temperature, and medium, and may depend on cell type and will be readily determined by one of ordinary skill in the art.

In some embodiments, during the process of producing the proteinaceous heterodimer or the protein mixture of the present disclosure, the host cells are grown in cultures, and in any apparatus that may be used to grow cultures, including fermenters. Cells may be grown as monolayers or attached to a surface. Alternatively, the host cells may be grown in suspension. The cells can be grown in a culture medium that is serum-free. The media can be a commercially available media, such as, but not limited to, Opti-CHO (Invitrogen, Catalogue #12681) supplemented with glutamine, such as 8 mM L-glutamine; RPMI 1640 medium, supplemented with 10% bovine calf serum, 10.5 ng/ml mIL-3 and L-glutamine; or 5% FCS medium.

The present disclosure also includes the following embodiments:

1. A proteinaceous heterodimer comprising a first monomeric member and a second monomeric member different from said first monomeric member, wherein: said first monomeric member comprises a first Fc subunit, said second monomeric member comprises a second Fc subunit, and said first monomeric member associates with said second monomeric member to form said heterodimer through complexation of said first Fc subunit with said second Fc subunit; wherein said proteinaceous heterodimer further comprises one or more interleukins fused to said first Fc subunit and/or said second Fc subunit; and wherein said proteinaceous heterodimer does not comprise any antibody heavy chain variable region or any antibody light chain variable region exhibiting binding specificity to a tumor antigen.
2. The proteinaceous heterodimer according to embodiment 1, wherein said one or more interleukins is fused to an amino-terminal amino acid and/or a carboxy-terminal amino acid of said first Fc subunit and/or said second Fc subunit.
3. The proteinaceous heterodimer according to any one of embodiments 1-2, which comprises two or more interleukins.
4. The proteinaceous heterodimer according to embodiment 3, wherein said two or more interleukins form one or more interleukin dimers, with each interleukin dimer comprising two interleukins fused to each other.

5. The proteinaceous heterodimer according to embodiment 4, wherein said two interleukins of each interleukin dimer are fused to each other through a peptide linker.

6. The proteinaceous heterodimer according to any one of embodiments 4-5, wherein said interleukin dimer is fused to an amino-terminal amino acid and/or a carboxy-terminal amino acid of said first Fc subunit and/or said second Fc subunit.

7. The proteinaceous heterodimer according to any one of embodiments 1-6, wherein one or more of said interleukins is fused to said first Fc subunit and/or said second Fc subunit through a peptide linker.

8. The proteinaceous heterodimer according to any one of embodiments 1-7, wherein at least one of said one or more interleukins is IL10.

9. The proteinaceous heterodimer according to any one of embodiments 4-8, wherein said one or more interleukin dimers comprises at least one IL10 dimer, and said IL10 dimer comprises two IL10.

10. The proteinaceous heterodimer according to any one of embodiments 1-9, wherein said first Fc subunit and/or said second Fc subunit is from an IgG molecule.

11. The proteinaceous heterodimer according to embodiment 10, wherein said IgG is selected from the group consisting of IgG1, IgG2, IgG3 and IgG4.

12. The proteinaceous heterodimer according to embodiment 11, wherein said IgG is a human IgG1.

13. The proteinaceous heterodimer according to any one of embodiments 1-12, wherein said proteinaceous heterodimer does not comprise any targeting moiety exhibiting binding specificity to any tumor antigen.

14. The proteinaceous heterodimer according to any one of embodiments 1-13, wherein said first Fc subunit is different from said second Fc subunit, and said first and/or second Fc subunit comprises a modification promoting heterodimerization between said first Fc subunit and said second Fc subunit.

15. The proteinaceous heterodimer according to embodiment 14, wherein said first Fc subunit comprises a first modification, and said second Fc subunit comprises a second modification.

16. The proteinaceous heterodimer according to embodiment 15, wherein said first modification comprises an amino acid substitution at position T366, and an amino acid substitution at one or more positions selected from the group consisting of: Y349, F405, K409, D399, K360, Q347, K392 and 5354, wherein the position of the amino acid is determined according to the EU index of the KABAT number.

17. The proteinaceous heterodimer according to embodiment 16, wherein the amino acid substitution comprised by the first modification is selected from the group consisting of: Y349C, Y349D, D399S, F405K, K360E, K409A, K409E, Q347E, Q347R, S354D, K392D and T366W.

18. The proteinaceous heterodimer according to any one of embodiments 15-17, wherein said first modification comprises 2-5 amino acid substitutions.

19. The proteinaceous heterodimer according to any one of embodiments 15-18, wherein said first modification comprises an amino acid substitution at a group of positions selected from any of the following groups: 1) Y349 and T366; 2) Y349, T366 and F405; 3) Y349, T366 and K409; 4) Y349, T366, F405, K360 and Q347; 5) Y349, T366, F405 and Q347; 6) Y349, T366, K409, K360 and Q347; 7) Y349, T366, K409 and Q347; 8) T366, K409 and K392; 9) T366 and K409; 10) T366, K409, Y349 and S354; 11) T366 and F405; 12) T366, F405 and D399; and 13) T366, F405, Y349 and S354; wherein the position of the amino acid is determined according to the EU index of the KABAT number.

20. The proteinaceous heterodimer according to any one of embodiments 15-19, wherein said first modification comprises a group of amino acid substitutions selected from any of the following groups: 1) Y349C and T366W; 2) Y349C, T366W and F405K; 3) Y349C, T366W and K409E; 4) Y349C, T366W and K409A; 5) Y349C, T366W, F405K, K360E and Q347E; 6) Y349C, T366W, F405K and Q347R; 7) Y349C, T366W, K409A, K360E and Q347E; 8) Y349C, T366W, K409A and Q347R; 9) T366W, K409A and K392D; 10) T366W and K409A; 11) T366W, K409A and Y349D; 12) T366W, K409A, Y349D and S354D; 13) T366W and F405K; 14) T366W, F405K and D399S; 15) T366W, F405K and Y349D; and 16) T366W, F405K, Y349D and S354D; wherein the position of the amino acid is determined according to the EU index of the KABAT number.

21. The proteinaceous heterodimer according to any one of embodiments 15-20, wherein said second modification comprises amino acid substitutions at positions T366, L368 and Y407, as well as an amino acid substitution at one or more positions selected from the group consisting of D356, D399, E357, F405, K360, K392, K409 and Q347, wherein the position of the amino acid is determined according to the EU index of the KABAT number.

22. The proteinaceous heterodimer according to embodiment 21, wherein the amino acid substitution comprised by the second modification is selected from the group consisting of D356C, D399S, E357A, F405K, K360E, K392D, K409A, L368A, L368G, Q347E, Q347R, T366S, Y407A and Y407V.

23. The proteinaceous heterodimer according to any one of embodiments 15-22, wherein the second modification comprises an amino acid substitution at 4-6 positions.

24. The proteinaceous heterodimer according to any one of embodiments 15-23, wherein the second modification comprises an amino acid substitution at a group of positions selected from any of the following groups: 1) D356, T366, L368, Y407 and F405; 2) D356, T366, L368 and Y407; 3) D356, T366, L368, Y407 and Q347; 4) D356, T366, L368, Y407, K360 and Q347; 5) D356, T366, L368, Y407, F405 and Q347; 6) D356, T366, L368, Y407, F405, K360 and Q347; 7) T366, L368, Y407, D399 and F405; 8) T366, L368, Y407 and F405; 9) T366, L368, Y407, F405 and E357; 10) T366, L368, Y407 and K409; 11) T366, L368, Y407, K409 and K392; and 12) T366, L368, Y407, K409 and E357; wherein the position of the amino acid is determined according to the EU index of the KABAT number.

25. The proteinaceous heterodimer according to any one of embodiments 15-24, wherein the second modification comprises a group of amino acid substitutions selected from any of the following groups: 1) D356C, T366S, L368A, Y407V and F405K; 2) D356C, T366S, L368A and Y407V; 3) D356C, T366S, L368A, Y407V and Q347R; 4) D356C, T366S, L368A, Y407V, K360E and Q347E; 5) D356C, T366S, L368A, Y407V, F405K and Q347R; 6) D356C, T366S, L368A, Y407V, F405K, K360E and Q347E; 7) T366S, L368A, Y407V, D399S and F405K; 8) T366S, L368G, Y407A and F405K; 9) T366S, L368A, Y407V, F405K and E357A;

10) T366S, L368A, Y407V and K409A; 11) T366S, L368A, Y407V, K409A and K392D; 12) T366S, L368G, Y407A and K409A; 13) T366S, L368A, Y407V, K409A and E357A; wherein the position of the amino acid is determined according to the EU index of the KABAT number.

26. The proteinaceous heterodimer according to any one of embodiments 15-25, wherein the first Fc subunit comprises the first modification, the second Fc subunit comprises the second modification, and the first modification and the second modification comprise an amino acid substitution at a group of positions selected from any of the following groups: 1) the first modification: Y349 and T366; and the second modification: D356, T366, L368, Y407 and F405; 2) the first modification: Y349, T366 and F405; and the second modification: D356, T366, L368 and Y407; 3) the first modification: Y349, T366 and K409; and the second modification: D356, T366, L368, Y407 and F405; 4) the first modification: Y349, T366, F405, K360 and Q347; and the second modification: D356, T366, L368, Y407 and Q347; 5) the first modification: Y349, T366, F405 and Q347; and the second modification: D356, T366, L368, Y407, K360 and Q347; 6) the first modification: Y349, T366, K409, K360 and Q347; and the second modification: D356, T366, L368, Y407, F405 and Q347; 7) the first modification: Y349, T366, K409 and Q347; and the second modification: D356, T366, L368, Y407, F405, K360 and Q347; 8) the first modification: T366, K409 and K392; and the second modification: T366, L368, Y407, D399 and F405; 9) the first modification: T366 and K409; and the second modification: T366, L368, Y407 and F405; 10) the first modification: T366, K409 and Y349; and the second modification: T366, L368, Y407, F405 and E357; 11) the first modification: T366, K409, Y349 and 5354; and the second modification: T366, L368, Y407, F405 and E357; 12) the first modification: T366 and F405; and the second modification: T366, L368, Y407 and K409; 13) the first modification: T366, F405 and D399; and the second modification: T366, L368, Y407, K409 and K392; 14) the first modification: T366, F405 and Y349; and the second modification: T366, L368, Y407, K409 and E357; 15) the first modification: T366, F405, Y349 and S354; and the second modification: T366, L368, Y407, K409 and E357; wherein the position of the amino acid is determined according to the EU index of the KABAT number.

27. The proteinaceous heterodimer according to any one of embodiments 15-26, wherein the first Fc subunit comprises the first modification, the second Fc subunit comprises the second modification, wherein the first modification and the second modification comprise a group of amino acid substitutions selected from any of the following groups: 1) the first modification: Y349C and T366W; and the second modification: D356C, T366S, L368A, Y407V and F405K; 2) the first modification: Y349C, T366W and F405K; and the second modification: D356C, T366S, L368A and Y407V; 3) the first modification: Y349C, T366W and K409E; and the second modification: D356C, T366S, L368A, Y407V and F405K; 4) the first modification: Y349C, T366W and K409A; and the second modification: D356C, T366S, L368A, Y407V and F405K; 5) the first modification: Y349C, T366W, F405K, K360E and Q347E; and the second modification: D356C, T366S, L368A, Y407V and Q347R; 6) the first modification: Y349C, T366W, F405K and Q347R; and the second modification: D356C, T366S, L368A, Y407V, K360E and Q347E; 7) the first modification: Y349C, T366W, K409A, K360E and Q347E; and the second modification: D356C, T366S, L368A, Y407V, F405K and Q347R; 8) the first modification: Y349C, T366W, K409A and Q347R; and the second modification: D356C, T366S, L368A, Y407V, F405K, K360E and Q347E; 9) the first modification: T366W, K409A and K392D; and the second modification: T366S, L368A, Y407V, D399S and F405K; 10) the first modification: T366W and K409A; and the second modification: T366S, L368G, Y407A and F405K; 11) the first modification: T366W, K409A and Y349D; and the second modification: T366S, L368A, Y407V, F405K and E357A; 12) the first modification: T366W, K409A, Y349D and S354D; and the second modification: T366S, L368A, Y407V, F405K and E357A; 13) the first modification: T366W and F405K; and the second modification: T366S, L368A, Y407V and K409A; 14) the first modification: T366W, F405K and D399S; and the second modification: T366S, L368A, Y407V, K409A and K392D; 15) the first modification: T366W and F405K; and the second modification: T366S, L368G, Y407A and K409A; 16) the first modification: T366W, F405K and Y349D; and the second modification: T366S, L368A, Y407V, K409A and E357A; 17) the first modification: T366W, F405K, Y349D and S354D; and the second modification: T366S, L368A, Y407V, K409A and E357A; wherein the position of the amino acid is determined according to the EU index of the KABAT number.

28. The proteinaceous heterodimer according to embodiment 27, wherein the first Fc subunit comprises the first modification, the second Fc subunit comprises the second modification, the first modification comprises the amino acid substitutions T366W and K409A, and the second modification comprises the amino acid substitutions T366S, L368G, Y407A and F405K, wherein the position of the amino acid is determined according to the EU index of the KABAT number.

29. The proteinaceous heterodimer according to any one of embodiments 1-28, wherein at least one of said one or more interleukins is fused to said second Fc subunit.

30. The proteinaceous heterodimer according to embodiment 29, wherein at least one of said one or more interleukins is fused to an amino-terminal amino acid of said second Fc subunit.

31. The proteinaceous heterodimer according to embodiment 30, wherein in said second monomeric member, at least two of said one or more interleukins are fused to each other to form an interleukin dimer, and said interleukin dimer is further fused to the amino-terminal amino acid of said second Fc subunit.

32. The proteinaceous heterodimer according to any one of embodiments 1-31, wherein said first monomeric member does not comprise any interleukin.

33. The proteinaceous heterodimer according to any one of embodiments 1-32, wherein said first monomeric member consists of said first Fc subunit.

34. The proteinaceous heterodimer according to any one of embodiments 1-31, wherein at least one of said one or more interleukins is fused to said first Fc subunit.

35. The proteinaceous heterodimer according to embodiment 34, wherein at least one of said one or more interleukins is fused to an amino-terminal amino acid of said first Fc subunit.

36. The proteinaceous heterodimer according to embodiment 35, wherein in said first monomeric member, at least two of said one or more interleukins are fused to each other to form an interleukin dimer, and said interleukin dimer is further fused to the amino-terminal amino acid of said first Fc subunit.
37. The proteinaceous heterodimer according to any one of embodiments 34-36, wherein said second monomeric member does not comprise any interleukin.
38. The proteinaceous heterodimer according to any one of embodiments 34-37, wherein said second monomeric member consists of said second Fc subunit.
39. An isolated nucleic acid or isolated nucleic acids encoding the proteinaceous heterodimer according to any one of embodiments 1-38.
40. A vector or vectors comprising the isolated nucleic acid or isolated nucleic acids according to embodiment 39.
41. An isolated host cell comprising the isolated nucleic acid or isolated nucleic acids according to embodiment 39 or the vector or vectors according to embodiment 40.
42. A protein mixture, comprising: 1) the proteinaceous heterodimer according to any one of embodiments 1-38; 2) a first homodimer formed by two identical copies of said first monomeric member according to any one of embodiments 1-38; and 3) a second homodimer formed by two identical copies of said second monomeric member according to any one of embodiments 1-38; wherein a percentage of said proteinaceous heterodimer in said protein mixture is at least 50%.
43. The protein mixture according to embodiment 42, wherein the percentage of the second homodimer is less than the percentage of the first homodimer.
44. The protein mixture according to any one of embodiments 42-43, wherein the percentage of the second homodimer is at most 10%.
45. The protein mixture according to any one of embodiments 42-44, wherein the protein mixture substantially comprises none of said second homodimer.
46. The protein mixture according to any one of embodiments 42-45, wherein the protein mixture is produced directly by a host cell, without enrichment of said proteinaceous heterodimer and/or removing of said first or said second homodimer.
47. A pharmaceutical composition comprising the proteinaceous heterodimer according to any one of embodiments 1-38; or the protein mixture according to any one of embodiments 42-46, and optionally a pharmaceutically acceptable excipient.
48. The pharmaceutical composition according to embodiment 47, wherein the proteinaceous heterodimer is formulated for oral administration, intravenous administration, intramuscular administration, in-situ administration at the site of a tumor, inhalation, rectal administration, vaginal administration, transdermal administration, or administration via subcutaneous repository.
49. Use of the proteinaceous heterodimer according to any one of embodiments 1-38, or the protein mixture according to any one of embodiments 42-46 in the manufacture of a medicament and/or a kit for inhibiting growth of a tumor or a tumor cell.
50. Use of the proteinaceous heterodimer according to any one of embodiments 1-38, or the protein mixture according to any one of embodiments 42-46 in the manufacture of a medicament for treating cancer in a subject in need thereof.
51. A method for inhibiting growth of a tumor or a tumor cell, comprising contacting said tumor or tumor cell with an effective amount of the proteinaceous heterodimer according to any one of embodiments 1-38, or the protein mixture according to any one of embodiments 42-46.
52. The method according to embodiment 51, wherein said contacting occurs in vitro or in vivo.
53. A method for treating cancer in a subject in need thereof, comprising administering to the subject an effective amount of the proteinaceous heterodimer according to any one of embodiments 1-38, or the protein mixture according to any one of embodiments 42-46.
54. A method for producing a proteinaceous heterodimer according to any one of embodiments 1-38 or a protein mixture according to any one of embodiments 42-46, comprising (i) culturing the host cell of embodiment 41 under conditions to effect expression of the proteinaceous heterodimer, and (ii) harvesting the expressed proteinaceous heterodimer or a protein mixture comprising said proteinaceous heterodimer.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

EXAMPLES

The examples and preparations provided below further illustrate and exemplify the proteinaceous heterodimer of the present disclosure and methods of using and preparing thereof. It is to be understood that the scope of the present disclosure is not limited in any way by the scope of the following examples and preparations.

Example 1 Modification and Preparation of Nucleic Acids

1.1 Fc Modifications

Amino acid modifications (e.g., amino acid substitutions) were made to the interface residues of human IgG1 Fc domain to obtain the following groups of modifications (as shown in table 1 below), chain A is also referred to as Fc9 or the first Fc subunit, and chain B is also referred to as Fc6 or the second Fc subunit in the present disclosure:

TABLE 1

| Groups of amino acid modifications | | | |
|---|---|---|---|
| Group | Fc Chain | Modifications | SEQ ID NO |
| 1 | A | Y349C + T366W | 1 |
| | B | D356C + T366S + L368A + Y407V + F405K | 2 |
| 2 | A | Y349C + T366W + F405K | 3 |
| | B | D356C + T366S + L368A + Y407V | 4 |
| 3 | A | Y349C + T366W + K409E | 5 |
| | B | D356C + T366S + L368A + Y407V + F405K | 2 |
| 4 | A | Y349C + T366W + K409A | 6 |
| | B | D356C + T366S + L368A + Y407V + F405K | 2 |
| 5 | A | Y349C + T366W + F405K + K360E + Q347E | 7 |
| | B | D356C + T366S + L368A + Y407V + Q347R | 8 |
| 6 | A | Y349C + T366W + F405K + Q347R | 9 |
| | B | D356C + T366S + L368A + Y407V + K360E + Q347E | 10 |
| 7 | A | Y349C + T366W + K409A + K360E + Q347E | 11 |
| | B | D356C + T366S + L368A + Y407V + F405K + Q347R | 12 |
| 8 | A | Y349C + T366W + K409A + Q347R | 13 |
| | B | D356C + T366S + L368A + Y407V + F405K + K360E + Q347E | 14 |
| 9 | A | T366W + K409A + K392D | 15 |
| | B | T366S + L368A + Y407V + D399S + F405K | 16 |
| 10 | A | T366W + K409A | 17 |
| | B | T366S + L368G + Y407A + F405K | 18 |
| 11 | A | T366W + K409A + Y349D | 19 |
| | B | T366S + L368A + Y407V + F405K + E357A | 20 |
| 12 | A | T366W + K409A + Y349D + S354D | 21 |
| | B | T366S + L368A + Y407V + F405K + E357A | 20 |
| 13 | A | T366W + F405K | 22 |
| | B | T366S + L368A + Y407V + K409A | 23 |
| 14 | A | T366W + F405K + D399S | 24 |
| | B | T366S + L368A + Y407V + K409A + K392D | 25 |
| 15 | A | T366W + F405K | 22 |
| | B | T366S + L368G + Y407A + K409A | 26 |
| 16 | A | T366W + F405K + Y349D | 27 |
| | B | T366S + L368A + Y407V + K409A + E357A | 28 |
| 17 | A | T366W + F405K + Y349D + S354D | 29 |
| | B | T366S + L368A + Y407V + K409A + E357A | 28 |

Subsequently, formation of heterodimer proteins comprising the groups of modifications listed in table 1 above were examined using a ScFv-Fc/Fc system, as explained in detail below.

First of all, human immunoglobulin gammal (IgG1) constant region amino acid sequence was obtained from the database Uniprot (P01857), to get wildtype human IgG1-Fc region amino acid sequence (SEQ ID NO:30). The polynucleotide fragment encoding wild type human IgG1-Fc was obtained by RT-PCR from human PBMC total RNA (SEQ ID NO: 31, named as the Fc gene fragment). A polynucleotide fragment encoding a mouse kappaIII signal peptide (SEQ ID NO:32) was added to the 5' end of the Fc gene by overlapping PCR, and then subcloned into the vector pcDNA4 (Invitrogen, Cat V86220), to obtain a recombinant expression vector for expressing human IgG1-Fc in mammalian cells.

A nucleic acid molecule encoding a ScFv-Fc fusion protein (SEQ ID NO:33) was synthesized, wherein the ScFv refers to an anti-HER2 single chain antibody, the amino acid sequence of the ScFv-Fc fusion protein is as set forth in SEQ ID NO: 34. The ScFv-Fc gene fragment was then subcloned into the vector pcDNA4 (Invitrogen, Cat V86220), to obtain a recombinant expression vector for expressing the ScFv-Fc fusion protein in mammalian cells.

In some cases, a polypeptide encoding a variable region of a camel single domain antibody (VhH) was fused to the N terminal of the Fc gene fragment to obtain a fusion gene fragment (as set forth in SEQ ID NO: 35) encoding the fusion protein VhH-Fc (as set forth in SEQ ID NO: 36). It was then subcloned into the vector pcDNA4 (Invitrogen, Cat V86220), to obtain a recombinant expression vector for expressing the fusion protein VhH-Fc in mammalian cells.

Then, the amino acid modifications as listed in table 1 above were respectively introduced into the ScFv-Fc (groups 1-17), the VhH-Fc (groups 9-12, 14, 15 and 17), and the Fc gene fragment (groups 1-8) by overlapping PCR, wherein chain A refers to the Fc subunit in ScFv-Fc and chain B refers to the independent Fc subunit or the Fc subunit in VhH-Fc. The gene fragments with amino acid modifications were respectively subcloned into the vector pcDNA4 (Invitrogen, Cat V86220), to obtain recombinant expression vectors for expressing the modified ScFv-Fc fusion proteins, the modified Fc proteins, and the modified VhH-Fc fusion proteins in mammalian cells. Then, suspend-cultured HEK293 cells (ATCC CRL-1573™) were transfected with the constructed expression vectors with PEI. For each group, the expression vector expressing the A chain (ScFv-Fc fusion protein) and that expressing the B chain (Fc protein or VhH-Fc fusion protein) were co-transfected at a ratio of 1:1. After culturing for 5-6 days, supernatant of the transient expression products was collected, and the expression products comprising corresponding protein heterodimers were preliminarily purified using ProteinA affinity chromatography. Each of the preliminarily purified expression products comprises the homodimer protein ScFv-Fc/ScFv-Fc, the homodimer protein Fc/Fc (or the homodimer protein VhH-Fc/VhH-Fc) and the heterodimer protein ScFv-Fc/Fc (or the heterodimer protein ScFv-Fc/VhH-Fc), present in various percentages, respectively. Since the molecular weight of these proteins (i.e., the homodimers and the heterodimers) are different, their corresponding percentage could be determined according to corresponding band intensities reflected on non-reduced SDS-PAGE gels. The intensities were quantified and the results are summarized in tables 2-5 below.

TABLE 2

| Percentage of homodimer proteins and heterodimer proteins in expression products | | | |
|---|---|---|---|
| Group | ScFv-Fc homodimer (%) | ScFv-Fc/Fc heterodimer (%) | Fc homodimer (%) |
| 1 | 24 | 58 | 18 |
| 2 | 10 | 70 | 20 |
| 3 | 25 | 57 | 18 |
| 4 | 10 | 77 | 13 |

TABLE 3

| Percentage of homodimer proteins and heterodimer proteins in expression products | | | |
|---|---|---|---|
| Group | ScFv-Fc homodimer (%) | ScFv-Fc/Fc heterodimer (%) | Fc homodimer (%) |
| 2 | 17 | 60 | 23 |
| 5 | 14 | 72 | 14 |
| 6 | 14 | 62 | 24 |
| 4 | 21 | 69 | 10 |
| 7 | 24 | 64 | 12 |
| 8 | 21 | 71 | 8 |

TABLE 4

| Percentage of homodimer proteins and heterodimer proteins in expression products | | | |
|---|---|---|---|
| Group | ScFv-Fc homodimer (%) | ScFv-Fc/VhH-Fc heterodimer (%) | VhH-Fc homodimer (%) |
| 4 | 13 | 68 | 19 |
| 9 | 7 | 80 | 13 |
| 10 | 15 | 85 | 0 |
| 11 | 14 | 83 | 3 |
| 12 | 10 | 84 | 6 |

TABLE 5

| Percentage of homodimer proteins and heterodimer proteins in expression products | | | |
|---|---|---|---|
| Group | ScFv-Fc homodimer (%) | ScFv-Fc/VhH-Fc heterodimer (%) | VhH-Fc homodimer (%) |
| 2 | 9 | 64 | 27 |
| 14 | 6 | 81 | 13 |
| 15 | 5 | 88 | 7 |
| 17 | 9 | 84 | 7 |

As can be seen from tables 2-5 above, all groups of modifications promoted heterodimer formation very effectively. For illustrative purposes, the modifications in group 10 (modifications in chain A: T366W+K409A; modifications in chain B: T366S+L368G+Y407A+F405K) were used in the following examples to generate the immunoconjugate or the protein mixtures of the present disclosure.

1.2 Preparation of $(IL10)_2$-Fc6

First of all, sequence information of human interleukin 10 (IL10) (P22301) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366S, L368G, Y407A and F405K) were introduced into the IgG1-Fc fragment, and the polypeptide obtained thereby is referred to as Fc6. Then, a linker sequence "$(GGGGS)_3$" (SEQ ID NO: 37) was added to the N-terminus of the Fc6, to obtain linker-Fc6. The corresponding DNA sequence encoding it was then designed using online tool DNAworks (helixweb.nih.gov/dnaworks/). Then, a linker sequence "$(GGGGS)_3$" (SEQ ID NO: 37) was added between two copies of IL10, to obtain $(IL10)_2$. Polynucleotide sequences encoding $(IL10)_2$ were then added to the 5' end of the polynucleotide sequences encoding the linker-Fc6, thereby obtaining and synthesizing a polynucleotide sequence encoding the fusion protein $(IL10)_2$-Fc6. The amino acid sequence of $(IL10)_2$-Fc6 is as set forth in SEQ ID NO: 38, and the polynucleotide sequence encoding it is as set forth in SEQ ID NO: 39.

1.3 Preparation of IL10-Fc

First of all, sequence information of human interleukin 10 (IL10) (P22301) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Then, a linker sequence "$(GGGGS)_3$" (SEQ ID NO: 37) was added to the N-terminus of IgG1-Fc, to obtain linker-Fc. The corresponding DNA sequence encoding it was then designed using online tool DNAworks (helixweb.nih.gov/dnaworks/). Polynucleotide sequences encoding IL10 were added to the 5' end of the polynucleotide sequences encoding the linker-Fc, thereby obtaining and synthesizing a polynucleotide sequence encoding the fusion protein IL10-Fc. The amino acid sequence of IL10-Fc is as set forth in SEQ ID NO: 40, and the polynucleotide sequence encoding it is as set forth in SEQ ID NO: 41.

1.4 Preparation of Fc9

Amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366W and K409A) were introduced into the IgG1Fc fragment, and the polypeptide obtained thereby is referred to as Fc9. The amino acid sequence of Fc9 is as set forth in SEQ ID NO: 17, and the polynucleotide sequence encoding it is as set forth in SEQ ID NO: 42.

1.5 Preparation of Anti-EGFR (Cetuximab)

Full length amino acid sequences of the heavy chain and light chain of Cetuximab (also known as Erbitux or Erb, which is an antibody against epidermal growth factor receptor EGFR) were obtained, and corresponding DNA sequences encoding these amino acid sequences were obtained using online tool DNAworks (helixweb.nih.gov/dnaworks/). Then, nucleic acid molecules encoding the light chain of Cetuximab (Erb-LC) were synthesized. The amino acid sequence of Erb-LC is as set forth in SEQ ID NO: 43, and the corresponding polynucleotide sequence encoding it is as set forth in SEQ ID NO:44. Then, point mutations (T366W and K409A) were introduced into the polynucleotide sequences encoding the Fc region of Cetuximab heavy chain gene, and nucleic acid molecules encoding the modified Cetuximab heavy chain were synthesized (referred to herein as Erb-Fc9), the corresponding polypeptide encoding it was named as Erb-Fc9. The amino acid sequences of Erb-Fc9 is as set forth in SEQ ID NO: NO: 45, and the polynucleotide sequence encoding it is as set forth in SEQ ID NO: NO: 46.

1.6 Preparation of $(IL10)_2$-Fc

First of all, sequence information of human interleukin 10 (IL10) (P22301) was obtained from the National Center for Biotechnology Information (NCBI), Then, a linker sequence "$(GGGGS)_3$" was added between two IL10, to get $(IL10)_2$, and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Then, a linker sequence "$(GGGGS)_3$" (SEQ ID NO: 37) was added to the N-terminus of IgG1-Fc, to obtain linker-Fc. The corresponding DNA sequence encoding it was then designed using online tool DNAworks (helixweb.nih.gov/dnaworks/). Polynucleotide sequences encoding $(IL10)_2$ were added to the 5' end of the polynucleotide sequences encoding the linker-Fc, thereby obtaining and synthesizing a polynucleotide sequence encoding the fusion protein $(IL10)_2$-Fc. The amino acid sequence of $(IL10)_2$-Fc is as set forth in SEQ ID NO: 47 and the polynucleotide sequence encoding it is as set forth in SEQ ID NO: 48.

1.7 Preparation of Fc6-$(IL10)_2$

First of all, sequence information of human interleukin 10 (IL10) (P22301) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366S, L368G, Y407A and F405K) were introduced into the IgG1-Fc fragment, and the polypeptide obtained thereby is referred to as Fc6.

Then, a linker sequence "$(GGGGS)_3$" (SEQ ID NO: 37) was added to the C-terminus of the Fc6, to obtain Fc6-linker. The corresponding DNA sequence encoding it was then designed using online tool DNAworks (helixweb.nih.gov/dnaworks/). Then, a linker sequence "$(GGGGS)_3$" (SEQ ID NO: 37) was added between two copies of IL10, to obtain $(IL10)_2$. Polynucleotide sequences encoding $(IL10)_2$ were then added to the 3' end of the polynucleotide sequences encoding the Fc6-linker, thereby obtaining and synthesizing a polynucleotide sequence encoding the fusion protein Fc6-$(IL10)_2$. The amino acid sequence of Fc6-$(IL10)_2$ is as set forth in SEQ ID NO: 55, and the polynucleotide sequence encoding it is as set forth in SEQ ID NO: 56.

1.8 Preparation of IL10-Fc6

First of all, sequence information of human interleukin 10 (IL10) (P22301) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366S, L368G, Y407A and F405K) were introduced into the IgG1-Fc fragment, and the polypeptide obtained thereby is referred to as Fc6. Then, a linker sequence "$(GGGGS)_3$" (SEQ ID NO: 37) was added to the N-terminus of the Fc6, to obtain linker-Fc6. The corresponding DNA sequence encoding it was then designed using online tool DNAworks (helixweb.nih.gov/dnaworks/). Polynucleotide sequences encoding IL10 were added to the 5' end of the polynucleotide sequences encoding the linker-Fc6, thereby obtaining and synthesizing a polynucleotide sequence encoding the fusion protein IL10-Fc6. The amino acid sequence of IL10-Fc6 is as set forth in SEQ ID NO: 53, and the polynucleotide sequence encoding it is as set forth in SEQ ID NO: 54.

1.9 Preparation of $(IL10)_2$-Fc9

First of all, sequence information of human interleukin 10 (IL10) (P22301) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366W and K409A) were introduced into the IgG1Fc fragment, and the polypeptide obtained thereby is referred to as Fc9. Then, a linker sequence "$(GGGGS)_3$" (SEQ ID NO: 37) was added to the N-terminus of the Fc9, to obtain linker-Fc9. The corresponding DNA sequence encoding it was then designed using online tool DNAworks (helixweb.nih.gov/dnaworks/). Then, a linker sequence "$(GGGGS)_3$" (SEQ ID NO: 37) was added between two copies of IL10, to obtain $(IL10)_2$. Polynucleotide sequences encoding $(IL10)_2$ were then added to the 5' end of the polynucleotide sequences encoding the linker-Fc9, thereby obtaining and synthesizing a polynucleotide sequence encoding the fusion protein $(IL10)_2$-Fc9. The amino acid sequence of $(IL10)_2$-Fc9 is as set forth in SEQ ID NO: 57, and the polynucleotide sequence encoding it is as set forth in SEQ ID NO: 58.

1.10 Preparation of Fc6

Amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366S, L368G, Y407A and F405K) were introduced into the IgG1Fc fragment, and the polypeptide obtained thereby is referred to as Fc6. The amino acid sequence of Fc6 is as set forth in SEQ ID NO: 18, and the polynucleotide sequence encoding it is as set forth in SEQ ID NO: 59.

Example 2 Construction of Recombinant Plasmids

The nucleic acid molecules (encoding $(IL10)_2$-Fc6, IL10-Fc, Fc9, Erb-Fc9, Erb-LC, $(IL10)_2$-Fc, Fc6-$(IL10)_2$, IL10-Fc6, $(IL10)_2$-Fc9 and Fc6) obtained according to Example 1 were digested with HindIII and EcoRI (Takara), and then sub-cloned into the vector pcDNA4/myc-HisA (Invitrogen, V863-20), respectively. The plasmids obtained were verified by sequencing, and the correct recombinant plasmids were named as: pcDNA4-$(IL10)_2$-Fc6, pcDNA4-IL10-Fc, pcDNA4-Fc9, pcDNA4-Erb-Fc9, pcDNA4-Erb-LC, pcDNA4-$(IL10)_2$-Fc, pcDNA4-Fc6-$(IL10)_2$, pcDNA4-IL10-Fc6, pcDNA4-$(IL10)_2$-Fc9 and pcDNA4-Fc6 respectively.

Example 3 Expression and Purification of the Proteinaceous Heterodimers

Two days before transfection, 12× 600 mL suspension domesticated HEK293 (ATCC, CRL-1573™) cells were prepared for transient transfection, the cells were seeded at a density of $0.8\times10^6$ cells/ml. Two days later, three aliquots of cell suspension were centrifuged, and then resuspended in 600 mL Freestyle293 culture medium.

The recombinant expression vectors obtained from Example 2 were divided into the following groups:

Group A: pcDNA4-IL10-Fc6 (200 μg)+pcDNA4-Fc9 (200 μg)

Group B: pcDNA4-$(IL10)_2$-Fc6 (200 μg)+pcDNA4-Fc9 (200 μg)

Group C: pcDNA4-Fc6-$(IL10)_2$ (200 μg)+pcDNA4-Fc9 (200 μg)

Group D: pcDNA4-$(IL10)_2$-Fc9 (200 μg)+pcDNA4-Fc6 (200 μg)

Group E: pcDNA4-Erb-Fc9 (200 μg)+pcDNA4-Erb-LC (200 μg)+pcDNA4-$(IL10)_2$-Fc6 (200 μg)

Group F: pcDNA4-IL10-Fc (200 μg)

Group G: pcDNA4-$(IL10)_2$-Fc (200 μg)

All proteins were made in transiently transfected 293F cells. Briefly, FreeStyle 293F cells (Invitrogen) were grown in 293F medium (Invitrogen), transfected with non-linearized plasmid DNA and 293Fectin reagent (Invitrogen) and grown in shaker flask batches in volumes 80-100 mL/flask at 37° C., 5% $CO_2$ for 6 days. All proteins were purified by one-step protein A chromatography. The quality of each protein was determined by SDS-PAGE and SEC-HPLC. Similarly, the expression and purification results of the other proteinaceous heterodimers of the present application were verified and confirmed with SDS-PAGE.

The proteinaceous heterodimers thus obtained are named as (from Group A-E, respectively): IL10-Fc9, $(IL10)_2$-Fc9, reverse-$(IL10)_2$-Fc9, $(IL10)_2$-Fc6 (shown in FIGS. 1A-1D, respectively) and Erb-$(IL10)_2$, and the proteinaceous homodimers obtained from Group F-G is named as $(IL10\text{-}Fc)_2$ and $(IL10)_2$-Fc.

FIGS. 2A-2F show, as examples, that the proteinaceous heterodimers of $(IL10)_2$-Fc9 and Erb-$(IL10)_2$ were successfully expressed and purified. All the other proteins were also obtained similarly.

Figure 2A:
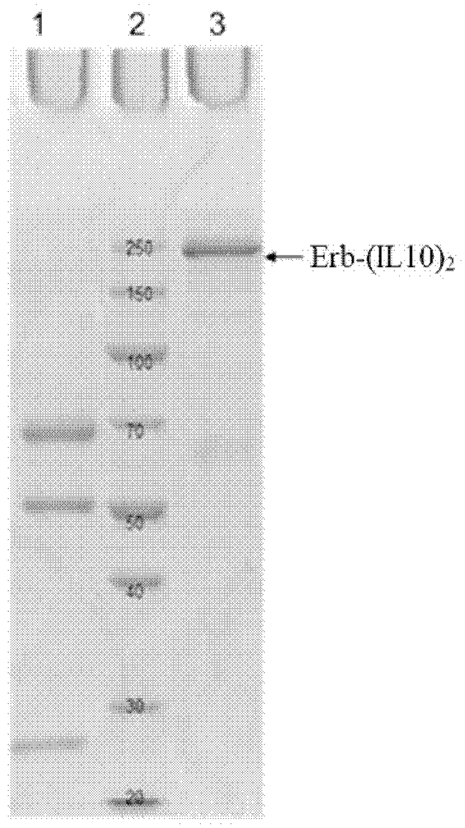
FIGS. 2A-2F illustrate the purification result of the proteinaceous heterodimers of the present disclosure, as shown by SDS-PAGE and SEC-HPLC analysis.

In FIG. 2A, lane 1 was loaded with Erb-$(IL10)_2$ (reducing); lane 2 was loaded with marker; lane 3 was loaded with Erb-$(IL10)_2$ (non-reducing).

Figure 2B:
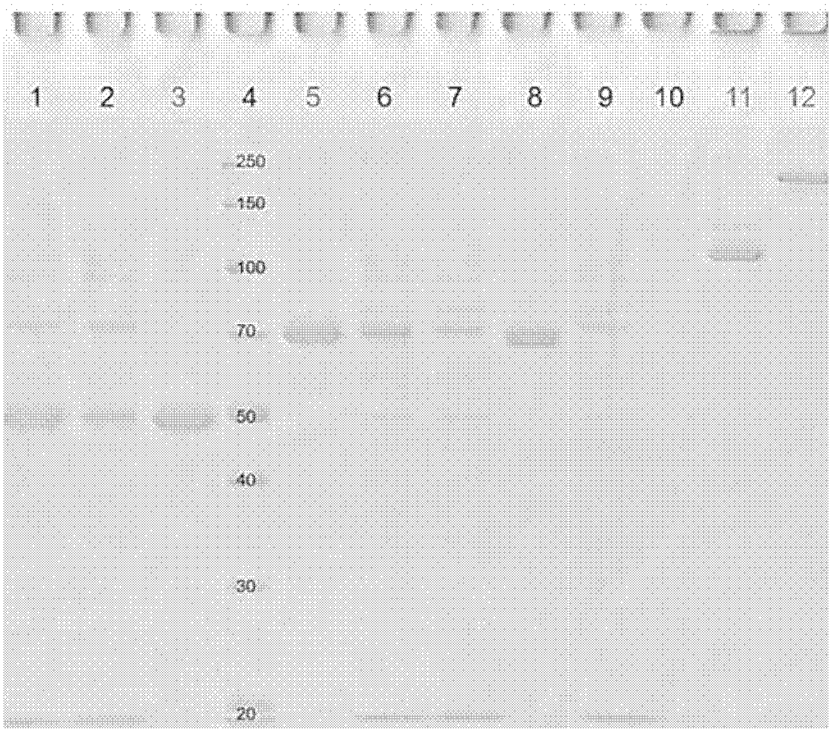

In FIG. 2B, lane 1 was loaded with $(IL10\text{-}Fc)_2$ (original sample); lane 2 was loaded with $(IL10\text{-}Fc)_2$ (flow-through); lane 3 was loaded with $(IL10\text{-}Fc)_2$ (eluted); lane 4 was loaded with marker; lane 5 was loaded with (IL10)2-Fc (eluted); lane 6 was loaded with $(IL10)_2$-Fc (original sample); lane 7 was loaded with $(IL10)_2$-Fc (flow through); lane 8 was loaded with BSA; lane 9 was loaded with blank buffer; lane10 was blank; lane 11 was loaded with $(IL10)_2$-Fc (eluted; non-reducing); and lane 12 was loaded with $(IL10)_2$-Fc (eluted; non-reducing).

Figure 2C:
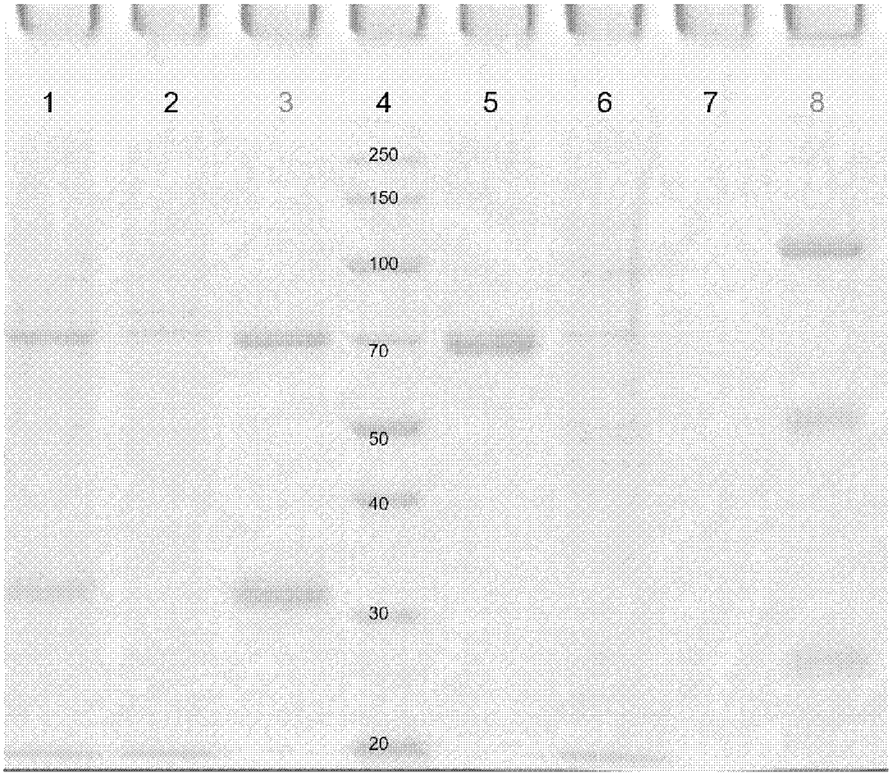

In FIG. 2C, lane 1 was loaded with $(IL10)_2$-Fc9 (original sample); lane 2 was loaded with $(IL10)_2$-Fc9 (flow-through); lane 3 was loaded with $(IL10)_2$-Fc9 (eluted); lane 4 was loaded with marker; lane 5 was loaded with BSA; lane 6 was loaded with blank buffer; lane 7 was blank; lane 8 was loaded with $(IL10)_2$-Fc9 (eluted; non-reducing).

Figure 2D:
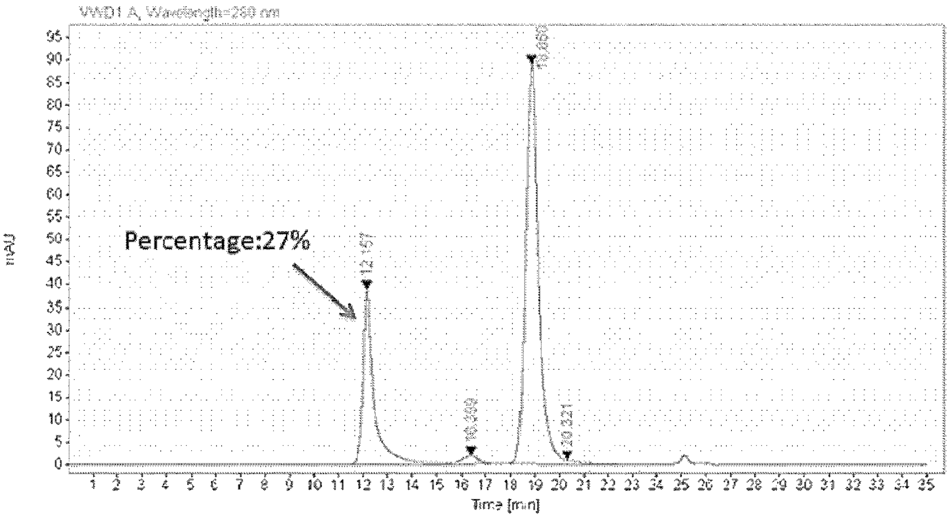

FIG. 2D shows the SEC-HPLC result, it can be seen that the percentage of undesired oligomers in the expression products of $(IL10\text{-}Fc)_2$ was about 27%.

Figure 2E:
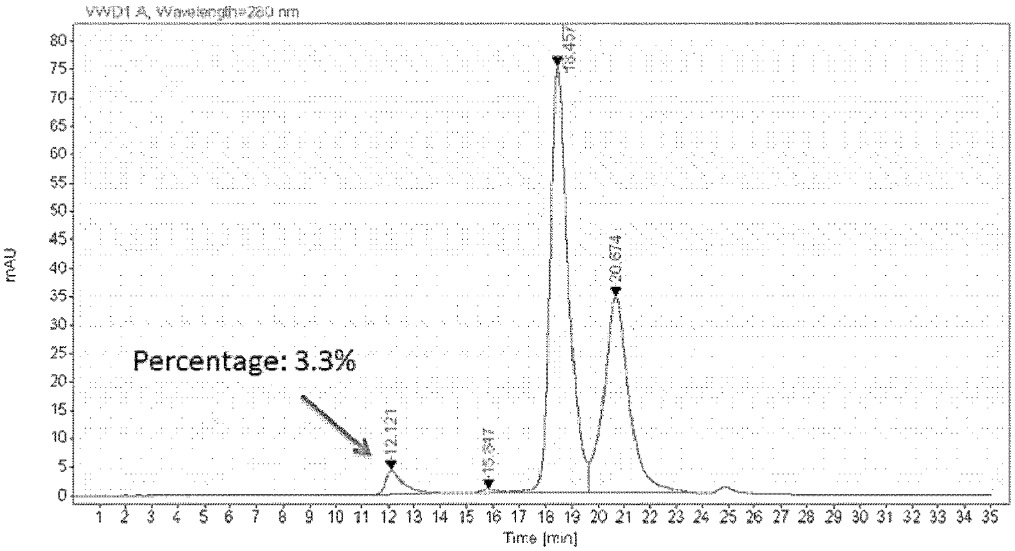

FIG. 2E shows the SEC-HPLC result, it can be seen that the percentage of undesired oligomers in the expression products of $(IL10)_2$-Fc9 was about 3.3%.

Figure 2F:
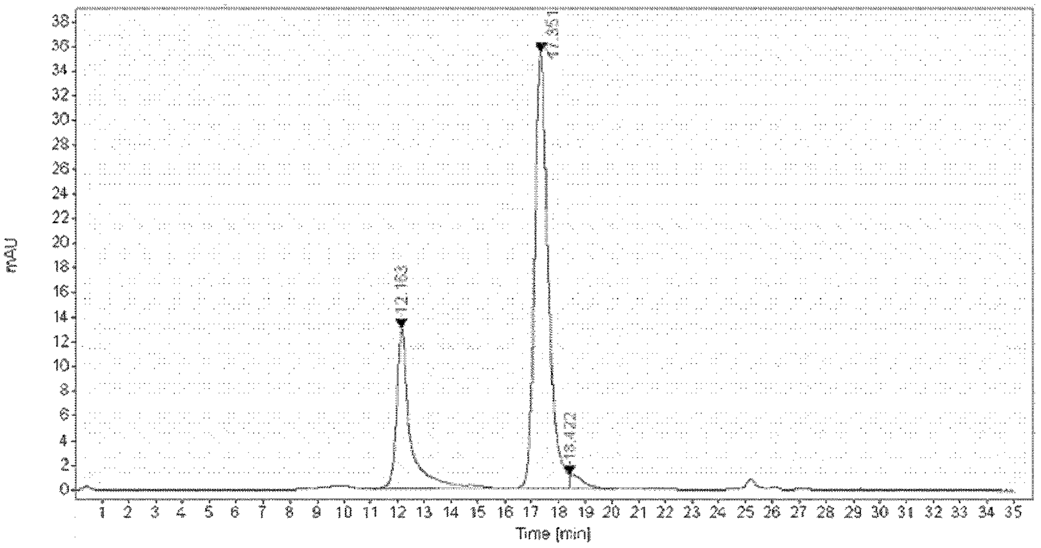

FIG. 2F shows the SEC-HPLC result, it can be seen that the percentage of undesired oligomers in the expression products of $(IL10)_2$-Fc was about 26%.

From these results, it can be seen that the proteinaceous heterodimers of the present disclosure have been successfully produced. Interestingly, the expression products of $(IL10)_2$-Fc9 contain much less undesired oligomers than the homodimer controls $(IL10\text{-}Fc)_2$ and $(IL10)_2$-Fc.

Example 4 Identification of Characteristics of Heterodimer Proteins

4.1 Detection on the Capacity of Binding to Human IL10R1 Proteins (ELISA)

Human IL10R1 (R&D, 9100-R1-050) was diluted to 5 μg/mL with coating buffer (50 mM $Na_2CO_3$, $NaHCO_3$ pH 9.6), 100 μL/well, overnight at 4° C. After washing, the plates were sealed with 3% BSA-PBS for 1 h at 37° C. Then, all samples were respectively diluted from 10000 ng/mL and were diluted 3-fold to a total of 11 concentrations, with the diluent (1% BSA-PBS) as a control, incubated at 37° C. for 2 h. After washing, Goat anti-hIgG-HRP (Sigma, A0170) was added and incubated at 37° C. for 1 h. The soluble one-component TMB substrate developing solution was added, and the developing was performed in dark at room temperature for 5-10 min. 2 N $H_2SO_4$ 50 μL/well was added to terminate the color development reaction. The $PD_{450\ nm}$ values were read on MD SpectraMax Plus 384 microplate Reader, and SoftMax Pro v5.4 was used for data processing and diagraph analysis, with the results shown in FIG. 3 and Table 6.

TABLE 6

$EC_{50}$ of hetero dimer proteins in binding to human IL10R1 proteins

| Name of heterodimer proteins | $EC_{50}$ (ng/ml) |
|---|---|
| Erb-$(IL10)_2$ | 2.940 |
| Reverse-$(IL10)_2$-Fc9 | 12.31 |
| $(IL10)_2$-Fc6 | 7.166 |
| $(IL10)_2$-Fc9 | 9.683 |

Figure 3:
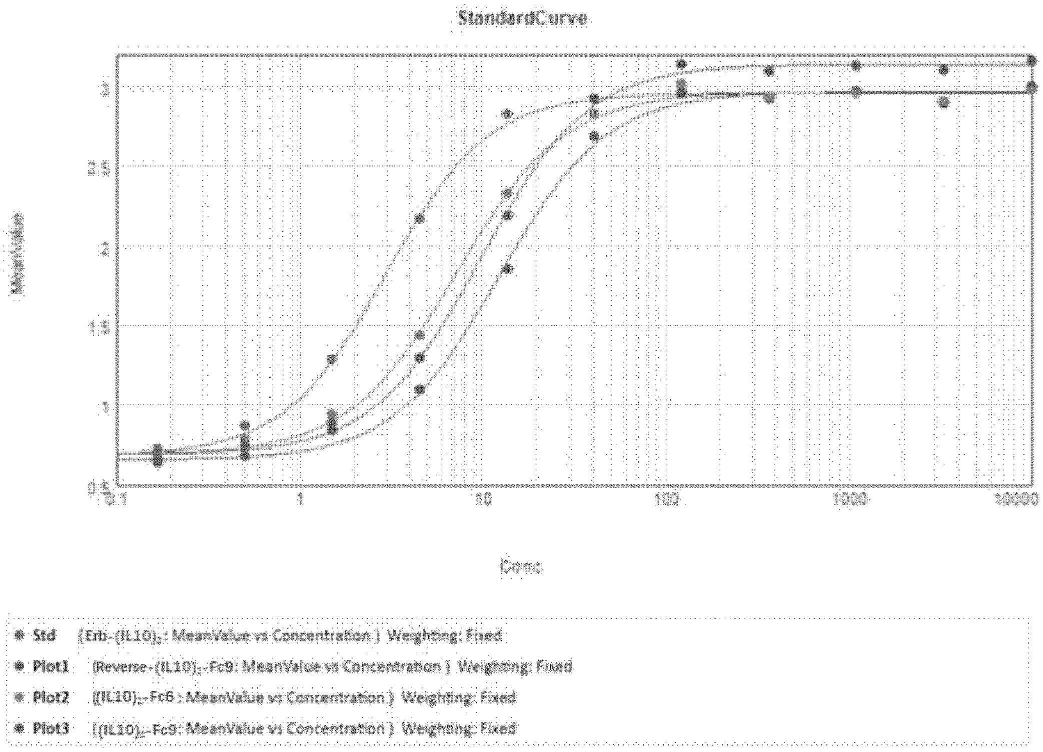
FIG. 3 illustrates the binding affinity to human IL10R1 proteins (ELISA).

As shown in FIG. 3, the affinity between Erb-$(IL10)_2$ and hIL10R1 was the highest. The binding affinities of Reverse-$(IL10)_2$-Fc9, $(IL10)_2$-Fc6 and $(IL10)_2$-Fc9 with hIL10R1 were similar to each other.

4.2 Enhancement of Proliferation of MC/9 Cells

MC/9 (ATCC CRL-8306) cells were seeded into 96-well plates at 100 μL/well. The amount of MC/9 was $5\times10^4$/well. All samples were diluted to a maximum concentration of $2\times10^4$ pM. Then the samples were diluted 4 times to a total of 9 concentrations, 100 μL/well. For the control group, 100

μL of DMEM medium was added. Each sample was done in duplicate. Then incubate for 2 days at 37° C. with 5% $CO_2$. Then discard 140 μL/well of the supernatant, and add 60 μL/well CellTiter-Glo Cell Activity Assay Agent(Promega G7571). Incubate for 15 min (100 rpm) with an orbital shaker in dark. Then transfer 100 μL/well of the supernatant to a new 96-well white plate, and measure the luminescence at the full wavelength with MD Spectra Max Plus 384 microplate reader, with the results shown in FIG. 4.

Figure 4:
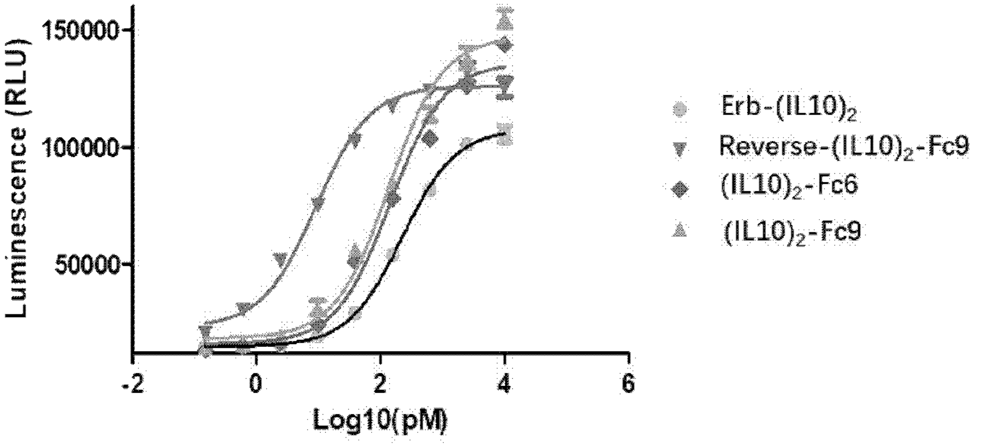
FIG. 4 illustrates the enhancement of proliferation of MC/9 cells.

As shown in FIG. 4, (IL10)2-Fc9 and (IL10)2-Fc6 proliferated nearly at the same level in vitro in MC/9 cell line. Reverse-(IL10)2-Fc9 has better proliferative effects than (IL10)2-Fc9. The in vitro function studies using MC/9 cells showed similar biological activity between (IL10)2-Fc9 and (IL10)2-Fc6 while reverse-(IL10)2-Fc9 showed higher biological activity.

Example 5 Tumor Control

5.1 Animals and Cell Culture

Female C57BL/6 mice were obtained from the Experimental Animal Centre of Chinese Academy of Science (Shanghai, China) at 8-week-old and maintained under specific pathogen-free conditions. All animals were used in accordance with the local ethics committee. This study was approved by the recommendations in the Guide for the Care and Use of Medical Laboratory Animals (Ministry of Health, People's Republic of China, 1998). The B16F10 melanoma cell line was generated in house and grown in DMEM medium supplemented with 10% (v/v) fetal bovine serum (FBS), 100 units/ml penicillin, and 100 μg/ml streptomycin (Gibco Invitrogen).

5.2 Tumor Growth

B16F10 cells ($5\times10^6$) were inoculated subcutaneously (s.c.) into the flanks of mice and allowed to grow for about 7 days. Tumor volumes were recorded to be two perpendicular diameters (length and width) and calculated as $V=ab^2/2$, where a and b are the longest and the shortest diameter, respectively. After 7 days, the tumor volume was measured to be around 70 $mm^3$.

5.3 Treatment

Figure 5A:
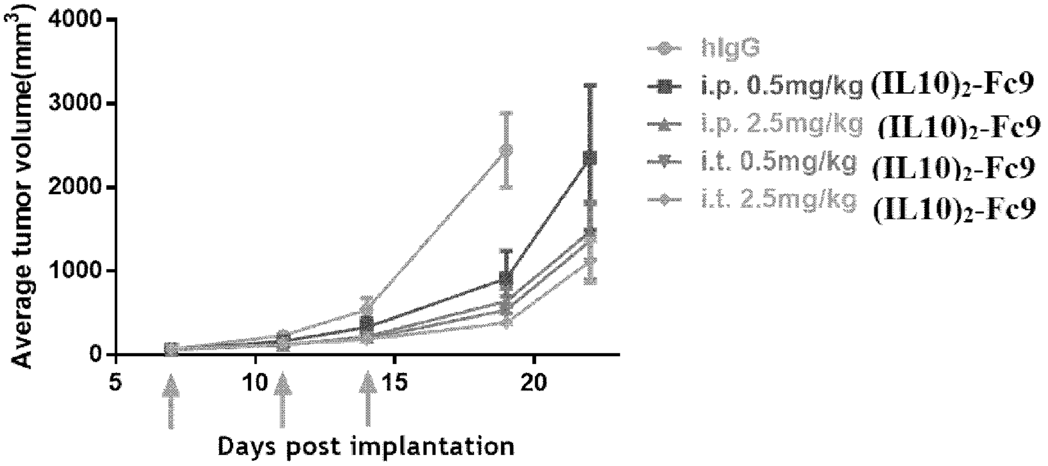
FIGS. 5A-5B illustrate the effect of tumor control of the proteinaceous heterodimers of the present disclosure.
Figure 5B:
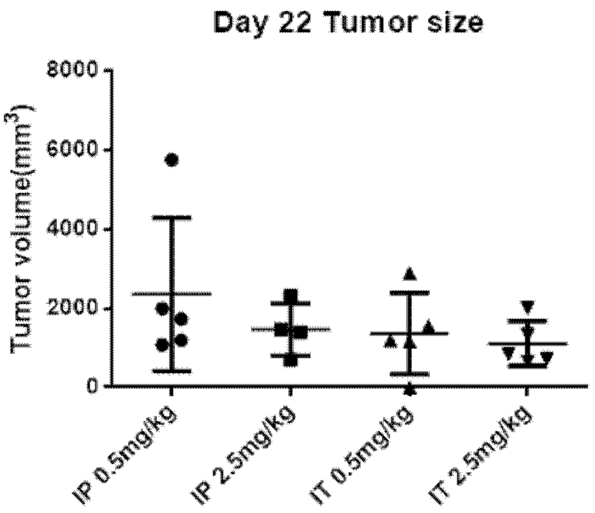

After 7 days of the implantation of B16F10 cells, $(IL10)_2$-Fc9 or isotype (hIgG) was injected intraperitoneally (i.p.) or intratumorally (i.t.) with the dosage of 0.5 mg/kg and 2.5 mg/kg, respectively. Dosing was administered twice per week, 3 times in total. Tumor size was measured twice per week, and the volume of the tumors was calculated to obtain a curve of tumor growth. The results are demonstrated in FIGS. 5A-5B. In FIG. 5A, the horizontal ordinate is the days after the implantation of B16F10 cells, and the vertical ordinate is the average volume of tumor, and it can be seen that $(IL10)_2$-Fc9 effectively reduced tumor volume in vivo when administered i.p. or i.t., while the control isotype couldn't. FIG. 5B shows the tumor volume on day 22 with the treatment of $(IL10)_2$-Fc9 (i.p. and i.t.) with different dosage. The measurement of tumor size was repeated by 5 times. It can be seen that $(IL10)_2$-Fc9, when administered i.p. and i.t. in different doses, reduced tumor volume in vivo.

Example 6 Effects of Proteinaceous Heterodimers in Tumor Control

6.1 Effects of $(IL10)_2$-Fc9 According to the Present Disclosure (High Concentration)

The C57BL/6 tumor control model was obtained as described above in Example 5. The mice were divided into two groups with 5 mice per group: Group isotype control, treated with 0.65 mg/kg human IgG1; Group $(IL10)_2$-Fc9, treated with 0.65 mg/kg $(IL10)_2$-Fc9. C57BL/6 mice were inoculated s.c. with B16F10-EGFR5 cells on day 0; $(IL10)_2$-Fc9 or human IgG1 was injected i.p. on day 7, 10, 14 respectively.

Figure 6A:
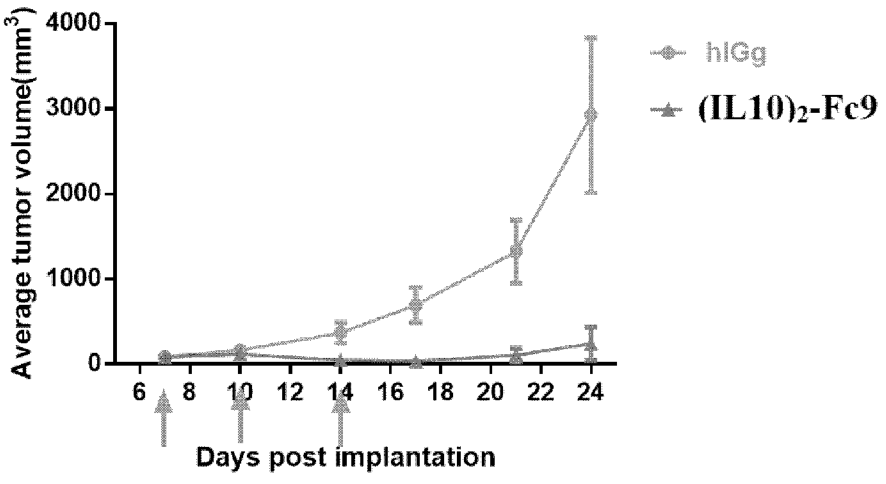
FIGS. 6A-6B illustrate the comparison between the high and low concentrations of the proteinaceous heterodimers in tumor control.

FIG. 6A shows the effects on tumor grow for isotype control and $(IL10)_2$-Fc9 of the present disclosure. It can be seen that $(IL10)_2$-Fc9 effectively reduced tumor volume in vivo, while the isotype control couldn't.

6.2 Effects of $(IL10)_2$-Fc9 According to the Present Disclosure (Low Concentration)

The C57BL/6 tumor control model was obtained as described above in Example 5. The mice were divided into two groups with 5 mice per group: Group isotype control, treated with 0.5 mg/kg human IgG1; Group $(IL10)_2$-Fc9, treated with 0.13 mg/kg $(IL10)_2$-Fc9 C57BL/6 mice were inoculated s.c. with B16F10-EGFR5 cells on day 0; $(IL10)_2$-Fc9 or human IgG1 was injected i.p. on day 7, 10, 14 respectively.

Figure 6B:
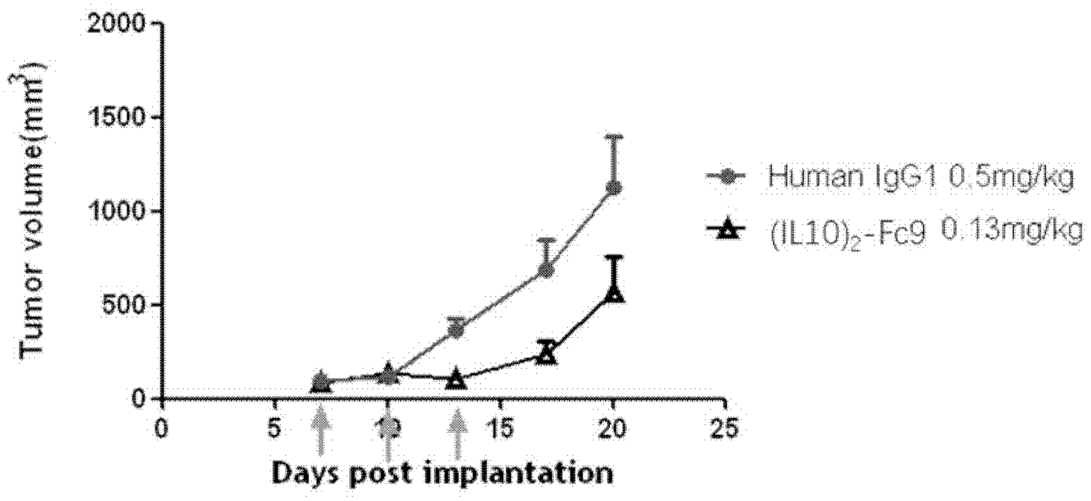

FIG. 6B shows the effects on tumor grow for isotype control and $(IL10)_2$-Fc9 of the present disclosure. It can be seen that $(IL10)_2$-Fc9 effectively reduced tumor volume in vivo, while the isotype control could not. Compared with the result in Example 6.1, the low concentration of $(IL10)_2$-Fc9 did not influence the result of tumor control effects.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A proteinaceous heterodimer comprising a first monomeric member and a second monomeric member different from said first monomeric member, wherein:

the amino acid sequence of the first monomeric member is as set forth in SEQ ID NO: 55, and the amino acid sequence of the second monomeric member is as set forth in SEQ ID NO: 17.

2. A proteinaceous heterodimer comprising a first monomeric member and a second monomeric member different from said first monomeric member, wherein:

the amino acid sequence of the first monomeric member is as set forth in SEQ ID NO: 57, and the amino acid sequence of the second monomeric member is as set forth in SEQ ID NO: 18.

* * * * *